United States Patent
Aki et al.

(10) Patent No.: US 9,834,505 B2
(45) Date of Patent: Dec. 5, 2017

(54) STABLE LIGAND MIXTURES AND PROCESSES FOR MAKING SAME

(71) Applicant: INVISTA NORTH AMERICA S.A.R.L., Wilmington, DE (US)

(72) Inventors: Sudhir Aki, Katy, TX (US); William J. Tenn, III, Beaumont, TX (US); Thomas E. Vos, Beaumont, TX (US)

(73) Assignee: INVISTA NORTH AMERICA S.A.R.L., Wilmington, DE (US)

( * ) Notice: Subject to any disclaimer, the term of this patent is extended or adjusted under 35 U.S.C. 154(b) by 252 days.

(21) Appl. No.: 14/404,068

(22) PCT Filed: May 24, 2013

(86) PCT No.: PCT/US2013/042631
§ 371 (c)(1),
(2) Date: Nov. 26, 2014

(87) PCT Pub. No.: WO2013/181095
PCT Pub. Date: Dec. 5, 2013

(65) Prior Publication Data
US 2015/0158812 A1 Jun. 11, 2015

Related U.S. Application Data

(60) Provisional application No. 61/654,648, filed on Jun. 1, 2012.

(51) Int. Cl.
| | | |
|---|---|---|
| C07C 253/30 | (2006.01) |
| C07F 9/40 | (2006.01) |
| C07F 9/6574 | (2006.01) |
| C07F 9/145 | (2006.01) |
| C07F 15/04 | (2006.01) |

(52) U.S. Cl.
CPC ............ C07C 253/30 (2013.01); C07F 9/145 (2013.01); C07F 9/4006 (2013.01); C07F 9/65744 (2013.01); C07F 15/04 (2013.01)

(58) Field of Classification Search
CPC ...... C07C 253/30; C07F 9/145; C07F 9/4006; C07F 9/65744
See application file for complete search history.

(56) References Cited

U.S. PATENT DOCUMENTS

| | | | |
|---|---|---|---|
| 3,655,723 A | 4/1972 | Drinkard, Jr. | |
| 5,981,722 A | 11/1999 | Chen et al. | |
| 6,153,800 A * | 11/2000 | Gelling | C07C 253/30 568/451 |
| 6,169,198 B1 | 1/2001 | Fischer et al. | |
| 7,470,805 B2 | 12/2008 | Rosier et al. | |
| 7,629,484 B2 | 12/2009 | Ritter | |
| 7,659,422 B2 | 2/2010 | Foo et al. | |
| 7,977,502 B2 | 7/2011 | Foo et al. | |
| 2004/0122251 A1* | 6/2004 | Rosier | C07C 253/10 558/348 |
| 2009/0182164 A1* | 7/2009 | Foo | C07C 253/10 558/338 |
| 2010/0267990 A1 | 10/2010 | Ritter et al. | |
| 2011/0196168 A1 | 8/2011 | Ostermaier | |

FOREIGN PATENT DOCUMENTS

| | | |
|---|---|---|
| WO | 2008/008930 A2 | 1/2008 |
| WO | 2013/181095 A1 | 12/2013 |

OTHER PUBLICATIONS

International Search Report and Written Opinion Received for PCT Application No. PCT/US2013/042631, dated Aug. 12, 2013, 9 pages.
International Preliminary Report and Patentability Report Received for PCT Patent Application No. PCT/US2013/042631, dated Jan. 30, 2014, 3 Pages.

* cited by examiner

*Primary Examiner* — Joseph R Kosack
(74) *Attorney, Agent, or Firm* — Robert B. Furr, Jr.; Nicholas P. Lanzatella

(57) ABSTRACT

A process of stabilizing a bidentate or tridentate phosphorus-based phosphite ester ligand or mixture thereof in a hydrocyanation reaction milieu comprising water, wherein the ligand or ligand mixture comprises one or more of (i) a bidentate biphosphite ligand of formula (III), $(R^{12}-X^{12})(R^{13}-X^{13})$ $P-X^{14}-Y-X^{24}-P(X^{22}-R^{22})$ $(X^{23}-R^{23})$ or (ii) a tridentate triphosphite ligand of formula (IIIA) $(R^{12}-X^{12})$ $(R^{13}-X^{13})$ $P-X^{14}-Y-X^{32}-P(X^{34}-R^{34})-(X^{33}-Y^{2}-R^{24}-P(X^{23}-R^{23})-(X^{22}-R^{22})$ where each X is oxygen or a bond and each Y is an optionally substituted C6-C20 arylene group, comprising admixing the bidentate and/or tridentate with a stabilizing amount of one or more monodentate phosphite ligand of formula $P(X^{1}-R^{1})(X^{2}-R^{2})(X^{3}-R^{3})$ where each X is oxygen or a bond, wherein the monodentate ligand has a rate of hydrolysis greater than the rate of hydrolysis of the bidentate or tridentate ligand in the presence of water in a hydrocyanation reaction milieu, and thereby preserve concentrations and proportions of the bidentate and/or tridentate ligand(s) in the ligand blend.

54 Claims, 3 Drawing Sheets

STABLE LIGAND MIXTURES AND PROCESSES FOR MAKING SAME

CROSS-REFERENCE TO RELATED APPLICATION

This application claims benefit of priority from U.S. Provisional Application No. 61/654,648 filed Jun. 1, 2012. This application hereby incorporates by reference this provisional application in its entirety.

FIELD OF THE INVENTION

The invention relates to stabilized nickel catalyst complexes incorporating phosphorus-based ligands including a phosphite ester bond which are used in the hydrocyanation of butadiene (BD) in the large scale commercial synthesis of adiponitrile (ADN), an important intermediate in the industrial production of nylon polyamides useful in forming films, fibers, and molded articles.

BACKGROUND OF THE INVENTION

U.S. Pat. No. 6,169,198 describes the process of hydrocyanation (reaction with HCN) of BD to prepare ADN, and explains that the process can generally be divided into three steps. First, mononitriles such as 3-pentenenitrile (3-PN) are formed by the reaction of HCN with BD, along with other nitriles, including isomers which must be isomerized in subsequent steps to achieve the desired straight chain ADN as a final product. Second is the isomerization of species such as 2-methyl-3-butenenitrile (2M3BN). Third is a second hydrocyanation of the pentenenitriles to yield the desired ADN.

U.S. Pat. No. 5,981,722 describes and exemplifies a new class of catalysts for such transformations by the use of diphosphite nickel complexes for the hydrocyanation and isomerizations. This class of catalysts is characterized by greater catalytic activity and resistance to HCN-derived degradation reactions.

U.S. Pat. No. 7,470,805 describes a process of hydrocyanation of diolefins in the presence of a catalytic system comprising a transition metal and mono- and pluri-dentate organophosphorus ligands. According to this, the use of a mixture of two ligands, monodentate and pluri (bi and/or tri)dentate, enables the pluridentate ligand to be preserved in the reaction milieu.

Monodentate and bidentate phosphorus-based ligands, depicted as formulae (7) and (8), and (3), respectively, as the structures are termed in U.S. Pat. No. 7,629,484, can be used in preparation of a transition metal-organophosphorus catalyst for reactions such as hydrocyanation.

Monodentate Ligand Examples of U.S. Pat. No. 7,629,484

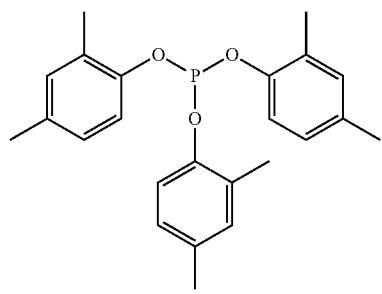

7

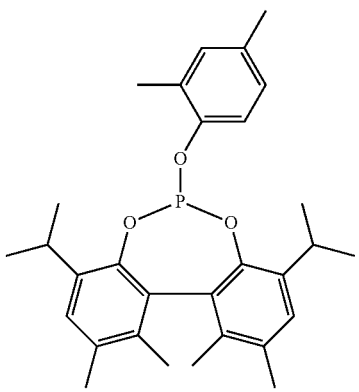

Bidentate Ligand Example of U.S. Pat. No. 7,629,484

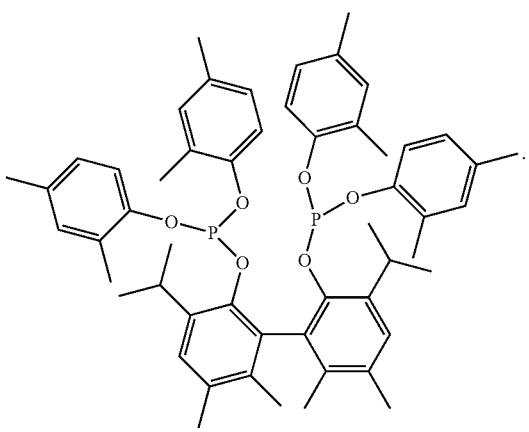

3

U.S. Pat. No. 7,659,422 describes a hydrocyanation process to produce ADN from BD with control of i) the overall feed molar ratio of 2-pentenenitriles to all unsaturated nitriles and ii) the overall feed molar ratio of HCN to all unsaturated nitriles. An example is given as a reaction mixture comprising a Lewis acid promoter ($FeCl_2$) and bidentate Ligand B, which is as depicted as identical to Compound (3) above.

U.S. Pat. No. 7,977,502 describes an integrated, continuous process for the production of 3-PN, the refining of 3-PN and the refining of 2M3BN by a process comprising contacting a feed stream in a reaction zone, maintaining residence time to convert about 95% or more of the HCN, distilling to create various streams.

U.S. Published Patent Application No. 2011/0196168 describes nickel-containing solids comprising nickel metal derived from basic nickel carbonates (BNCs) which are highly reactive with both monodentate and Bidentate phosphorus-containing ligands in forming nickel metal complexes, which can be for producing pentenenitriles and dinitriles by hydrocyanation.

SUMMARY OF THE INVENTION

Hydrocyanation reaction processes which utilize transition metal catalyst (e.g., nickel) complexes with monodentate, bidentate and/or tridentate phosphorus-based ligands comprising at least one phosphite ester bond can be assisted and the catalysts rendered more effective by the use of monodentate phosphorus-based ligands comprising at least one phosphite ester bond to trap a disproportionate share of water in process streams and thereby preserve the bidentate and/or tridentate ligands intact. Hydrocyanation ligand pools for nickel-ligand catalysts can comprise a bidentate and/or tridentate ligand admixed therewith a stabilizing amount of one or more monodentate ligands, such as can produced in the synthesis of the bidentate or tridentate ligand, or as can be deliberately added to the ligand blend for catalyst metal-complex formation. Such monodentate ligands can have a hydrolysis rate greater than the bidentate or tridentate ligand, serving as a scavenger of water in the reaction milieu and thereby inhibiting the breakdown of the more effective bidentate and/or tridentate ligand(s) of the ligand pool.

While not to limit the invention by a recitation of theory, one possible explanation consistent with this discovery is that admixing into the reaction stream one or more monodentate organophosphorus ligands suppresses formation of one or more products derived from the phosphorus-containing ligand, or derived from a catalyst formed from the ligand, or both, that can cause decreased catalytic activity of a catalyst mixture. The catalyst mixture can be recycled from a reaction zone effluent of the hydrocyanation reaction zone, or can be a catalyst mixture formed from a phosphorus-based ligand mixture recycled from the reaction zone effluent of the hydrocyanation reaction zone of a pentenenitrile hydrocyanation reaction, or can be a catalyst formed from the phosphorus-containing ligand in the reactor feed.

The invention can provide a process for stabilizing a phosphorus-based bidentate ligand of formula (III) or tridentate ligand of formula (IIIA) or a mixture thereof, in a hydrocyanation reaction milieu comprising water, the ligands having respective formulas:

a bidentate phosphorus-based ligand of formula (III)

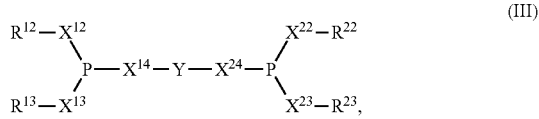

(III)

or, a tridentate phosphorus-based ligand of formula (IIIA)

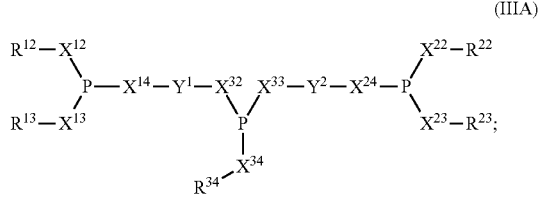

(IIIA)

wherein for the ligand of formula (III), $X^{12}$, $X^{13}$, $X^{14}$, $X^{22}$, $X^{23}$, and $X^{24}$, each independently is oxygen or a bond, provided that at least one of $X^{12}$, $X^{13}$, $X^{14}$, $X^{22}$, $X^{23}$, or $X^{24}$ is oxygen, and for the ligand of formula (IIIA), $X^{12}$, $X^{13}$, $X^{14}$, $X^{22}$, $X^{23}$, $X^{24}$, $X^{32}$, $X^{33}$, and $X^{34}$, each independently is oxygen or a bond, provided that at least one of $X^{12}$, $X^{13}$, $X^{14}$, $X^{22}$, $X^{23}$, $X^{24}$, $X^{32}$, $X^{33}$, or $X^{34}$ is oxygen;

for the ligand of formula (III), $R^{12}$, $R^{13}$, $R^{22}$, and $R^{23}$, and for the ligand of formula (IIIA), $R^{12}$, $R^{13}$, $R^{22}$, $R^{23}$, and $R^{34}$, each independently is (C1-C10)alkyl, (C3-C10)cycloalkyl, (C3-C10)cycloalkyl(C1-C10)alkyl, (C6-C20)aryl, or (C6-C20)aryl(C1-C10)alkyl, wherein for any (C6-C20)aryl or (C6-C20)aryl(C1-C10)alkyl of $R^{12}$, $R^{13}$, $R^{22}$, $R^{23}$, or $R^{34}$, each ring thereof is unsubstituted or is substituted with 1-4 substituents independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, and (C6-C20)aryl(C1-C10)alkyl; or, optionally, one or more of pairs $R^{12}$ and $R^{13}$ or $R^{22}$ and $R^{23}$ are mutually directly bonded, such that the $R^{12}X^{12}$ and $R^{13}X^{13}$ groups, or the $R^{22}X^{22}$ and $R^{23}X^{23}$ groups, or both, together with the respective phosphorus atom to which each pair of groups is bonded, forms a respective ring;

for the ligand of formula (III) the group Y, and for the ligand of formula (IIIA), the groups $Y^1$ and $Y^2$ independently, is an (C6-C20)arylene group, wherein each ring thereof is independently unsubstituted or is substituted with 1-4 (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, (C6-C20)aryl(C1-C10)alkyl, fluorine, chlorine, bromine, or (C1-C10)haloalkyl;

the process comprising admixing with the bidentate and/or the tridentate ligand a stabilizing amount of one or more monodentate phosphorus-based ligand of formula (IV)

(IV)

wherein $X^1$, $X^2$ and $X^3$ are each independently oxygen or a single bond, provided that at least one of $X^1$, $X^2$, or $X^3$ is an oxygen; and $R^1$, $R^2$ and $R^3$ is each independently (C1-C10)alkyl, (C3-C10)cycloalkyl, (C3-C10)cycloalkyl(C1-C10)alkyl, (C6-C20)aryl, or (C6-C20)aryl(C1-C10)alkyl, wherein for any (C6-C20)aryl or (C6-C20)aryl(C1-C10) alkyl of $R^1$, $R^2$, or $R^3$ each ring thereof is independently unsubstituted or is substituted with 1-4 substituents independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, and (C6-C20)aryl(C1-C10)alkyl; or, optionally, any two of $R^1$, $R^2$, or $R^3$ are directly bonded to each other such that any pair of $R^1X^1$, $R^2X^2$, and $R^3X^3$ groups, together with the phosphorus atom to which they are bonded, forms a ring;

wherein the monodentate ligand of formula (IV) has a rate of hydrolysis greater than a rate of hydrolysis of a bidentate ligand of formula (III) or a tridentate ligand of formula (IIIA) or a mixture thereof, in the presence of water in a hydrocyanation reaction milieu optionally further comprising an organic component, under conditions of concentration, temperature, and time sufficient to bring about hydrolysis of the monodentate ligand of formula (IV).

The invention can further provide a process of stabilizing a reaction mixture resulting from the catalytic hydrocyanation process of butadiene in the preparation of adiponitrile in the presence of a phosphorus-based ligand of formula (III) or formula (IIIA) or a mixture thereof, in a hydrocyanation reaction milieu comprising water, the ligands having respective formulas:

a bidentate phosphorus-based ligand of formula (III)

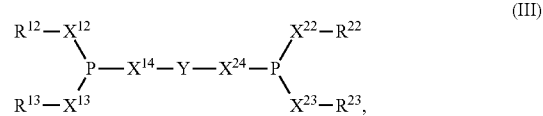

(III)

or,
a tridentate phosphorus-based ligand of formula (IIIA)

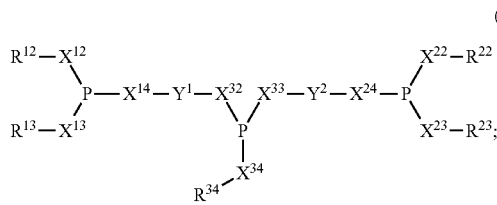

(IIIA)

wherein for the ligand of formula (III), $X^{12}$, $X^{13}$, $X^{14}$, $X^{22}$, $X^{23}$, and $X^{24}$, each independently is oxygen or a bond, provided that at least one of $X^{12}$, $X^{13}$, $X^{14}$, $X^{22}$, $X^{23}$, or $X^{24}$ is oxygen, and for the ligand of formula (IIIA), $X^{12}$, $X^{13}$, $X^{14}$, $X^{22}$, $X^{23}$, $X^{24}$, $X^{32}$, $X^{33}$, and $X^{34}$, each independently is oxygen or a bond, provided that at least one of $X^{12}$, $X^{13}$, $X^{14}$, $X^{22}$, $X^{23}$, $X^{24}$, $X^{32}$, $X^{33}$, or $X^{34}$ is oxygen;

for the ligand of formula (III), $R^{12}$, $R^{13}$, $R^{22}$, and $R^{23}$, and for the ligand of formula (IIIA), $R^{12}$, $R^{13}$, $R^{22}$, $R^{23}$, and $R^{34}$, each independently is (C1-C10)alkyl, (C3-C10)cycloalkyl, (C3-C10)cycloalkyl(C1-C10)alkyl, (C6-C20)aryl, or (C6-C20)aryl(C1-C10)alkyl, wherein for any (C6-C20)aryl or (C6-C20)aryl(C1-C10)alkyl of $R^{12}$, $R^{13}$, $R^{22}$, $R^{23}$, or $R^{34}$, each ring thereof is unsubstituted or is substituted with 1-4 substituents independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, and (C6-C20)aryl(C1-C10)alkyl; or, optionally, one or more of pairs $R^{12}$ and $R^{13}$ or $R^{22}$ and $R^{23}$ are mutually directly bonded, such that the $R^{12}X^{12}$ and $R^{13}X^{13}$ groups, or the $R^{22}X^{22}$ and $R^{23}X^{23}$ groups, or both, together with the respective phosphorus atom to which each pair of groups is bonded, forms a respective ring;

for the ligand of formula (III) the group Y, and for the ligand of formula (IIIA), the groups $Y^1$ and $Y^2$ independently, is an (C6-C20)arylene group, wherein each ring thereof is independently unsubstituted or is substituted with 1-4 (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, (C6-C20)aryl(C1-C10)alkyl, fluorine, chlorine, bromine, or (C1-C10)haloalkyl;

the process comprising adding to said reaction mixture before or during said hydrocyanation therewith a stabilizing amount of one or more monodentate phosphorus-based ligand of formula (IV)

(IV)

wherein $X^1$, $X^2$ and $X^3$ are each independently oxygen or a single bond, provided that at least one of $X^1$, $X^2$, or $X^3$ is an oxygen; and $R^1$, $R^2$ and $R^3$ is each independently (C1-C10)alkyl, (C3-C10)cycloalkyl, (C3-C10)cycloalkyl(C1-C10)alkyl, (C6-C20)aryl, or (C6-C20)aryl(C1-C10)alkyl, wherein for any (C6-C20)aryl or (C6-C20)aryl(C1-C10) alkyl of $R^1$, $R^2$, or $R^3$ each ring thereof is independently unsubstituted or is substituted with 1-4 substituents independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, and (C6-C20)aryl(C1-C10)alkyl; or, optionally, any two of $R^1$, $R^2$, or $R^3$ are directly bonded to each other such that any pair of $R^1X^1$, $R^2X^2$, and $R^3X^3$ groups, together with the phosphorus atom to which they are bonded, forms a ring;

wherein the monodentate ligand of formula (IV) has a rate of hydrolysis greater than a rate of hydrolysis of a bidentate ligand of formula (III) or a tridentate ligand of formula (IIIA) or a mixture thereof, in the presence of water in a hydrocyanation reaction milieu optionally further comprising an organic component, under conditions of concentration, temperature, and time sufficient to bring about hydrolysis of the monodentate ligand of formula (IV).

The invention can further provide a reaction mixture resulting from a catalytic hydrocyanation reaction process of butadiene in the preparation of adiponitrile, in a hydrocyanation reaction milieu comprising water, the reaction mixture comprising a phosphorus-based ligand of formula (III) or formula (IIIA) or a mixture thereof, the ligands having respective formulas:

a bidentate phosphorus-based ligand of formula (III)

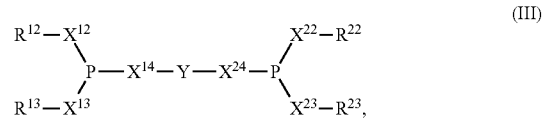

(III)

or,
a tridentate phosphorus-based ligand of formula (IIIA)

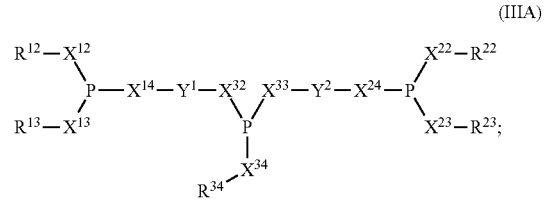

(IIIA)

wherein for the ligand of formula (III), $X^{12}$, $X^{13}$, $X^{14}$, $X^{22}$, $X^{23}$, and $X^{24}$, each independently is oxygen or a bond, provided that at least one of $X^{12}$, $X^{13}$, $X^{14}$, $X^{22}$, $X^{23}$, or $X^{24}$ is oxygen, and for the ligand of formula (IIIA), $X^{12}$, $X^{13}$, $X^{14}$, $X^{22}$, $X^{23}$, $X^{24}$, $X^{32}$, $X^{33}$, and $X^{34}$, each independently is oxygen or a bond, provided that at least one of $X^{12}$, $X^{13}$, $X^{14}$, $X^{22}$, $X^{23}$, $X^{24}$, $X^{32}$, $X^{33}$, or $X^{34}$ is oxygen;

for the ligand of formula (III), $R^{12}$, $R^{13}$, $R^{22}$, and $R^{23}$, and for the ligand of formula (IIIA), $R^{12}$, $R^{13}$, $R^{22}$, $R^{23}$, and $R^{34}$, each independently is (C1-C10)alkyl, (C3-C10)cycloalkyl, (C3-C10)cycloalkyl(C1-C10)alkyl, (C6-C20)aryl, or (C6-C20)aryl(C1-C10)alkyl, wherein for any (C6-C20)aryl or (C6-C20)aryl(C1-C10)alkyl of $R^{12}$, $R^{13}$, $R^{22}$, $R^{23}$, or $R^{34}$, each ring thereof is unsubstituted or is substituted with 1-4 substituents independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, and (C6-C20)aryl(C1-C10)alkyl; or, optionally, one or more of pairs $R^{12}$ and $R^{13}$ or $R^{22}$ and $R^{23}$ are mutually directly bonded, such that the $R^{12}X^{12}$ and $R^{13}X^{13}$ groups, or the $R^{22}X^{22}$ and $R^{23}X^{23}$ groups, or both, together with the respective phosphorus atom to which each pair of groups is bonded, forms a respective ring;

for the ligand of formula (III) the group Y, and for the ligand of formula (IIIA), the groups $Y^1$ and $Y^2$ independently, is an (C6-C20)arylene group, wherein each ring thereof is independently unsubstituted or is substituted with 1-4 (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cyclo alkyl (C1-C10)alkoxy, (C3-C10)cycloalkoxy(C1-C10)alkoxy, (C6-C20)aryl, (C6-C20)aryl(C1-C10)alkyl, fluorine, chlorine, bromine, or (C1-C10)haloalkyl;

and further comprising an amount of one of more monodentate phosphorus-based ligand of formula (IV)

wherein $X^1$, $X^2$ and $X^3$ are each independently oxygen or a single bond, provided that at least one of $X^1$, $X^2$, or $X^3$ is an oxygen; and $R^1$, $R^2$ and $R^3$ is each independently (C1-C10)alkyl, (C3-C10)cycloalkyl, (C3-C10)cycloalkyl(C1-C10)alkyl, (C6-C20)aryl, or (C6-C20)aryl(C1-C10)alkyl, wherein for any (C6-C20)aryl or (C6-C20)aryl(C1-C10) alkyl of $R^1$, $R^2$, or $R^3$ each ring thereof is independently unsubstituted or is substituted with 1-4 substituents independently selected from the group consisting of (C1-C10) alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10) alkoxy, (C3-C10)cycloalkoxy(C1-C10)alkoxy, (C6-C20) aryl, and (C6-C20)aryl(C1-C10)alkyl; or, optionally, any two of $R^1$, $R^2$, or $R^3$ are directly bonded to each other such that any pair of $R^1X^1$, $R^2X^2$, and $R^3X^3$ groups, together with the phosphorus atom to which they are bonded, forms a ring;

wherein a smaller proportion of the ligand of formula (IV) relative to the ligand of formula (III) or formula (IIIA) or mixture thereof, is present than the proportion of the ligand of formula (IV) relative to the ligand of formula (III) or formula (IIIA) or mixture thereof, that was present before the catalytic hydrocyanation reaction was commenced.

Accordingly, the present invention can provide technical solutions to the problem of regulating the proportions of phosphorus-based ligands in a ligand blend for use in a transition metal complex for hydrocyanation reactions, such as when the hydrocyanation reactions are carried out in the presence of even trace or controlled amounts of water. Solutions to regulation of levels of monodentate versus bidentate and/or tridentate phosphorus-based ligands in ligand blends are provided that enable the formation of catalysts, e.g., nickel complexes with the ligands of the blend, with favorable properties for use in hydrocyanation reactions. Ligand blends or pools for hydrocyanation catalysts comprising a metal-ligand complex, e.g., a nickel-phosphite complex, are provided, wherein monodentate ligands containing at least one phosphite ester bond are used to scavenge water in the hydrocyanation reaction milieu in the presence of bidentate and/or tridentate ligands containing at least one phosphite ester bond, such that the monodentate ligands are sacrificed due to their higher reaction reaction rate with water, compared to the more valuable bidentate and/or tridentate ligands. By use of processes of the invention, higher relative concentrations of favorable bidentate/tridentate ligands, can be maintained thereby. The more valuable and more effective bidentate and/or tridentate ligands are thus preserved from degradation, necessitating less makeup of these more bidentate and/or tridentate ligands.

DETAILED DESCRIPTION OF THE INVENTION

Figure 1:
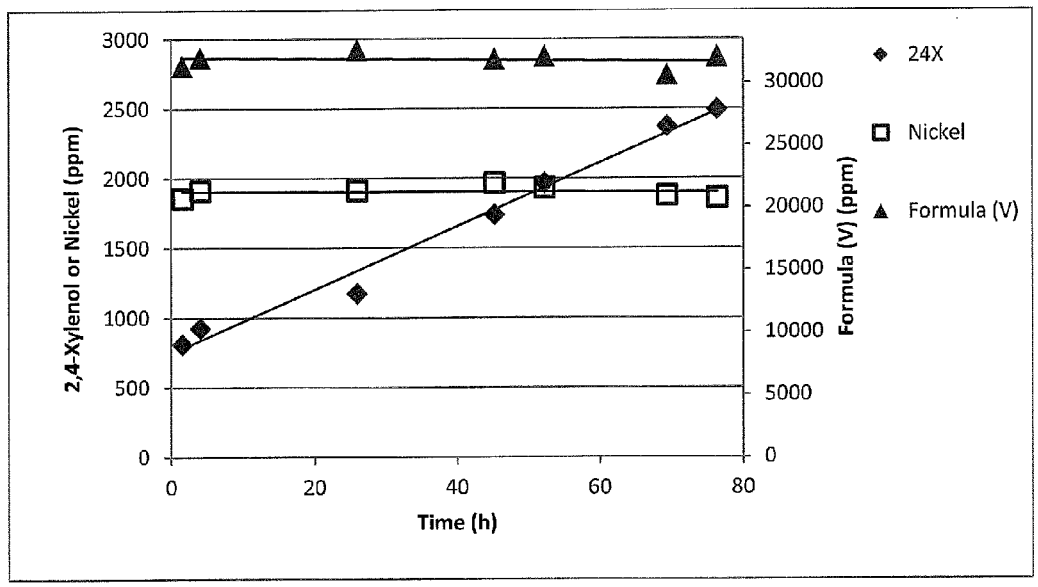
FIG. 1 shows the results of hydrolysis of a reaction mixture resulting from the catalytic hydrocyanation of butadiene in the preparation of adiponitrile in the presence of monophosphites of formulas (XIII) and (XIV).

As used in the specification and the appended claims, the singular forms "a," "an" and "the" include plural referents unless the context clearly dictates otherwise.

The term "about" as used herein, when referring to a numerical value or range, allows for a degree of variability in the value or range, for example, within 10%, or within 5% of a stated value or of a stated limit of a range.

All percent compositions are given as weight-percentages, unless otherwise stated.

Aspects of the present disclosure employ, unless otherwise indicated, techniques of chemistry, and the like, which are within the skill of the art. Such techniques are explained fully in the literature. Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

Phrases such as "under conditions suitable to provide" or "under conditions sufficient to yield" or the like, in the context of methods of synthesis, as used herein refers to reaction conditions, such as time, temperature, solvent, reactant concentrations, and the like, that are within ordinary skill for an experimenter to vary, that provide a useful quantity or yield of a reaction product. It is not necessary that the desired reaction product be the only reaction product or that the starting materials be entirely consumed, provided the desired reaction product can be isolated or otherwise further used.

By "chemically feasible" is meant a bonding arrangement or a compound where the generally understood rules of organic structure are not violated; for example a structure within a definition of a claim that would contain in certain situations a pentavalent carbon atom that would not exist in nature would be understood to not be within the claim. The structures disclosed herein are intended to include only "chemically feasible" structures, and any recited structures that are not chemically feasible, for example in a structure shown with variable atoms or groups, are not intended to be disclosed or claimed herein.

When a substituent is specified to be an atom or atoms of specified identity, "or a bond", a configuration is referred to when the substituent is "a bond" that the groups that are immediately adjacent to the specified substituent are directly connected to each other in a chemically feasible bonding configuration.

All chiral, diastereomeric, racemic forms of a structure are intended, unless a particular stereochemistry or isomeric form is specifically indicated. In several instances though an individual stereoisomer is described among specifically claimed compounds, the stereochemical designation does not imply that alternate isomeric forms are less preferred, undesired, or not claimed. Compounds used in the present invention can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

As used herein, the terms "stable compound" and "stable structure" are meant to indicate a compound that is sufficiently robust to survive isolation to a useful degree of purity from a reaction mixture, and formulation into an efficacious therapeutic agent. Only stable compounds are contemplated herein.

An "organic radical" or "organic group", as the term is used herein, refers to a portion or fragment or moiety, capable of bonding to another atom, wherein the group is carbon-based. By "carbon-based" is meant that at least a portion of the group comprises at least one carbon atom, which can be covalently bonded to other atoms capable of covalent bonding such as hydrogen, nitrogen, oxygen, halogen, sulfur, phosphorus, and the like, as is well known in the art.

When a group, e.g., an "alkyl" group or an "aryl" group, is referred to without any limitation on the number of atoms in the group, it is understood that the claim is definite and limited with respect the size of the alkyl group, both by definition; i.e., the size (the number of carbon atoms) possessed by a group such as an alkyl group is a finite number, bounded by the understanding of the person of ordinary skill as to the size of the group as being reasonable for a molecular entity; and by functionality, i.e., the size of the group such as the alkyl group is bounded by the functional properties the group bestows on a molecule containing the group such as solubility in aqueous or organic liquid media. Therefore, a claim reciting an "alkyl" or other chemical group or moiety is definite and bounded.

Standard abbreviations for chemical groups such as are well known in the art can be used herein, and are within ordinary knowledge; e.g., Me=methyl, Et=ethyl, i-Pr=isopropyl, Bu=butyl, t-Bu=tert-butyl; Ph=phenyl, Bn=benzyl, Ac=acetyl, Bz=benzoyl, and the like.

In general, "substituted" refers to an organic group as defined herein in which one or more bonds to a hydrogen atom contained therein are replaced by one or more bonds to a non-hydrogen atom such as, but not limited to, a halogen (i.e., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents J that can be bonded to a substituted carbon (or other) atom include F, Cl, Br, I, OR', OC(O)N(R')$_2$, CN, NO, NO$_2$, ONO$_2$, azido, CF$_3$, OCF$_3$, R', O (oxo), S (thiono), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$N(R')C(O)R', (CH$_2$)$_{0-2}$ N(R')N(R')$_2$, N(R')N(R')C(O)R', N(R')N(R')C(O)OR', N(R')N(R')CON (R')$_2$, N(R')SO$_2$R', N(R')SO$_2$N(R')$_2$, N(R')C(O)OR, N(R')C (O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted; for example, wherein R' can be hydrogen, alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl or R' can be independently mono- or multi-substituted with J; or wherein two R' groups bonded to a nitrogen atom or to adjacent nitrogen atoms can together with the nitrogen atom or atoms form a heterocyclyl, which can be mono- or independently multi-substituted with J.

Substituent groups J can independently be halo, nitro, cyano, OR, NR$_2$, or R, or is C(O)OR, C(O)NR$_2$, OC(O)OR, OC(O)NR$_2$, N(R)C(O)OR, N(R)C(O)NR$_2$ or thio/thiono analogs thereof. By "thio/thiono analogs thereof", with respect to a group containing an O, is meant that any or all O atoms in the group can be replaced by an S atom; e.g., for group C(O)OR, a "thio/thiono analog thereof" includes C(S)OR, C(O)SR, and C(S)SR; e.g., for group OC(O)NR$_2$, a "thio/thiono analog thereof" includes SC(O)NR$_2$, OC(S) NR$_2$, and SC(S)NR$_2$; and so forth.

When a substituent is monovalent, such as, for example, F or Cl, it is bonded to the atom it is substituting by a single bond. When a substituent is more than monovalent, such as O, which is divalent, it can be bonded to the atom it is substituting by more than one bond, i.e., a divalent substituent is bonded by a double bond; for example, a C substituted with O forms a carbonyl group, C=O, which can also be written as "CO", "C(O)", or "C(=O)", wherein the C and the O are double bonded. When a carbon atom is substituted with a double-bonded oxygen (=O) group, the oxygen substituent is termed an "oxo" group. When a divalent substituent such as NR is double-bonded to a carbon atom, the resulting C(=NR) group is termed an "imino" group. When a divalent substituent such as S is double-bonded to a carbon atom, the results C(=S) group is termed a "thiocarbonyl" or "thiono" group.

Alternatively, a divalent substituent such as O or S can be connected by two single bonds to two different carbon atoms. For example, O, a divalent substituent, can be bonded to each of two adjacent carbon atoms to provide an epoxide group, or the O can form a bridging ether group, termed an "oxy" group, between adjacent or non-adjacent carbon atoms, for example bridging the 1,4-carbons of a cyclohexyl group to form a [2.2.1]-oxabicyclo system. Further, any substituent can be bonded to a carbon or other atom by a linker, such as (CH$_2$)$_n$ or (CR'$_2$)$_n$ wherein n is 1, 2, 3, or more, and each R' is independently selected.

Alkyl groups include straight chain and branched alkyl groups and cycloalkyl groups having from 1 to about 20 carbon atoms, and typically from 1 to 12 carbons or, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed above, for example, amino, hydroxy, cyano, carboxy, nitro, thio, alkoxy, and halogen groups.

Cycloalkyl groups are cyclic alkyl groups such as, but not limited to, cyclopropyl, cyclobutyl, cyclopentyl, cyclohexyl, cycloheptyl, and cyclooctyl groups. The cycloalkyl group can have 3 to about 8-12 ring members, or, the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

(Cycloalkyl)alkyl groups, also denoted cycloalkylalkyl, are alkyl groups as defined above in which a hydrogen or carbon bond of the alkyl group is replaced with a bond to a cycloalkyl group as defined above.

The term "alkoxy" refers to an oxygen atom connected to an alkyl group, including a cycloalkyl group, as are defined above. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structures are substituted therewith.

Aryl groups are cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. Aryl groups can contain about 6 to about 14 carbons in the ring portions of the groups. Aryl groups can be unsubstituted or substituted, as defined above. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed above. Aryl groups can also bear fused rings, such as fused cycloalkyl rings, within the meaning herein. For example, a tetrahydronaphthyl ring is an example of an aryl group within the meaning herein. Accordingly, an aryl ring includes, for example, a partially hydrogenated system, which can be unsubstituted or substituted, and includes one or more aryl rings substituted with groups such as alkyl, alkoxyl, cycloalkyl, cycloalkoxyl, cycloalkylalkyl, cycloalkoxyalkyl, and the like, and also fused with, e.g., a cycloalkyl ring.

Organophosphorus compounds include molecular entities wherein one or more phosphorus atoms is present, and one or more organic radicals or moieties is also present. An organophosphorus compound can further include other elements such as oxygen, halogens, hydrogen, nitrogen, and the like. Some terms in common usage for various classes of organophosphorus compounds, wherein P is a phosphorus atom and R indicates an organic moiety that is bonded via a carbon-phosphorus bond to the phosphorus atom, include "phosphine" ($PR_3$), "phosphine oxide" ($P(O)R_3$), "phosphinite" ($P(OR)R_2$), "phosphonite" ($P(OR)_2R$), "phosphinare" ($ROP(O)R_2$), "phosphite" ($P(OR)_3$), "phosphonate" ($RP(O)(OR)_2$), and "phosphate" ($P(O)(OR)_3$).

A "phosphorus-based ligand" as the term is used herein refers to a ligand containing at least one phosphorus atom, that is suitable for formation of a complex with a transition metal such as nickel, wherein the complex can possess catalytic activity for an organic reaction such as a hydrocyanation reaction of an olefin, such as the hydrocyanation of butadiene to yield pentenenitrile, or the hydrocyanation of pentenenitrile to yield adiponitrile. The term "phosphorus-based" refers to an organic compound that contains at least one phosphorus atom, whether or not it has catalytic activity.

A "monodentate" phosphorus-based ligand contains a single phosphorus atom per molecule, which can complex a metal atom such as nickel. A "bidentate" phosphorus-based ligand contains two phosphorus atoms per molecule, both of which can complex a single metal atom, such as a nickel atom. A "tridentate" phosphorus-based ligand contains three phosphorus atoms per molecule, all three of which can complex a single metal atom, such as a nickel atom.

The term "adding to said reaction mixture before or during said hydrocyanation therewith a stabilizing amount of one or more monodentate phosphorus-based ligand of formula (IV)" as used herein refers to either deliberate addition of the one of more monodentate ligands of formula (IV), or not removing the one or more monodentate ligands of formula (IV) present in a synthetic reaction product of a reaction synthesizing the bidentate ligand of formula (III) or the tridentate ligand of formula (IIIA) or both, when the bidentate and/or tridentate ligand is prepared and used without removal of the monodentate ligand present as a process impurity.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4.

The compound or set of compounds, such as are used in the inventive methods, can be any one of any of the combinations and/or sub-combinations of the elements as described herein.

A compound as shown in any of the Examples, or among the exemplary compounds, is provided.

Provisos can apply to any of the disclosed categories wherein any one or more of the other above disclosed categories or species can be excluded from such categories.

Hydrocyanation of Butadiene

The hydrocyanation of BD to yield ADN directly or indirectly through isomerization and/or additional hydrocyanation of intermediates with modern phosphorus-containing catalysts set forth below is well known in the art as evidenced by U.S. Pat. Nos. 7,977,502; and 7,659,422 and U.S. Published Applications 2009/0182164 and 2010/0267990. Various modifications can be used alone or in combination to achieve the desired efficiency with the selected components of the reaction. Thus, separation steps, temperatures, refining, distillation, isomerization zones, pressures, elimination of constituents along the pathway, column sizes and configurations, stream velocities, recycling, and other process variables can be adjusted to modify the overall ADN production as required.

The catalyst composition can be dissolved in a solvent that is non-reactive toward, and miscible with, the hydrocyanation reaction mixture. Suitable solvents include, for example, aliphatic and aromatic hydrocarbons with 1 to 10 carbon atoms, and nitrile solvents such as acetonitrile. Alternatively, 3PN, a mixture of isomeric pentenenitriles, a mixture of isomeric methylbutenenitriles, a mixture of isomeric pentenenitriles and isomeric methylbutenenitriles, or the reaction product from a previous reaction campaign, can be used to dissolve to the catalyst composition.

The HCN-containing feed, the BD-containing feed, and the catalyst composition are contacted in a reaction zone which can be contained in any suitable equipment known to one skilled in the art. One or more pieces of conventional equipment can be used to provide the reaction zone, for example continuous stirred-tank reactors, loop-type bubble column reactors, gas circulation reactors, bubble column reactors, tubular reactors, or combinations thereof, optionally with apparatus for removing at least a portion of the heat of reaction.

The reaction temperature is typically maintained within the range of about 80° C. to about 140° C., for example within the range of about 100° C. to about 130° C. Generally, the reaction pressure should be sufficient to maintain the reagents in the liquid state, with such pressure at least, in part, a function of the amount of unreacted BD present in the reaction mixture.

Though the invention is not limited by an upper limit of pressure, for practical purposes the pressure generally ranges from about 15 psia to about 300 psia (about 103 kPa to about 30 2068 kPa).

HCN, substantially free of carbon monoxide, oxygen, ammonia, and water can be introduced to the reaction as a vapor, liquid, or mixtures thereof. As an alternative, cyanohydrins can be used as the source of HCN. See, for example, U.S. Pat. No. 3,655,723.

The molar ratio of the HCN in the feed to the BD in the feed is in the range of about 0.90:1.00 to about 1.04:1.00, for example in the range of about 0.92:1.00 to about 0.98:1.00.

This range of molar ratios can be advantageous over those 40 with a significantly larger excess of BD to HCN in that there can be less unreacted BD to recover and recycle to the process, and yield losses to 2-methylglutaronitrile (MGN) and to BD dimers, oligomers, and related species can be reduced. The molar ratio of the zero-valent nickel in the feed to the BD in the feed is in the range of about 0.00005:1.00 to about 0.0050:1.00, for example in the range about 0.0001:1.00 to about 0.0010:1.00.

The residence time in the reaction zone (for example, the time necessary for the combined feeds to displace one reactor so volume in a continuous-stirred-tank-reactor (CSTR) is typically determined by the desire to maintain the 2M3BN concentration below about 15 weight percent of the total mass of the reaction mixture, for example at or below about 10 weight percent of the total mass of the reaction mixture, and is also related to the catalyst concentration and reaction temperature. Generally residence times will be in the range of about 0.5 to about 15 hours, for example in the range of about 1 to about 10 hours.

Water can be present in commercially available BD. Water can be undesirable in hydrocyanation processes as it can react with the phosphorus-containing ligand to produce hydrolysis products which are less active or inactive for the desired hydrocyanation and isomerization reactions. The ligand hydrolysis products can also promote undesired side reactions.

Prior to its use in hydrocyanation, BD can be purified to remove impurities such as TBC and water. TBC can be removed from BD by a variety of techniques, for example by distillation or by passing the liquid BD over an absorbent bed such as alumina. Distillation can also be used to remove other impurities, for example 4-vinyl-1-cyclohexene, from BD. Water can be removed from BD by a variety of techniques, for example by passing liquid BD over molecular sieves having a pore size smaller than 10 Angstrom units or by contacting it with alumina.

Phosphorus-Based Ligand for Hydrocyanation Catalysts

A phosphorus-based ligand containing at least one phosphite ester bond can be a component of a hydrocyanation catalyst, such as when combined with a transition metal, e.g., nickel, as is known in the art. The metal, such as nickel, can be zero-valent, i.e., in metallic form. Reaction of the metal with the ligand can make the complex soluble in certain organic solvents. The ligand can be, for example, a phosphite, a phosphonite, a phosphinite, a phosphine, or a mixed phosphorus-based ligand or a combination of such members, provided the ligand contains at least one hydrolyzable P—O—C bond, wherein P is a phosphorus atom (which additionally bears other substituents), O is an oxygen atom, and C represent an organic radical, such as an aryl group, as described herein.

A phosphorus-based ligand can be monodentate or multidentate, for example, bidentate or tridentate. The term "monodentate" is well known in the art, and means that each molecule of the ligand possesses a single phosphorus atom (e.g., a compound of formula (IV)), which can be bonded to a single metal atom. The term "bidentate" is well known in the art, and means that each molecule of the ligand possesses two phosphorus atoms (e.g., a compound of formula (III)), and both phosphorus atoms of the ligand can be bonded to a single metal atom. The term "tridentate" means that each molecule of the ligand possesses three phosphorus atoms (e.g., a compound of formula (IIIA)), and all three phosphorus atoms on the ligand can be bonded to a single metal atom. The terms "bidentate" and "tridentate" are also known in the art as chelate ligands.

As used herein, the term "mixed phosphorus-based ligand" means a phosphorus-based ligand comprising at least one combination selected from the group consisting of a phosphite-phosphonite, a phosphite-phosphinite, a phosphite-phosphine, a phosphonite-phosphinite, a phosphonite-phosphine, and a phosphinite-phosphine or a combination of such members, provided that there is at least one P—O—C bond, wherein P is a phosphorus atom, O is an oxygen atom, and C represent an organic radical, such as an aryl group, that is subject to hydrolysis under acid catalysis.

Suitable phosphorus-based ligands for the transition metal, e.g., nickel, complex, can be selected from the group consisting of bidentate and/or tridentate ligands of formula (III) and/or formula (IIIA), and monodentate ligands of formula (IV), or combinations thereof.

Bidentate and Tridentate Ligands

Bidentate and tridentate ligands can be of formulas (III) and (IIIA), respectively, thus including a bidentate phosphorus-based ligand of formula (III)

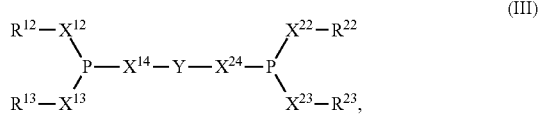

or,
a tridentate phosphorus-based ligand of formula (IIIA)

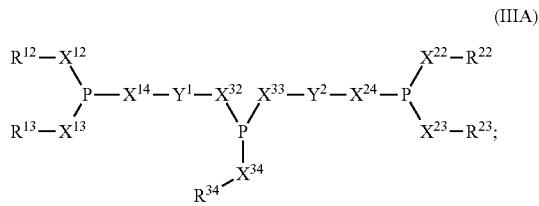

wherein for the ligand of formula (III), $X^{12}$, $X^{13}$, $X^{14}$, $X^{22}$, $X^{23}$, and $X^{24}$, each independently is oxygen or a bond, provided that at least one of $X^{12}$, $X^{13}$, $X^{14}$, $X^{22}$, $X^{23}$, or $X^{24}$ is oxygen, and for the ligand of formula (IIIA), $X^{12}$, $X^{13}$, $X^{14}$, $X^{22}$, $X^{23}$, $X^{24}$, $X^{32}$, $X^{33}$, and $X^{34}$, each independently is oxygen or a bond, provided that at least one of $X^{12}$, $X^{13}$, $X^{14}$, $X^{22}$, $X^{23}$, $X^{24}$, $X^{32}$, $X^{33}$, or $X^{34}$ is oxygen;

for the ligand of formula (III), $R^{12}$, $R^{13}$, $R^{22}$, and $R^{23}$, and for the ligand of formula (IIIA), $R^{12}$, $R^{13}$, $R^{22}$, $R^{23}$, and $R^{34}$, each independently is (C1-C10) cycloalkyl, (C3-C10)cycloalkyl(C1-C10)alkyl, (C6-C20)aryl, or (C6-C20)aryl(C1-C10)alkyl, wherein for any (C6-C20)aryl or (C6-C20)aryl(C1-C10)alkyl of $R^{12}$, $R^{13}$, $R^{22}$, $X^{23}$ or $R^{34}$, each ring thereof is unsubstituted or is substituted with 1-4 substituents independently selected from the group consisting of (C1-C10) alkyl, (C3-C10)cycloalkyl, (C1-C10)alkoxy, (C3-C10) cycloalkoxy, (C3-C10)cycloalkyl(C1-C10)alkyl, (C3-C10)cycloalkoxy(C1-C10)alkyl, (C3-C10)cycloalkyl (C1-C10)alkoxy, (C3-C10)cycloalkoxy(C1-C10) alkoxy, (C6-C20)aryl, and (C6-C20)aryl(C1-C10) alkyl; or, optionally, one or more of pairs $R^{12}$ and $R^{13}$ or $R^{22}$ and $R^{23}$ are mutually directly bonded, such that the $R^{12}X^{12}$ and $R^{13}X^{13}$ groups, or the $R^{22}X^{22}$ and $R^{23}X^{23}$ groups, or both, together with the respective phosphorus atom to which each pair of groups is bonded, forms a respective ring;

for the ligand of formula (III) the group Y, and for the ligand of formula (MA), the groups $Y^1$ and $Y^2$ independently, is an (C6-C20)arylene group, wherein each ring thereof is independently unsubstituted or is substituted with 1-4 (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl (C1-C10)alkoxy, (C3-C10)cycloalkoxy(C1-C10)alkoxy, (C6-C20)aryl, (C6-C20)aryl(C1-C10)alkyl, fluorine, chlorine, bromine, or (C1-C10)haloalkyl;

$X^{12}$, $X^{13}$, $X^{14}$, $X^{22}$, $X^{23}$, $X^{24}$, $X^{32}$, $X^{33}$, and $X^{34}$, can each be oxygen. In such a case, e.g., for formula (III) or (IIIA), the bridging group Y, $Y^1$, and/or $Y^2$ is bonded to phosphite groups. Or, $X^{12}$ and $X^{13}$ can each be oxygen and $X^{14}$ a single bond, or $X^{12}$ and $X^{13}$ each a oxygen and $X^{14}$ a single bond. And, $X^{22}$, $X^{23}$ and $X^{24}$ can each be oxygen, or $X^{22}$ and $X^{24}$ can each be oxygen and $X^{23}$ a single bond, or $X^{22}$ and $X^{23}$ can each be oxygen and $X^{24}$ a single bond, or $X^{23}$ can be oxygen and $X^{22}$ and $X^{24}$ each a single bond, and so forth. Each phosphorus atom in a compound of formula (III), (IIIA), or (IV), can be the central atom of a phosphite, phosphonite, phosphinate, phosphinite or phosphine, preferably a phosphonite or a phosphite.

At least one of the X groups of each of formulas (III), (IIIA), and (IV) is an oxygen atom, providing a P—O—C bond, wherein P is a phosphorus atom, O is an oxygen atom, and C represent an organic radical, such as an aryl group. The bridging group Y, $Y^1$, or $Y^2$ can each independently be a (C6-C20)arylene group, each ring of which is unsubstituted or is substituted with 1-4 (C1-C10)alkyl, (C3-C10) cycloalkyl, (C1-C10)alkoxy, (C3-C10)cycloalkoxy, (C1-C10)alkyl(C3-C10)cycloalkyl, (C1-C10)alkyl(C3-C10) cycloalkoxy, (C1-C10)alkoxy(C3-C10)cycloalkyl, (C1-C10)alkoxy(C3-C10)cycloalkoxy, (C6-C20)aryl, fluorine, chlorine, bromine, or (C1-C10)haloalkyl;

In particular, Y, $Y^1$, and/or $Y^2$ can, combined with the X groups to which it is bonded, be a pyrocatechol, a bis (phenol) or bis(naphthol). By an "arylene" group is meant a bifunctional group comprising one or more (C6-C20)aryl rings, which can be unsubstituted, or substituted, e.g., with (C1-C10)alkyl, (C3-C10)cycloalkyl, (C1-C10)alkyl(C3-C10)cycloalkyl, (C1-C10)alkoxyl(C3-C10)cycloalkyl, (C1-C10)alkoxyl, (C3-C10)cycloalkoxyl, (C1-C10)alkyl(C3-C10)cycloalkoxyl, and (C1-C10)alkoxyl(C3-C10) cycloalkoxyl; halogen, such as fluorine, chlorine, bromine; halogenated alkyl, such as trifluoromethyl; aryl, such as phenyl or other unsubstituted or substituted aryl groups.

In any of the ligands of formulas (III) or (IIIA), i.e., the bidentate and tridentate ligands, respectively, the R groups can be as described herein; for example, for the ligand of formula (III) or formula (IIIA), each respective $R^{12}$, $R^{13}$, $R^{22}$, $R^{23}$ or $R^{34}$ is each an independently selected (C6-C20) aryl group, wherein each ring thereof is independently unsubstituted or is substituted with 1-4 substituents independently selected from the group consisting of (C1-C10) alkyl, (C3-C10)cycloalkyl, (C1-C10)alkoxy, (C3-C10)cycloalkoxy, (C3-C10)cycloalkyl(C1-C10)alkyl, (C3-C10) cycloalkoxy(C1-C10)alkyl, (C3-C10)cycloalkyl(C1-C10) alkoxy, (C3-C10)cycloalkoxy(C1-C10)alkoxy, (C6-C20) aryl and (C6-C20)aryl(C1-C10)alkyl, or wherein any one or more pair of $R^{12}$ and $R^{13}$, or $R^{22}$ and $R^{23}$, is directly mutually bonded such that any mutually bonded pair, together with the respective $X^{12}$, $X^{13}$, $X^{22}$ or $X^{23}$ groups and the phosphorus atom to which they are bonded, forms a ring.

An example of a bidentate phosphite ligand that is useful in the present process, i.e., a compound of formula (III), above, is a ligand having formula (V), shown below (V)

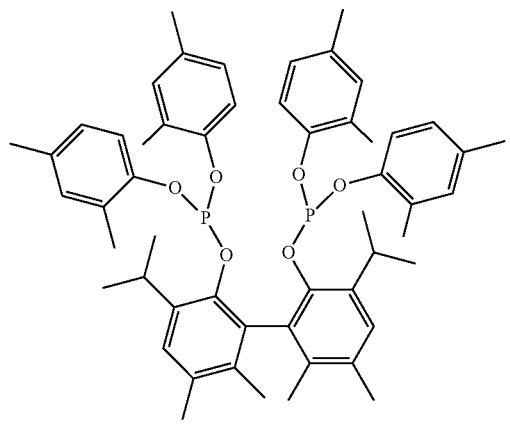

(VIII)

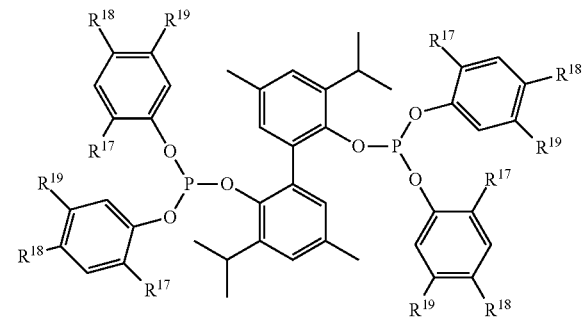

Further examples of bidentate phosphite ligands that are useful in the present process include those having the formulae (VI) to (IX), shown below wherein for each formula, $R^{17}$ can selected from the group consisting of methyl, ethyl or iso-propyl, and $R^{18}$ and $R^{19}$ can be independently selected from H or methyl. Or, each of $R^{17}$, $R^{18}$, and $R^{19}$ can be independently higher alkyls, or cycloalkyls, alkoxyls, or cycloalkoxyls (IX)

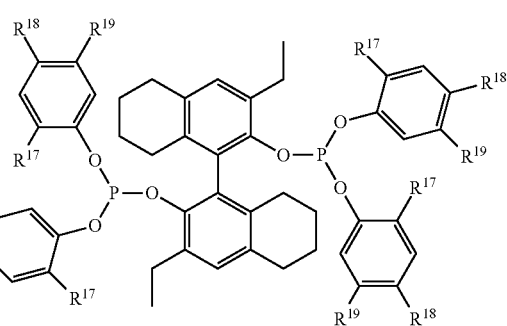

(VI)

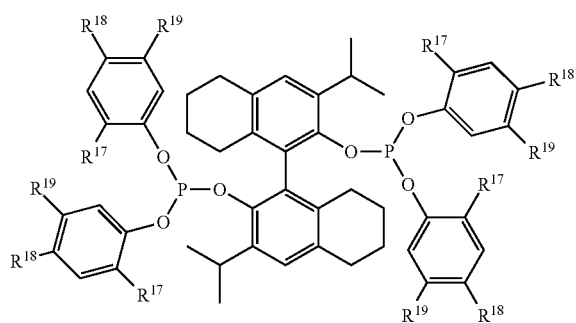

Additional examples of bidentate phosphite ligands that are useful in the present process include a ligand selected from a member of the group represented by formulae (X) and (XI), in which all like reference characters have the same meaning, except as further explicitly limited:

(X)

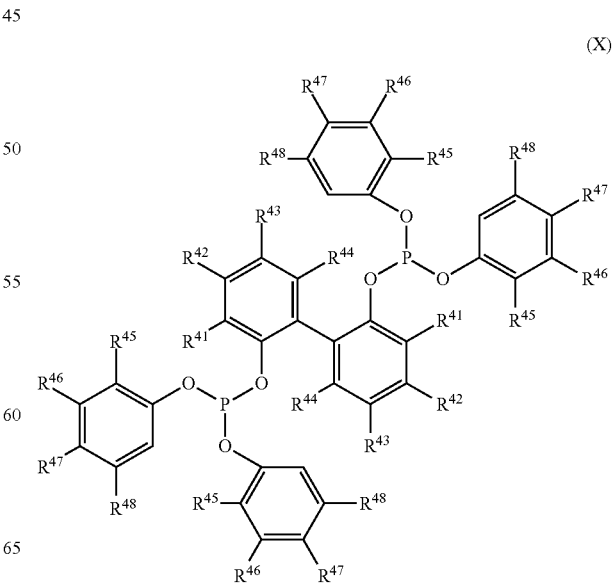

(VII)

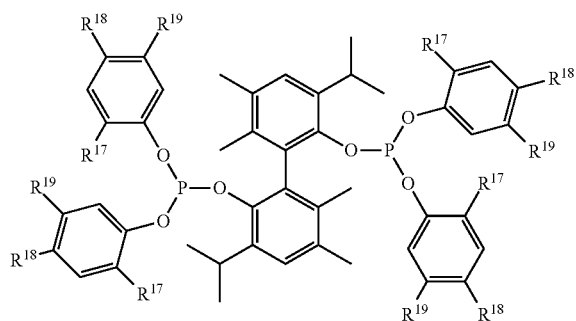

(XI)

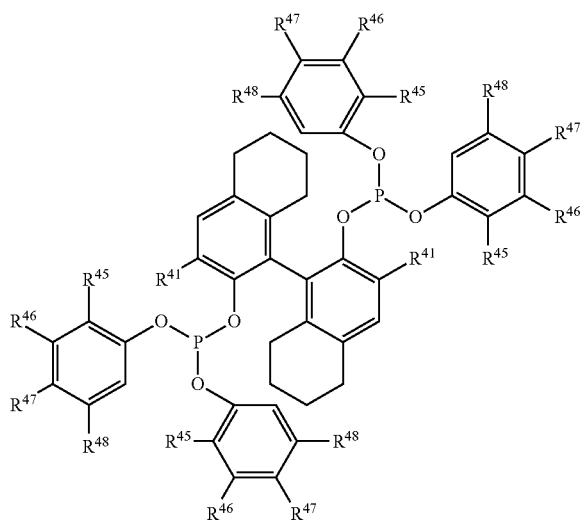

wherein, $R^{41}$ and $R^{45}$ can be independently selected from the group consisting of $C_1$-$C_{10}$ alkyl or $C_3$-$C_{10}$ cycloalkyl, $C_1$-$C_{10}$ alkoxyl, or $C_3$-$C_{10}$ cycloalkoxyl and each of $R^{42}$, $R^{43}$, $R^{44}$, $R^{46}$, $R^{47}$ and $R^{48}$ is independently selected from the group consisting of H and $C_1$-$C_{10}$ alkyl or $C_3$-$C_{10}$ cycloalkyl.

For example, the bidentate phosphite ligand can be selected from a member of the group represented by formula (X) and formula (XI), wherein $R^{41}$ is methyl, ethyl, isopropyl or cyclopentyl;
$R^{42}$ is H or methyl;
$R^{43}$ is H or a C1-C10 alkyl or C3-C10 cycloalkyl, or C1-C10 alkoxyl or C3-C10 cycloalkoxyl;
$R^{44}$ is H or methyl;
$R^{45}$ is methyl, ethyl or isopropyl; and
$R^{46}$, $R^{47}$ and $R^{48}$ are independently selected from the group consisting of H and C1-C10 alkyl or C3-C10 cycloalkyl, or C1-C10 alkoxyl or C3-C10 cycloalkoxyl.

As additional examples, the bidentate phosphite ligand can be selected from a member of the group represented by formula (X), wherein $R^{41}$, $R^{44}$, and $R^{45}$ are methyl;
$R^{42}$, $R^{46}$, $R^{47}$ and $R^{48}$ are H; and
$R^{43}$ is a C1-C10 alkyl or C3-C10 cycloalkyl, or C1-C10 alkoxyl or C3-C10 cycloalkoxyl;
or
$R^{41}$ is isopropyl;
$R^{42}$ is H;
$R^{43}$ is a C1-C10 alkyl or C3-C1 cycloalkyl, or C1-C10 alkoxyl or C3-C10 cycloalkoxyl;
$R^{44}$ is H or methyl;
$R^{45}$ is methyl or ethyl;
$R^{46}$ and $R^{48}$ are H or methyl; and
$R^{47}$ is H, methyl or tertiary-butyl;
or the bidentate phosphite ligand can be selected from a member of the group represented by formula XI, wherein
$R^{41}$ is isopropyl or cyclopentyl;
$R^{45}$ is methyl or isopropyl; and
$R^{46}$, $R^{47}$, and $R^{48}$ are H.

As yet another example, the bidentate phosphite ligand can be represented by Formula (X), wherein $R^{41}$ is isopropyl; $R^{42}$, $R^{46}$, and $R^{48}$ are H; and $R^{43}$, $R^{44}$, $R^{45}$, and $R^{47}$ are methyl.

As another example, the ligand of formula (III) can be of formula (XII)

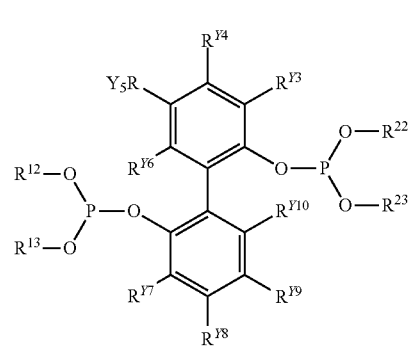

wherein $R^{12}$, $R^{13}$, $R^{22}$ and $R^{23}$ are each independently an unsubstituted or a substituted monovalent aryl, and each of $R^{Y3}$-$R^{Y10}$ is independently selected from the group consisting of hydrogen, (C1-C10) alkyl, and (C1-C10)alkoxy, or wherein two adjacent $R^{Y3}$-$R^{Y10}$ groups together form an optionally substituted fused aryl ring.

More specifically, for example, for a ligand of formula (XII), $R^{12}$, $R^{13}$, $R^{22}$, and $R^{23}$ are each independently phenyl substituted at a respective single ortho-position with a (C1-C10)alkyl or (C1-C10)alkoxy, wherein respective meta- and para-positions of the $R^{12}$, $R^{13}$, $R^{22}$, and $R^{23}$ phenyls can each independently be unsubstituted or be independently substituted with (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, or (C3-C10)cycloalkoxy(C1-C10)alkoxy;

$R^{Y6}$ and $R^{Y10}$ are independently (C1-C10)alkyl or (C1-C10)alkoxy, and $R^{Y3}$, $R^{Y4}$, $R^{Y5}$, $R^{Y7}$, $R^{Y8}$, and $R^9$, are independently H, (C1-C10)alkyl, or (C1-C10)alkoxy, provided that at least one of $R^{Y3}$, $R^{Y4}$, or $R^{Y5}$, and at least one of $R^{Y7}$, $R^{Y8}$, or $R^{Y9}$, is (C1-C10)alkyl or (C1-C10)alkoxy.

It will be recognized that Formulae (V) to (XII) are two-dimensional representations of three-dimensional molecules and that rotation about chemical bonds can occur in the molecules to give configurations differing from those shown. For example, rotation about the carbon-carbon bond between the 2- and 2'-positions of the biphenyl, octahydrobinaphthyl, and or binaphthyl bridging groups of Formulae (V) to (XII), respectively, can bring the two phosphorus atoms of each Formula in closer proximity to one another and can allow the phosphite ligand to bind to nickel in a bidentate fashion. In addition, use of an optically active moiety such as sec-butyl for $R^{41}$ can result in optically active catalysts.

Monodentate Ligands

The monodentate ligand can be of formula (IV)

$$P(X^1R^1)(X^2R^2)(X^3R^3) \qquad (IV)$$

wherein $X^1$, $X^2$ and $X^3$ are each independently oxygen or a single bond, provided that at least one of $X^1$, $X^2$, or $X^3$ is an oxygen; and $R^1$, $R^2$ and $R^3$ is each independently (C1-C10)alkyl, (C3-C10)cycloalkyl, (C3-C10)cycloalkyl(C1-C10)alkyl, (C6-C20)aryl, or (C6-C20)aryl(C1-C10)alkyl, wherein for any (C6-C20)aryl or (C6-C20)aryl(C1-C10) alkyl of $R^1$, $R^2$, or $R^3$ each ring thereof is independently unsubstituted or is substituted with 1-4 substituents independently selected from the group consisting of (C1-C10) alkyl, (C3-C10)cycloalkyl, (C1-C10)alkoxy, (C3-C10)cycloalkoxy, (C3-C10)cycloalkyl(C1-C10)alkyl, (C3-C10) cycloalkoxy(C1-C10)alkyl, (C3-C10)cycloalkyl(C1-C10) alkoxy, (C3-C10)cycloalkoxy(C1-C10)alkoxy, (C6-C20) aryl, and (C6-C20)aryl(C1-C10)alkyl; or, optionally, any two of $R^1$, $R^2$, or $R^3$ are directly bonded to each other such that any pair of $R^1X^1$, $R^2X^2$, and $R^3X^3$ groups, together with the phosphorus atom to which they are bonded, forms a ring; The ligand of formula (IV) can be a phosphite, a phosphonite, a phosphinite, and the like, provided that at least one phosphite ester bond, e.g., a P—O—C bond, subject to acid-catalyzed hydrolysis, is present in the ligand.

$R^1$, $R^2$ and $R^3$ can independently alkyl, cycloalkyl, alkoxy, or cycloalkyoxy radicals, the alkyl radicals preferably having from 1 to 10 carbon atoms, such as methyl, ethyl, n-propyl, propyl, n-butyl, i-butyl, s-butyl, t-butyl, and the cycloalkyl radical preferably having from 3 to 10 carbon atoms, such as cyclopropyl, cyclobutyl, cyclpentyl, and cyclohexyl; aryl groups such as phenyl, o-tolyl, m-tolyl, p-tolyl, 1-naphthyl, or 2-naphthyl, preferably having from 6 to 20 carbon atoms, such as 1,1'-biphenyl, 1,1'-binaphthyl. The $R^1$, $R^2$ and $R^3$ groups can be bonded together directly, i.e. not solely via the central phosphorus atom. $R^1$, $R^2$ and $R^3$ groups can be selected from the group consisting of phenyl, o-tolyl, m-tolyl and p-tolyl. A maximum of two of the $R^1$, $R^2$ and $R^3$ groups can be phenyl groups. Or, maximum of two of the $R^1$, $R^2$ and $R^3$ groups can be o-tolyl groups.

Particular compounds which can be used are those of the formula (IVa) below:

(o-tolyl-O-)$_w$(m-tolyl-O-)$_x$(p-tolyl-O-)$_y$(phenyl-O-)$_z$P   Formula (IVA)

where w, x, y, z are each a natural number and the following conditions apply: w+x+y+z=3 and z=less than or equal to 2. Examples of such compounds (IVa) include: (o-tolyl-O—)$_3$ P, (p-tolyl-O-)(phenyl-O—)$_2$P, (m-tolyl-O-)(phenyl-O—)$_2$P, (o-tolyl-O-)(phenyl-O—)$_2$P, (p-tolyl-O-)$_2$(phenyl-O—)P, (m-tolyl-O-)$_2$(phenyl-O—)P, (o-tolyl-O-)$_2$(phenyl-O—)P, (m-tolyl-O-)(p-tolyl-O-)(phenyl-O—)P, (o-tolyl-O-)(p-tolyl-O-)(phenyl-O—)P, (o-tolyl-O-)(m-tolyl-O-)(phenyl-O—)P, (p-tolyl-O—)$_3$P, (m-tolyl-O-)(p-tolyl-O—)$_2$P, (o-tolyl-O-)(p-tolyl-O—)$_2$P, (m-tolyl-O-)$_2$(p-tolyl-O—)P, (o-tolyl-O-)$_2$(p-tolyl-O—)P, (o-tolyl-O-)(m-tolyl-O-)(p-tolyl-O—)P, (m-tolyl-O—)$_3$P, (o-tolyl-O-)(m-tolyl-O—)$_2$P, (o-tolyl-O-)$_2$(m-tolyl-O—)P or mixtures of such compounds.

Ligands of formula (IVA) can be characterized as a compound of formula

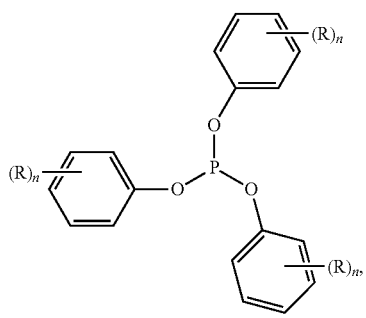

wherein each R is independently methyl and each n is independently 0, 1, or 2. Mixtures of such compounds of formula (IVA) can be used as monodentate ligands in processes of the invention.

Monodentate ligands useful for practicing a process of the invention include phosphite triesters of the following formulae (XIII) and (XIV):

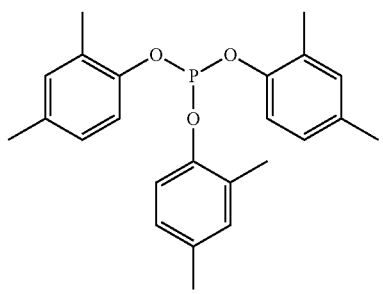

(XIII)

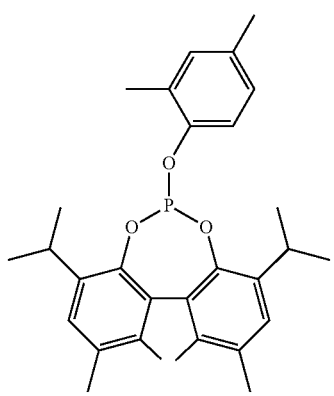

(XIV)

The processes and reaction mixtures of the present invention are stabilized by utilization of one or more of the monodentate ligands, particularly those which are produced as a byproduct of the synthesis of the bidentate or tridentate phosphorus-based ligands for the nickel complex used as a catalyst in the hydrocyanation reaction. In particular, one or more monodentate ligands, byproducts of a synthetic process used to prepare the bidentate and/or tridentate ligands, can have a hydrolysis rate greater than the phosphorus-based bidentate and/or tridentate ligand which is the synthetic product. For example, the byproduct monodentate ligand can have a hydrolysis rate at least about 1.5 or 2.0 times greater than the hydrolysis rate of the target product bidentate or tridentate ligand, such that when the mixture is subjected to hydrolytic conditions in the hydrocyanation reaction milieu, hydrolysis of the monodentate ligand byproduct can occur more rapidly than hydrolysis of the target product bidentate or tridentate ligand. This can serve to scavenge water present in the reaction milieu, and thereby diminish the amount of hydrolysis of the bidentate (formula (III)) or tridentate (formula (IIIA)) ligand that occurs, relative to an amount of hydrolysis of these ligands that would occur in the absence of the monodentate ligand of formula (IV). Specific examples of a set of a bidentate ligand and associated monodentate ligands produced as synthetic byproducts in the formation of the bidentate ligand, that can serve to protect the bidentate ligand from hydrolysis, include as the bidentate ligand a ligand of formula (V)

(V)

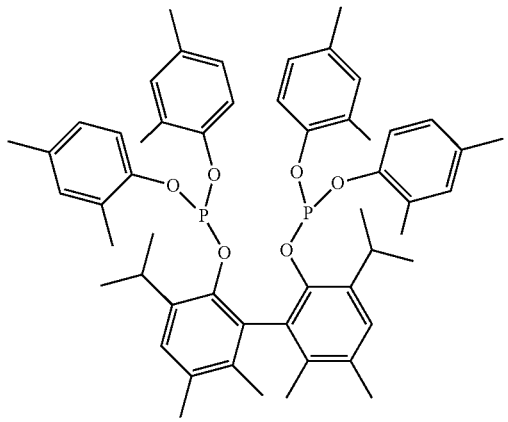

and the monodentate ligands of formulas (XIII) and (XIV):

(XIII)

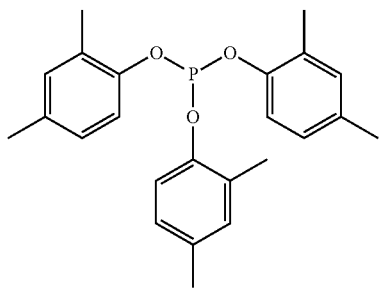

(XIV)

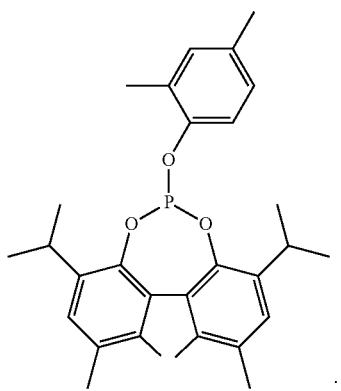

As can be seen, various phosphite exchange reactions and side reactions in formation of the bidentate phosphite ester of formula (V) can yield as byproducts the monodentate phosphite esters of formulas (XIII) and (XIV). Exchange at the phosphite center of the 2,4-xylyl groups and the substituted binaphthyl group can give rise to these structures from the precursors used in synthesis of (V), or from (V) itself.

The amount or proportion of monodentate ligands used in the hydrocyanation reaction milieu and relative to the bidentate and/or tridentate ligards will vary depending on the particular relative hydrolysis rates and reaction parameters chosen. Particularly, the amount of stabilizing monodentate ligand will be such as to make a quantifiable difference in the activity or useful life of the phosphorus-based bidentate and/or tridentate ligand in the particular hydrocyanation reaction. For example, the a molar ratio of the monodentate ligand of formula (XIII) or formula (XIV) or formula (IVA) admixed to the bidentate ligand of formula (III) can be at least 0.01, and can range up to 2.

Lewis Acid Promoter

A reaction for hydrocyanating 3-pentenenitrile to produce adiponitrile preferably takes place in the presence of a promoter for promoting this reaction. The promoter can be a Lewis acid, such as an inorganic compound, an organometallic compound, or combinations thereof, in which a cation of the Lewis acid is selected from the group consisting of scandium, titanium, vanadium, chromium, manganese, iron, cobalt, copper, zinc, boron, aluminum, yttrium, zirconium, niobium, molybdenum, cadmium, rhenium, lanthanum, erbium, ytterbium, samarium, tantalum, and tin. However, the reactions, which take place in the first reaction zone for hydrocyanating 1,3-butadiene and the second reaction zone for isomerizing 2-methyl-3-butenenitrile, preferably take place in the absence or substantial absence of such a promoter.

Dinitriles can be produced in the first reaction zone by the reaction of 3-pentenenitrile (3PN) or 2-methyl-3-butenenitrile (2M3BN) with HCN. Lewis acids are capable of promoting the formation of dinitriles in the first reaction zone. Lewis acids are preferably not introduced into the first reaction zone in detectable amounts. However, a detectable amount of a Lewis acid can be introduced into the first reaction zone, provided that dinitrile formation is minimized. For example, a detectable amount of a Lewis acid can be introduced into the first reaction zone, provided that the amount of dinitriles produced, when none of the Lewis acid is introduced into the first reaction zone, is not increased by more than 5 wt %.

Lewis acid can be unintentionally introduced into the first reaction zone as a result of a unit upset or operator error. However, the continuous production of 3-pentenenitrile can be maintained, provided that the ratio of atomic equivalents of Ni to moles of Lewis Acid in the first reaction zone is less than 10:1 during the course of at least 95% of the production of 3-pentenenitrile.

3-pentenenitrile produced in the first and second reaction zones can be reacted with hydrogen cyanide to produce dinitriles comprising adiponitrile in a third reaction zone downstream of the first and second reaction zones. A catalyst and a Lewis acid promoter can flow through the third reaction zone along with reactants and products. Preferably, none of the Lewis acid promoter which flows from the third reaction zone flows into the first reaction zone. However, it is possible that a portion of the Lewis acid promoter which flows from the third reaction zone flows into the first reaction zone, provided that the unwanted production of dinitriles in the first reaction is minimized, as discussed above.

EXAMPLES

Example 1

Synthesis of Monodentate Ligand of Formula (XIII)

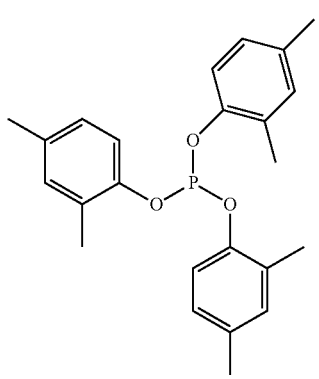

(XIII)

A 250 mL round bottom flask was equipped with a stirbar and a condenser under nitrogen atmosphere. The reaction flask was vented through the top of the condenser to an absorber system containing an aqueous sodium hydroxide solution used to absorb the by-product HCl from the reaction. Note that the absorber system should contain an appropriate safety design, such as an intermediate trap, to prevent the direct contact of the reactor contents with the absorber solution. The reaction produces three molar equivalents of by-product HCl which was passed through the absorber solution containing 10% molar excess of sodium hydroxide. The reaction flask was charged with 2,4-dimethylphenol (36.6 g, 0.3 mol) and PCl3 (13.7 g, 0.1 mol). The mixture was stirred at room temperature for one hour then slowly heated to 100° C. for a few hours until no more gas was evolved and only a single peak was observed by $^{31}$P NMR (132 ppm). The residue was then purified by high-vacuum distillation. The product was distilled at a head temperature of approx. 190° C. at 1 mm Hg. The clear and sticky product was collected to give a 90% yield (35 g). The product purity was over 99% by 31 P NMR (Tol-D8): 132.6 ppm; LC/MS: m/z=395 (M+H)+

Example 2

Synthesis of Monodentate Ligand of Formula (XIV)

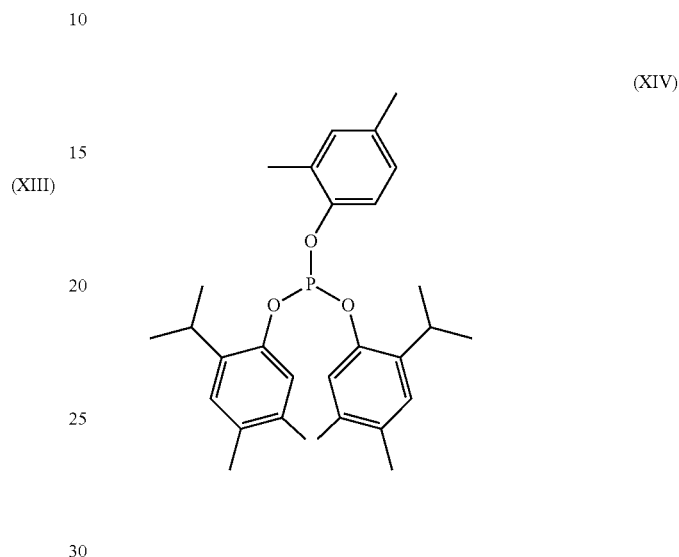

(XIV)

The compound of formula (XIV) was prepared by first reacting the compound of formula (V) with phosphorus trichloride to form the corresponding phosphorochloridite followed by its reaction with 2,4-dimethylphenol. For both reaction steps, the HCl offgas was scrubbed with the absorber described in Example 1. After cooling to room temperature, a solid precipitated and was filtered out as a white powder. mp. 140-142° C.; P NMR (Tol-D8): 135.9 ppm; LC/MS: m/z=477 (M+H).

Example 3

Determination of the Relative Hydrolysis Rates of Formulas (V), (XIII) and (XIV)

Formula (V)=1.0
Formula (XIII)=1.8
Formula (XIV)=2.5

This result means that the monodentate ligands (XIII) and (XIV), entering the hydrocyanation process either as byproducts of ligand synthesis of bidentate ligand (V), or by intentional addition by the operator, will consume a disproportionate share of the water in process streams and thereby lower the formula (V) QPU or the QPU of other ligands, wherein QPU is defined as Quantity Per Unit of product, i.e., the quantity of the ligand of formula (V) consumed in grams per kilogram of adiponitrile produced.

Example 4

Synthesis of the Monodentate Ligand of Formula (IVA):

The compound of formula (IVA) is of formula

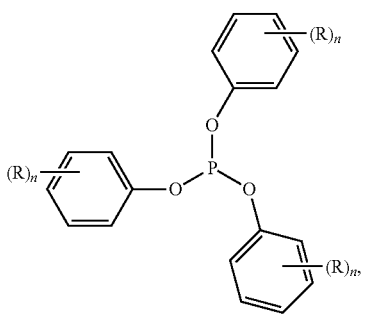

wherein each R is methyl, and each n is independently 0, 1, or 2.

A 250 mL round bottom flask was equipped with a stirbar and a condenser under nitrogen atmosphere. The reaction flask was vented through the top of the condenser to an absorber system containing an aqueous sodium hydroxide solution used to absorb the byproduct HCl from the reaction. Note that the absorber system should contain an appropriate safety design, such as an intermediate trap, to prevent the direct contact of the reactor contents with the absorber solution. The reaction produces three molar equivalents of by-product HCl which was passed through the absorber solution containing 10% molar excess of sodium hydroxide. The reaction flask was charged with a mixture of phenol (12 g, 0.13 mol), meta-cresol (37.4 g, 0.35 mol), para-cresol (30.6 g, 0.28 mol) and PCl3 (34.6 g, 0.25 mol). The mixture was stirred at room temperature for one hour then slowly heated to 120° C. for a few hours until no more gas was evolved and the chlorine content was below 100 ppm by X-ray fluorescence spectroscopy.

The residue was then purified by high-vacuum distillation. The product was distilled at a head temperature of approx. 190° C. at 1 mm Hg. The viscous, clear product was collected to give approximately a 90% yield (80 g). The product purity was over 99% by $^{31}$P NMR (Tol-D8): 100-120 ppm.

Example 5

Hydrolysis of a Reaction Mixture Resulting from the Catalytic Hydrocyanation of Butadiene in the Preparation of Adiponitrile in the Presence of a Bidentate Ligand of Formula (V), Wherein the Monodentate Ligands of Formula (XIII) and Formula (XIV) are Present in the Mixture.

Figure 2:
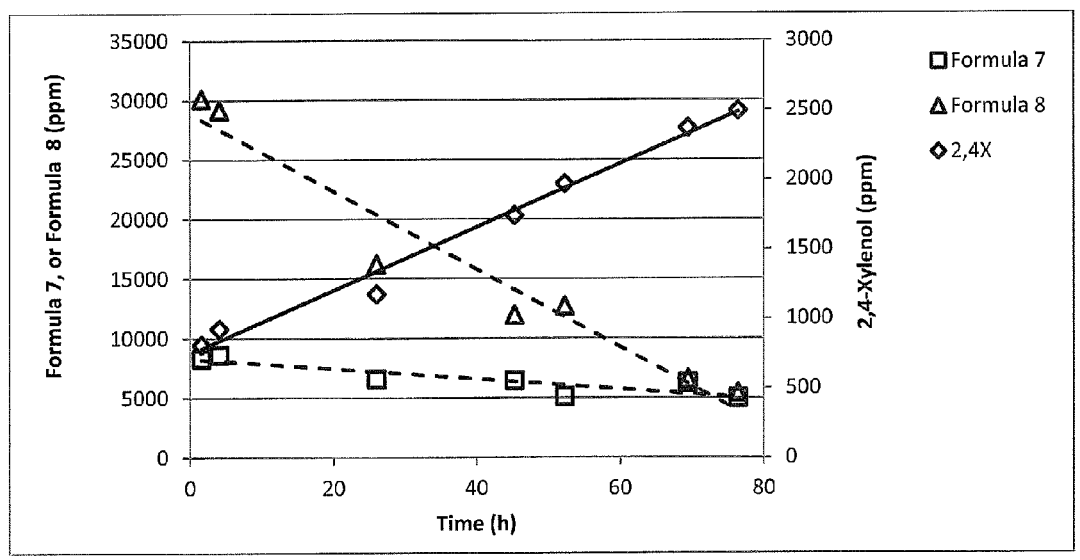
FIG. 2 shows the results of hydrolysis of a reaction mixture resulting from the catalytic hydrocyanation of butadiene in the preparation of adiponitrile in the presence of monophosphites of formulas (XIII) and (XIV).

The experiment was conducted in a 10 mL, thick-walled, conical Reacti-Vial™ using a temperature-regulated Reacti-Block™ aluminum heating block enclosed in a nitrogen purge box. Mixing was accomplished using a triangular magnetic stir bar. The Reacti-Vial™ is charged with a solution of the ligand of formula (V)—Nickel complex in pentenenitriles in which the ligands of formula (XIII) and formula (XIV) are also present, inside a glove-box and then with water by micro-syringe once transferred to the heating block at the beginning of the experiment. The initial water concentration was 2500 ppm and the Reacti-Block™ was maintained at 80° C. Samples were then removed at the desired intervals for analysis by HPLC. At the conclusion of the studies, $^{31}$P NMR was also obtained on selected samples. See FIGS. 1, 2 and Table 1 for analytical results data.

Comparative Example A

Figure 3:
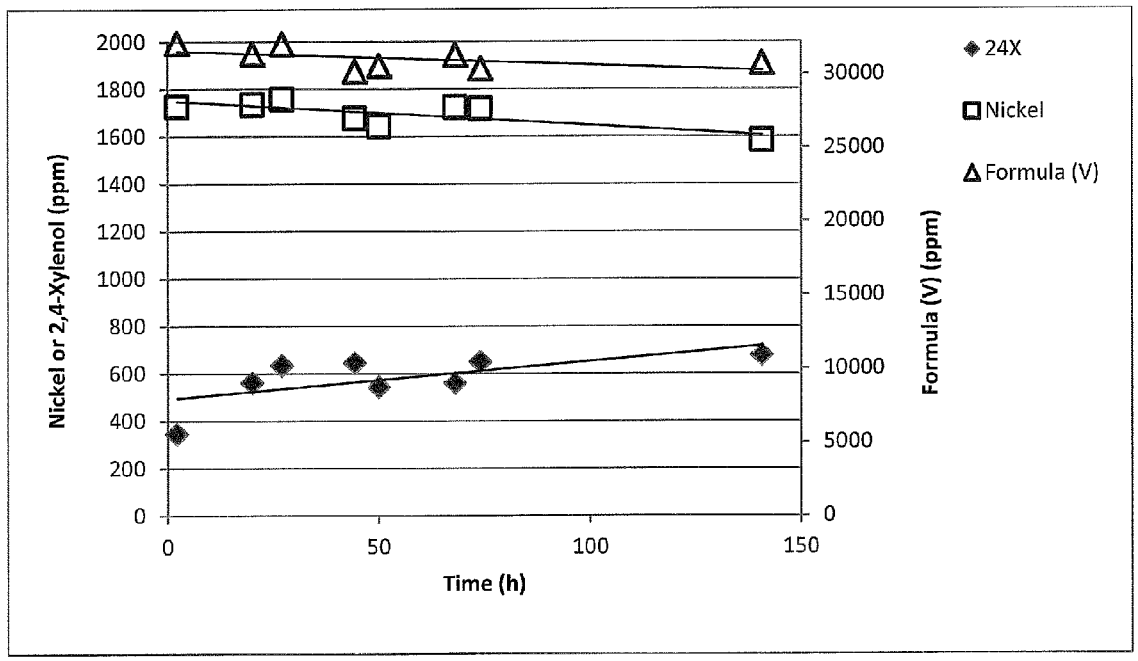
FIG. 3 shows the results of hydrolysis of a reaction mixture resulting from the catalytic hydrocyanation of butadiene in the preparation of adiponitrile containing the ligand of Formula (V) substantially free of other phosphites.

Hydrolysis of a Reaction Mixture Resulting from the Catalytic Hydrocyanation of Butadiene in the Preparation of Adiponitrile in the Presence of a Ligand of Formula (V):

The experiment was conducted in a 10 mL, thick-walled, conical Reacti-Vial™ using a temperature-regulated Reacti-Block™ aluminum heating block. Mixing was accomplished using a triangular magnetic stir bar. The heating block was enclosed in a nitrogen purge box. The Reacti-Vial™ was charged with a solution of the ligand of formula (V)—Nickel complex in pentenenitriles, inside a glove-box and then with water by micro-syringe once transferred to the heating block at the beginning of the experiment. The initial water concentration was 2500 ppm and the Reacti-Block™ was maintained at 80° C. Samples were then removed at the desired intervals for analysis by HPLC. At the conclusion of the studies, $^{31}$P NMR was also obtained on selected samples. The data obtained from this comparative example are presented in FIG. 3, and show that in the absence of added monophosphites the ligand of formula (V), is more susceptible to hydrolysis as evidenced by the increased rates of disappearance of Formula (V) and nickel (relative to Example 5), and the generation of 2,4-Xylenol (which, in this test, could only be formed from Formula (V)). See FIG. 3 and Table 1 for analytical results data.

Example 6

Hydrolysis of a Reaction Mixture Resulting from the Catalytic Hydrocyanation of Butadiene in the Preparation of Adiponitrile in the Presence of a Ligand Compound of Formula (V), Wherein the Ligand Compounds Formula (IVA) are Admixed:

Replicate Comparative Example A, but admix the reaction mixture containing the ligand of Formula (V) (5 g) with the ligand mixture of Formula (IVA) (0.05 g), as prepared in Example 4.

Figure 4:
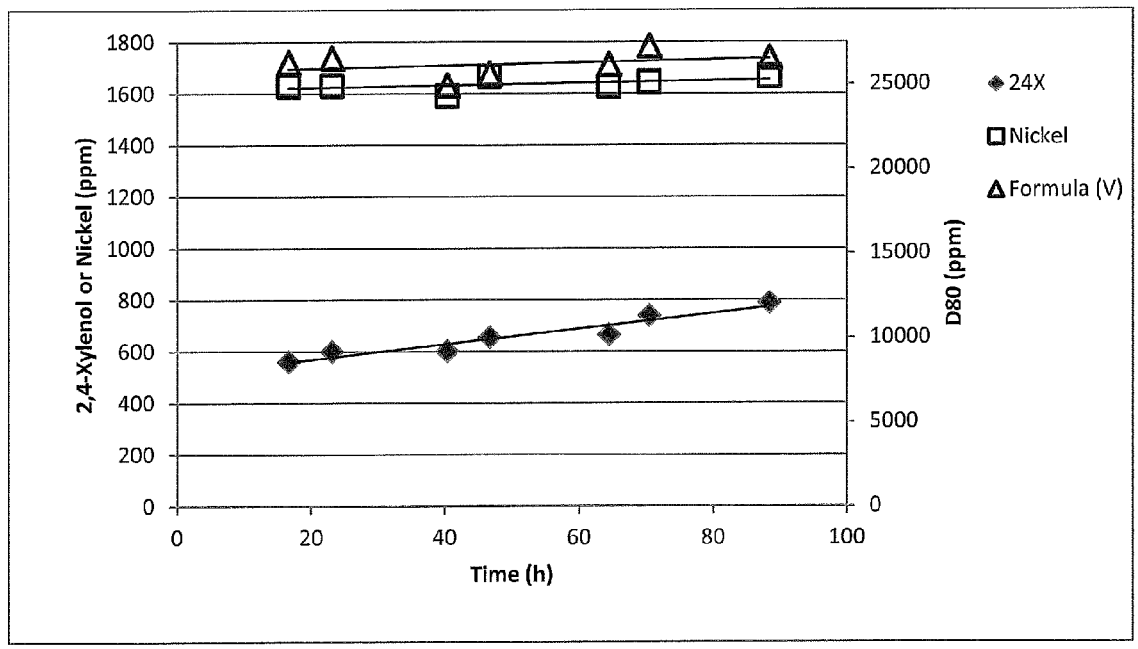
FIG. 4 shows the results of hydrolysis of a reaction mixture resulting from the catalytic hydrocyanation of butadiene in the preparation of adiponitrile in the presence of approximately 1% (wt.) phosphites of Formula (IVA).

The data obtained from Example 6 shows that when monodentates ligand mixture of the formula (IVA) is admixed, that the ligand of formula (V) is protected against hydrolysis as the ligands of formula (IVA) are instead sacrificially hydrolyzed. This is evidenced by the decreased rate of disappearance of Formula (V), and nickel (relative to Comparative Example A), and the decreased rate of generation of 2,4-Xylenol (which, in this test, could only be formed from formula (V)), and the generation of phenol (which could only be formed via the hydrolysis of the ligands of formula (IVA). See FIG. 4 and Table 1 for analytical results data.

Comparative Example B

Figure 5:
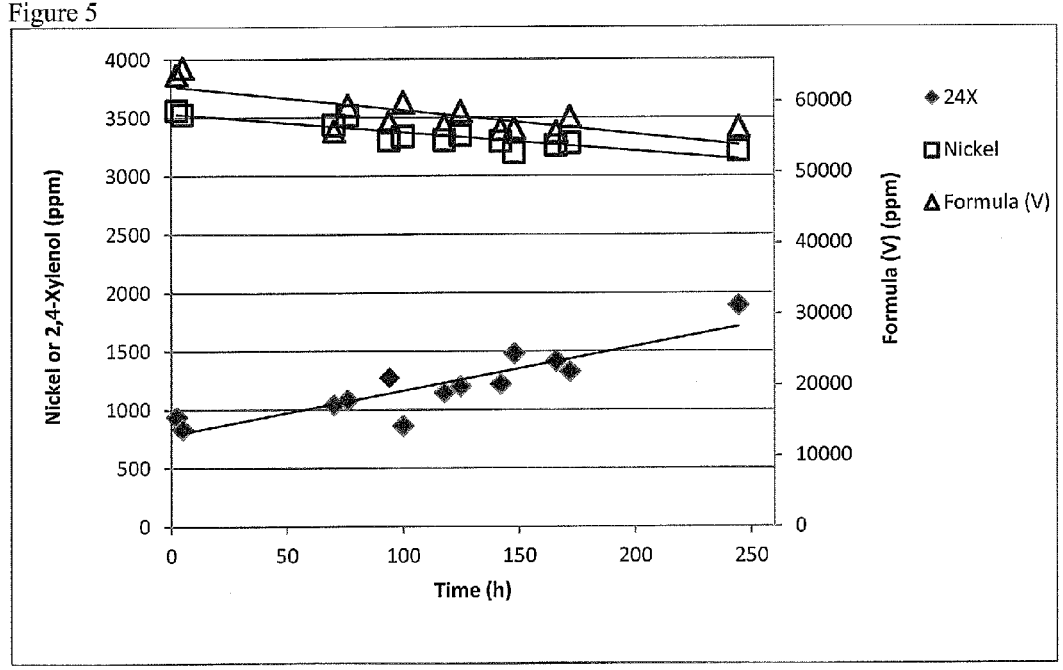
FIG. 5 shows the results of hydrolysis of a reaction mixture resulting from the catalytic hydrocyanation of butadiene in the preparation of adiponitrile containing the ligand of Formula (V) substantially free of other phosphites.

Hydrolysis of a Reaction Mixture Resulting from the Catalytic Hydrocyanation of Butadiene in the Preparation of Adiponitrile in the Presence of a Ligand Compound of Formula (V):

Replicate Comparative Example A, but use a more concentrated sample of the Formula (V)—nickel catalyst. See FIG. 5 and Table 1 for analytical results data.

TABLE 1

Rates of hydrolysis for free phosphites and
generation of 2,4-xylenol (ppm$_{(w)}$/h).

| Ex/CEx | Nickel | Formula (V)† | Formula 7 | Formula 8 | 2,4-Xylenol | Phenol‡ |
|--------|--------|--------------|-----------|-----------|-------------|---------|
| 5      | −0.1   | −4.3         | −42.3     | −326.6    | 22.7        |         |
| A      | −1.0   | −9.8         |           |           | 1.6         |         |
| 6      | 0.0    | −3.5         |           |           | 1.8         | 14.3    |
| B      | −1.6   | −33.8        |           |           | 3.8         |         |

†This is the rate of disappearance for the total amount of Formula (V) present, which is in excess to nickel (molar ratio Ni/Formula (V) = 0.8).
‡Phenol is formed via the hydrolysis of the ligand of Formula (IVa).

The data presented in Table 1 show that addition of monodentate ligands of formulas (XIII), (XIV), and (IVa) protect the bidentate ligand of formula (V) in a reaction mixture resulting from the catalytic hydrocyanation of butadiene in the preparation of adiponitrile against hydrolysis, as evidenced by the the decreased rate of disappearance of formula (V), and nickel (relative to the Comparative Examples), the increased rates of generation of 2,4-Xylenol (showing that the ligands of formulas (XIII) and (XIV) are preferentially hydrolyzed), the large consumption of the ligands of formulas (XIII) and (XIV) (in Example 5), and the generation of phenol in Example 6 (which could only be formed via the hydrolysis of the ligands of Formula (IVA).

Statements of the Invention

1. A process for stabilizing a phosphorus-based bidentate ligand of formula (III) or tridentate ligand of formula (IIIA) or a mixture thereof, in a hydrocyanation reaction milieu comprising water, the ligands having respective formulas:

a bidentate phosphorus-based ligand of formula (III)

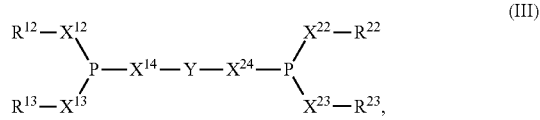

(III)

or,
    a tridentate phosphorus-based ligand of formula (IIIA)

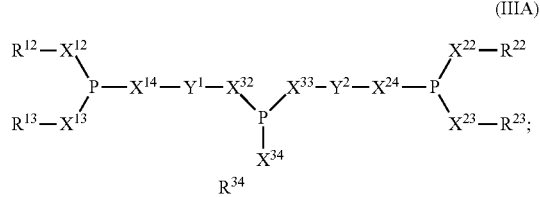

(IIIA)

wherein for the ligand of formula (III), $X^{12}$, $X^{13}$, $X^{14}$, $X^{22}$, $X^{23}$, and $X^{24}$, each independently is oxygen or a bond, provided that at least one of $X^{12}$, $X^{13}$, $X^{14}$, $X^{22}$, $X^{23}$, or $X^{24}$ is oxygen, and for the ligand of formula (IIIA), $X^{12}$, $X^{13}$, $X^{14}$, $X^{22}$, $X^{23}$, $X^{24}$, $X^{32}$, $X^{33}$, and $X^{34}$, each independently is oxygen or a bond, provided that at least one of $X^{12}$, $X^{13}$, $X^{14}$, $X^{22}$, $X^{23}$, $X^{24}$, $X^{32}$, $X^{33}$, or $X^{34}$ is oxygen;

for the ligand of formula (III), $R^{12}$, $R^{13}$, $R^{22}$, and $R^{23}$, and for the ligand of formula (IIIA), $R^{12}$, $R^{13}$, $R^{22}$, $R^{23}$, and $R^{34}$, each independently is (C1-C10)alkyl, (C3-C10)cycloalkyl, (C3-C10)cycloalkyl(C1-C10)alkyl, (C6-C20)aryl, or (C6-C20)aryl(C1-C10)alkyl, wherein for any (C6-C20)aryl or (C6-C20)aryl(C1-C10)alkyl of $R^{12}$, $R^{13}$, $R^{22}$, $R^{23}$, or $R^{34}$, each ring thereof is unsubstituted or is substituted with 1-4 substituents independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, and (C6-C20)aryl(C1-C10)alkyl; or, optionally, one or more of pairs $R^{12}$ and $R^{13}$ or $R^{22}$ and $R^{23}$ are mutually directly bonded, such that the $R^{12}X^{12}$ and $R^{13}X^{13}$ groups, or the $R^{22}X^{22}$ and $R^{23}X^{23}$ groups, or both, together with the respective phosphorus atom to which each pair of groups is bonded, forms a respective ring;

for the ligand of formula (III) the group Y, and for the ligand of formula (IIIA), the groups $Y^1$ and $Y^2$ independently, is an (C6-C20)arylene group, wherein each ring thereof is independently unsubstituted or is substituted with 1-4 (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, (C6-C20)aryl(C1-C10)alkyl, fluorine, chlorine, bromine, or (C1-C10)haloalkyl;

the process comprising admixing with the bidentate and/or the tridentate ligand a stabilizing amount of one or more monodentate phosphorus-based ligand of formula (IV)

$P(X^1R^1)(X^2R^2)(X^3R^3)$     (IV)

wherein $X^1$, $X^2$ and $X^3$ are each independently oxygen or a single bond, provided that at least one of $X^1$, $X^2$, or $X^3$ is an oxygen; and $R^1$, $R^2$ and $R^3$ is each independently (C1-C10)alkyl, (C3-C10)cycloalkyl, (C3-C10)cycloalkyl(C1-C10)alkyl, (C6-C20)aryl, or (C6-C20)aryl(C1-C10)alkyl, wherein for any (C6-C20)aryl or (C6-C20)aryl(C1-C10) alkyl of $R^1$, $R^2$, or $R^3$ each ring thereof is independently unsubstituted or is substituted with 1-4 substituents independently selected from the group consisting of (C1-C10) alkyl, (C3-C10)cycloalkyl, (C1-C10)alkoxy, (C3-C10)cycloalkoxy, (C3-C10)cycloalkyl(C1-C10)alkyl, (C3-C10) cycloalkoxy(C1-C10)alkyl, (C3-C10)cycloalkyl(C1-C10) alkoxy, (C3-C10)cycloalkoxy(C1-C10)alkoxy, (C6-C20) aryl, and (C6-C20)aryl(C1-C10)alkyl; or, optionally, any two of $R^1$, $R^2$, or $R^3$ are directly bonded to each other such that any pair of $R^1X^1$, $R^2X^2$, and $R^3X^3$ groups, together with the phosphorus atom to which they are bonded, forms a ring;

wherein the monodentate ligand of formula (IV) has a rate of hydrolysis greater than a rate of hydrolysis of a bidentate ligand of formula (III) or a tridentate ligand of formula (IIIA) or a mixture thereof, in the presence of water in a hydrocyanation reaction milieu optionally further comprising an organic component, under conditions of concentration, temperature, and time sufficient to bring about hydrolysis of the monodentate ligand of formula (IV).

2. The process of statement 1, wherein the one or more monodentate ligand of formula (IV) is produced as a byproduct in a synthetic process for the production of the bidentate ligand of Formula (III) or the tridentate ligand of formula (IIIA) or both.

3. The process of any one of statements 1-2 wherein the monodentate ligand of formula (IV) is a ligand of formula (XIII):

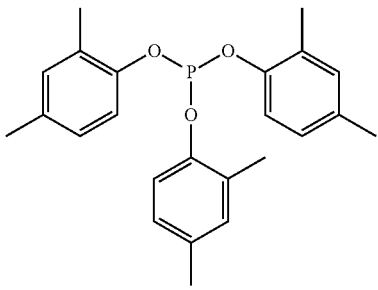

(XIII)

or a ligand of formula (XIV):

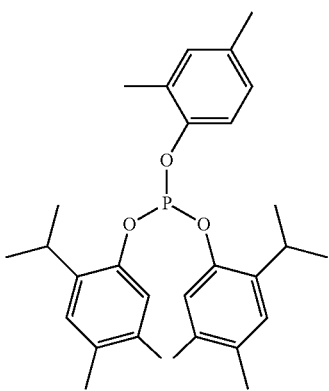

(XIV)

or is a mixture thereof.

4. The process of any one of statements 1-3, wherein a molar ratio of the ligand of formula (IV) that is admixed to the ligand of formula (III) or formula (IIIA) or mixture thereof, is at least 0.01, and, optionally, is no greater than 2.

5. The process of statement 1 wherein the one or more monodentate ligand of formula (IV) each independently is of formula (IVA)

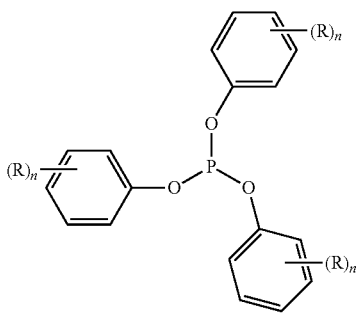

(IVA)

wherein each R is methyl and each n is independently 0, 1, or 2.

6. The process of any one of statements 1-5, wherein the ligand of formula (IV) is of formula (XIII) or (XIV).

7. The process of statement 6, wherein a mixture of the ligands of formula (XIII) and of formula (XIV) are admixed.

8. The process of any one of statements 1-7, wherein for the ligand of formula (III) or formula (IIIA) or formula (IV), each respective $R^1$, $R^2$, $R^3$, $R^{12}$, $R^{13}$, $R^{22}$, $R^{23}$ or $R^{34}$ is each an independently selected (C6-C20)aryl group, wherein each ring thereof is independently unsubstituted or is substituted with 1-4 substituents independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl (C1-C10)alkoxy, (C3-C10)cycloalkoxy(C1-C10)alkoxy, (C6-C20)aryl and (C6-C20)aryl(C1-C10)alkyl, or wherein any one or more pair of $R^1$ and $R^2$, or $R^{12}$ and $R^{13}$, or $R^{22}$ and $R^{23}$, is directly mutually bonded such that any mutually bonded pair, together with the respective $X^1$, $X^2$, $X^{12}$, $X^{13}$, $X^{22}$ or $X^{23}$ groups and the phosphorus atom to which they are bonded, forms a ring.

9. The process of any one of statements 1-8, wherein each independently selected $R^1$, $R^2$, $R^3$, $R^{12}$, $R^{13}$, $R^{22}$, $R^{23}$ or $R^{34}$ is a group of formula (II)

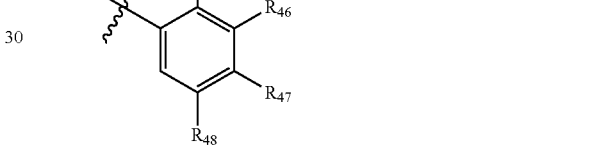

(II)

wherein a wavy line indicates a point of attachment; and wherein $R^{45}$ is independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, and (C3-C10)cycloalkoxy(C1-C10)alkoxy, and each of $R^{46}$, $R^{47}$ and $R^{48}$ is independently selected from the group consisting of H, (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, and (C3-C10)cycloalkoxy(C1-C10)alkoxy.

10. The process of any one of statements 1-9 wherein Y, or independently selected $Y^1$ or $Y^2$, is a (C6-C20)arylene group, wherein each ring thereof is independently unsubstituted or is substituted with 1-4 (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy (C1-C10)alkyl, (C3-C10)cycloalkyl(C1-C10)alkoxy, (C3-C10)cycloalkoxy(C1-C10)alkoxy, (C6-C20)aryl, (C6-C20)aryl(C1-C10)alkyl, fluorine, chlorine, bromine, or (C1-C10)halo alkyl.

11. The process of any one of statements 1-10, wherein the ligand of formula (III) is of formula (X):

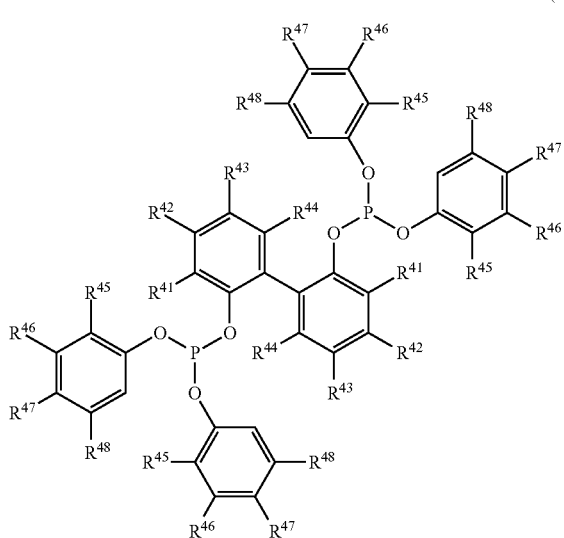

(X)

wherein each $R^{41}$ and $R^{45}$ is independently selected from the group consisting of (C1-C10)alkyl, (C3-C10)cycloalkyl, (C1-C10)alkoxy, (C3-C10)cyclo alkoxy, (C3-C10)cycloalkyl(C1-C10)alkyl, (C3-C10)cycloalkoxy(C1-C10)alkyl, (C3-C10)cycloalkyl(C1-C10)alkoxy, and (C3-C10)cycloalkoxy(C1-C10)alkoxy, and each of $R^{42}$, $R^{43}$, $R^{44}$, $R^{46}$, $R^{47}$ and $R^{48}$ is independently selected from the group consisting of H, (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cyclo alkoxy(C1-C10)alkyl, (C3-C10)cycloalkyl(C1-C10)alkoxy, and (C3-C10)cycloalkoxy(C1-C10)alkoxy.

12. The process of statement 11, wherein for the ligand of formula (X),
$R^{41}$ is methyl, ethyl, isopropyl, or cyclopentyl;
$R^{42}$ is H or methyl;
$R^{43}$ is H or (C1-C4)alkyl;
$R^{44}$ is H or methyl;
$R^{45}$ is methyl, ethyl, or isopropyl; and
$R^{46}$, $R^{47}$ and $R^{48}$ are independently H or (C1-C4)alkyl.

13. The process of any one of statements 1-10, wherein the ligand of formula (III) is of formula (VII):

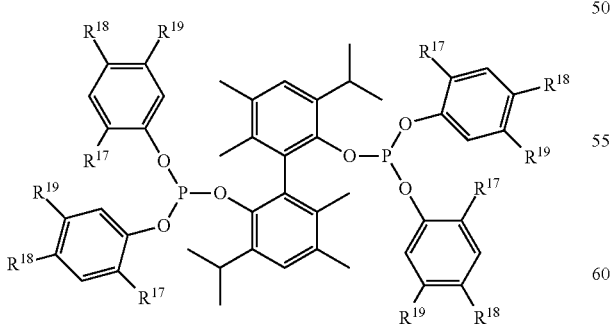

(VII)

wherein $R^{17}$ is methyl, ethyl or iso-propyl, and $R^{18}$ and $R^{19}$ are independently H or methyl.

14. The process of any one of statements 1-10, wherein the ligand of formula (III) is of formula (XII)

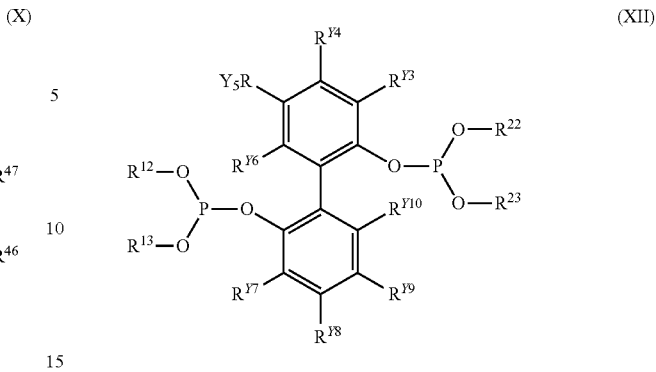

(XII)

wherein $R^{12}$, $R^{13}$, $R^{22}$ and $R^{23}$ are each independently an unsubstituted or a substituted monovalent aryl, and each of $R^{Y3}$-$R^{Y10}$ is independently selected from the group consisting of hydrogen, (C1-C10) alkyl, and (C1-C10)alkoxy, or wherein two adjacent $R^{Y3}$-$R^{Y10}$ groups together form an optionally substituted fused aryl ring.

15. The process of statement 14, wherein $R^{12}$, $R^{13}$, $R^{22}$, and $R^{23}$ are each independently phenyl substituted at a respective single ortho-position with a (C1-C10)alkyl or (C1-C10)alkoxy, wherein respective meta- and para-positions of the $R^{12}$, $R^{13}$, $R^{22}$, and $R^{23}$ phenyls can each independently be unsubstituted or be independently substituted with (C1-C10)alkyl, (C3-C10)cycloalkyl, (C1-C10) alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, or (C3-C10)cycloalkoxy (C1-C10)alkoxy;
$R^{Y6}$ and $R^{Y10}$ are independently (C1-C10)alkyl or (C1-C10)alkoxy, and $R^{Y3}$, $R^{Y4}$, $R^{Y5}$, $R^{Y7}$, $R^{Y8}$, and $R^{Y9}$, are independently H, (C1-C10)alkyl, or (C1-C10)alkoxy, provided that at least one of $R^{Y3}$, $R^{Y4}$, or $R^{Y5}$, and at least one of $R^{Y7}$, $R^{Y8}$, or $R^{Y9}$, is (C1-C10)alkyl or (C1-C10)alkoxy.

16. The process of any one of statements 1-10, wherein the ligand of formula (III) is of formula (V):

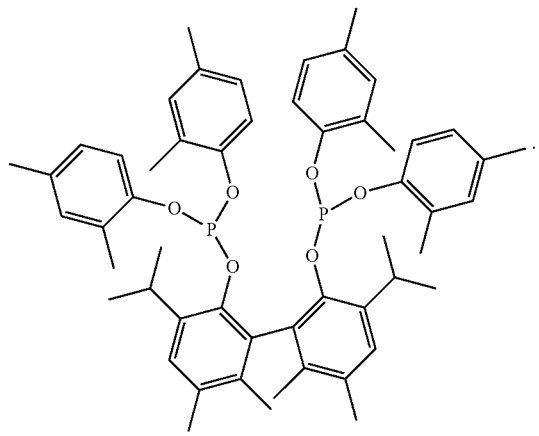

(V)

17. A process of stabilizing a reaction mixture resulting from the catalytic hydrocyanation process of butadiene in the preparation of adiponitrile in the presence of a phosphorus-based ligand of formula (III) or formula (IIIA) or a mixture thereof, in a hydrocyanation reaction milieu comprising water, the ligands having respective formulas:

a bidentate phosphorus-based ligand of formula (III)

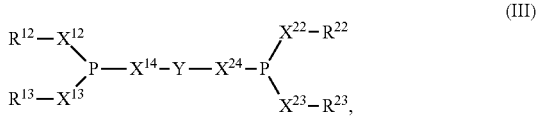

or,
a tridentate phosphorus-based ligand of formula (IIIA)

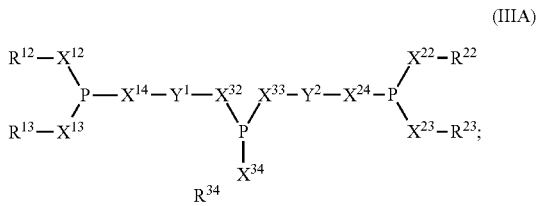

wherein for the ligand of formula (III), $X^{12}$, $X^{13}$, $X^{14}$, $X^{22}$, $X^{23}$, and $X^{24}$, each independently is oxygen or a bond, provided that at least one of $X^{12}$, $X^{13}$, $X^{14}$, $X^{22}$, $X^{23}$, or $X^{24}$ is oxygen, and for the ligand of formula (IIIA), $X^{12}$, $X^{13}$, $X^{14}$, $X^{22}$, $X^{23}$, $X^{24}$, $X^{32}$, $X^{33}$, and $X^{34}$, each independently is oxygen or a bond, provided that at least one of $X^{12}$, $X^{13}$, $X^{14}$, $X^{22}$, $X^{23}$, $X^{24}$, $X^{32}$, $X^{33}$, or $X^{34}$ is oxygen;

for the ligand of formula (III), $R^{12}$, $R^{13}$, $R^{22}$, and $R^{23}$, and for the ligand of formula (IIIA), $R^{12}$, $R^{13}$, $R^{22}$, $R^{23}$, and $R^{34}$, each independently is (C1-C10)alkyl, (C3-C10)cycloalkyl, (C3-C10)cycloalkyl(C1-C10)alkyl, (C6-C20)aryl, or (C6-C20)aryl(C1-C10)alkyl, wherein for any (C6-C20)aryl or (C6-C20)aryl(C1-C10)alkyl of $R^{12}$, $R^{13}$, $R^{22}$, $R^{23}$, or $R^{34}$, each ring thereof is unsubstituted or is substituted with 1-4 substituents independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, and (C6-C20)aryl(C1-C10)alkyl; or, optionally, one or more of pairs $R^{12}$ and $R^{13}$ or $R^{22}$ and $R^{23}$ are mutually directly bonded, such that the $R^{12}X^{12}$ and $R^{13}X^{13}$ groups, or the $R^{22}X^{22}$ and $R^{23}X^{23}$ groups, or both, together with the respective phosphorus atom to which each pair of groups is bonded, forms a respective ring;

for the ligand of formula (III) the group Y, and for the ligand of formula (IIIA), the groups $Y^1$ and $Y^2$ independently, is an (C6-C20)arylene group, wherein each ring thereof is independently unsubstituted or is substituted with 1-4 (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, (C6-C20)aryl(C1-C10)alkyl, fluorine, chlorine, bromine, or (C1-C10)haloalkyl;

the process comprising adding to said reaction mixture before or during said hydrocyanation therewith a stabilizing amount of one or more monodentate phosphorus-based ligand of formula (IV)

wherein $X^1$, $X^2$ and $X^3$ are each independently oxygen or a single bond, provided that at least one of $X^1$, $X^2$, or $X^3$ is an oxygen; and $R^1$, $R^2$ and $R^3$ is each independently (C1-C10)alkyl, (C3-C10)cycloalkyl, (C3-C10)cycloalkyl(C1-C10)alkyl, (C6-C20)aryl, or (C6-C20)aryl(C1-C10)alkyl, wherein for any (C6-C20)aryl or (C6-C20)aryl(C1-C10)alkyl of $R^1$, $R^2$, or $R^3$ each ring thereof is independently unsubstituted or is substituted with 1-4 substituents independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, and (C6-C20)aryl(C1-C10)alkyl; or, optionally, any two of $R^1$, $R^2$, or $R^3$ are directly bonded to each other such that any pair of $R^1X^1$, $R^2X^2$, and $R^3X^3$ groups, together with the phosphorus atom to which they are bonded, forms a ring;

wherein the monodentate ligand of formula (IV) has a rate of hydrolysis greater than a rate of hydrolysis of a bidentate ligand of formula (III) or a tridentate ligand of formula (IIIA) or a mixture thereof, in the presence of water in a hydrocyanation reaction milieu optionally further comprising an organic component, under conditions of concentration, temperature, and time sufficient to bring about hydrolysis of the monodentate ligand of formula (IV).

18. The process of statement 17, wherein the one or more monodentate ligand of formula (IV) is produced as a byproduct in a synthetic process for the production of the bidentate ligand of Formula (III) or the tridentate ligand of formula (IIIA) or both.

19. The process of statement 17 or 18 wherein the monodentate ligand of formula (IV) is a ligand of formula (XIII):

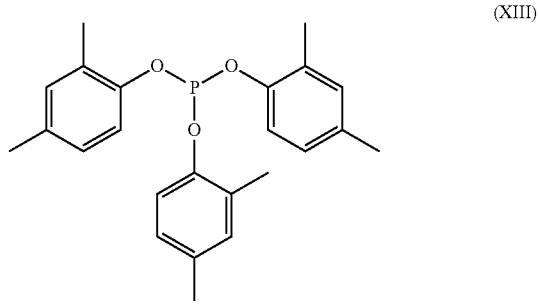

or the ligand of formula (XIV):

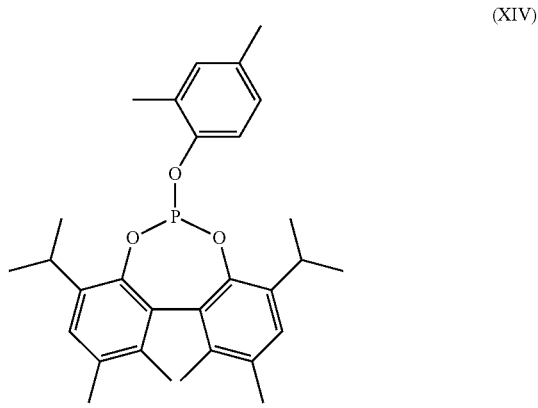 [SMILES: Cc1ccc(Op2oc3c(C(C)C)cc(C)c(C)c3c3c(C)c(C)cc(C(C)C)c3o2)c(C)c1]

or is a mixture thereof.

20. The process of any one of statements 17-19, wherein a molar ratio of the ligand of formula (IV) that is admixed to the ligand of formula (III) or formula (IIIA) or mixture thereof is at least 0.01.

21. The process of any one of statements 17-19, wherein a molar ratio of the ligand of formula (IV) that is admixed to the ligand of formula (III) or formula (IIIA) or mixture thereof is from about 0.01 to 2.

22. The process of any one of statements 17-21, wherein the ligand of formula (IV) is of formula (XIII) or (XIV).

23. The process of statement 22, wherein a mixture of the ligands of formula (XIII) and of formula (XIV) are admixed.

24. The process of any one of statements 17-23, wherein for the ligand of formula (III) or formula (IIIA) or formula (IV), each respective $R^1$, $R^2$, $R^3$, $R^{12}$, $R^{13}$, $R^{22}$, $R^{23}$ or $R^{34}$ is each an independently selected (C6-C20)aryl group, wherein each ring thereof is independently unsubstituted or is substituted with 1-4 substituents independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl and (C6-C20)aryl(C1-C10)alkyl, or wherein any one or more pair of $R^1$ and $R^2$, or $R^{12}$ and $R^{13}$, or $R^{22}$ and $R^{23}$, is directly mutually bonded such that any mutually bonded pair, together with the respective $X^1$, $X^2$, $X^{12}$, $X^{13}$, $X^{22}$ or $X^{23}$ groups and the phosphorus atom to which they are bonded, forms a ring.

25. The process of any one of statements 17-24, wherein each independently selected $R^1$, $R^2$, $R^3$, $R^{12}$, $R^{13}$, $R^{22}$, $R^{23}$ or $R^{34}$ is a group of formula (II)

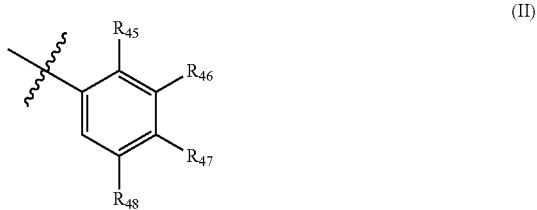

(II)

wherein a wavy line indicates a point of attachment; and wherein $R^{45}$ is independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, and (C3-C10)cycloalkoxy(C1-C10)alkoxy, and each of $R^{46}$, $R^{47}$ and $R^{48}$ is independently selected from the group consisting of H, (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, and (C3-C10)cycloalkoxy(C1-C10)alkoxy.

26. The process of any one of statements 16-24 wherein Y, or independently selected $Y^1$ or $Y^2$, is a (C6-C20)arylene group, wherein each ring thereof is independently unsubstituted or is independently substituted with 1-4 (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, (C6-C20)aryl(C1-C10)alkyl, fluorine, chlorine, bromine, or (C1-C10)halo alkyl.

27. The process of any one of statements 17-26, wherein the ligand of formula (III) is of formula (X):

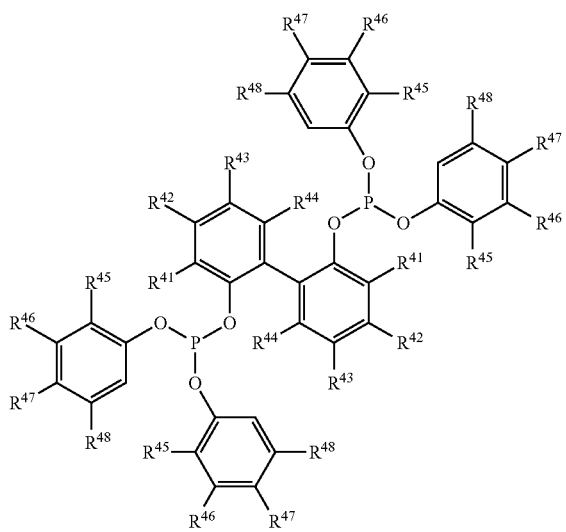

(X)

wherein each $R^{41}$ and $R^{45}$ is independently selected from the group consisting of (C1-C10)alkyl, (C3-C10)cycloalkyl, (C1-C10)alkoxy, (C3-C10)cyclo alkoxy, (C3-C10)cycloalkyl(C1-C10)alkyl, (C3-C10)cycloalkoxy(C1-C10)alkyl, (C3-C10)cycloalkyl(C1-C10)alkoxy, and (C3-C10)cycloalkoxy(C1-C10)alkoxy, and each of $R^{42}$, $R^{43}$, $R^{44}$, $R^{46}$, $R^{47}$ and $R^{48}$ is independently selected from the group consisting of H, (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, and (C3-C10)cycloalkoxy(C1-C10)alkoxy.

28. The process of statement 27, wherein for the ligand of formula (X),
$R^{41}$ is methyl, ethyl, isopropyl or cyclopentyl;
$R^{42}$ is H or methyl;
$R^{43}$ is H or (C1-C4)alkyl;
$R^{44}$ is H or methyl;
$R^{45}$ is methyl, ethyl, or isopropyl; and
$R^{46}$, $R^{47}$ and $R^{48}$ are independently H or (C1-C4)alkyl.

29. The process of any one of statements 17-26, wherein the ligand of formula (III) is of formula (VII):

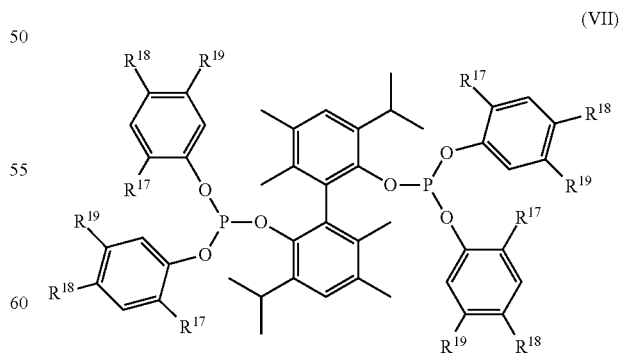

(VII)

wherein $R^{17}$ is methyl, ethyl or iso-propyl, and $R^{18}$ and $R^{19}$ are independently H or methyl.

30. The process of any one of statements 16-25, wherein the ligand of formula (III) is of formula (XII)

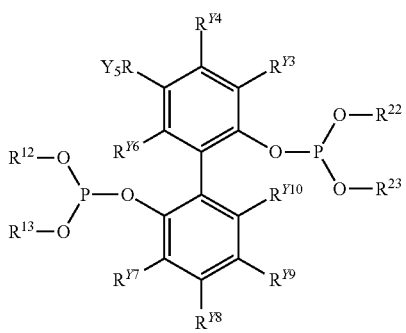

(XII)

wherein $R^{12}$, $R^{13}$, $R^{22}$ and $R^{23}$ are each independently an unsubstituted or a substituted monovalent aryl, and each of $R^{Y3}$-$R^{Y10}$ is independently selected from the group consisting of hydrogen, (C1-C10) alkyl, and (C1-C10)alkoxy, or wherein two adjacent $R^{Y3}$-$R^{Y10}$ groups together form an optionally substituted fused aryl ring.

31. The process of claim 30, wherein $R^{12}$, $R^{13}$, $R^{22}$, and $R^{23}$ are each independently phenyl substituted at a respective single ortho-position with a (C1-C10)alkyl or (C1-C10) alkoxy, wherein respective meta- and para-positions of the $R^{12}$, $R^{13}$, $R^{22}$, and $R^{23}$ phenyls can each independently be unsubstituted or be independently substituted with (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, or (C3-C10)cycloalkoxy(C1-C10)alkoxy;

$R^{Y6}$ and $R^{Y10}$ are independently (C1-C10)alkyl or (C1-C10)alkoxy, and $R^{Y3}$, $R^{Y4}$, $R^{Y5}$, $R^{Y7}$, $R^{Y8}$, and $R^{Y9}$, are independently H, (C1-C10)alkyl, or (C1-C10)alkoxy, provided that at least one of $R^{Y3}$, $R^{Y4}$, or $R^{Y5}$, and at least one of $R^{Y7}$, $R^{Y8}$, or $R^{Y9}$, is (C1-C10)alkyl or (C1-C10)alkoxy.

32. The process of any one of statements 17-26, wherein the ligand of formula (III) is of formula (V):

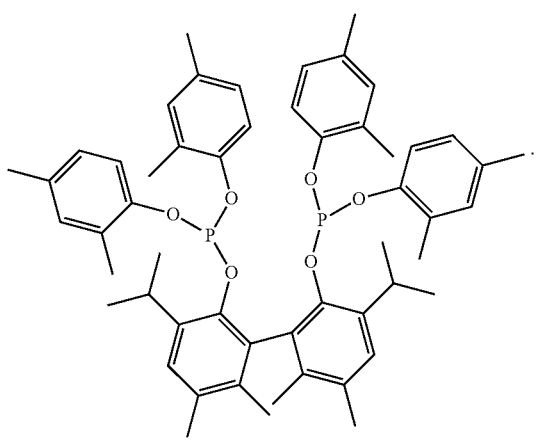

(V)

33. The process of statement 17 wherein the one or more monodentate ligand of formula (IV) is independently of formula (IVA)

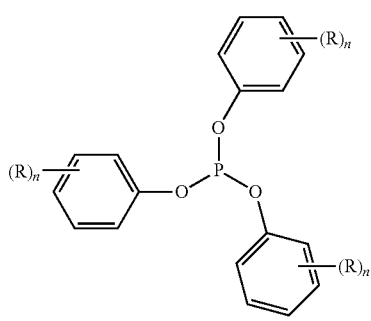

(IVA)

wherein each R is methyl, and each n is independently 0, 1, or 2.

34. The process of any one of statements 17-32, wherein a molar ratio of the ligand or mixture thereof of formula (IV) that is admixed to the ligand of formula (III) or formula (IIIA) or mixture thereof is at least 0.01.

35. The process of any one of statements 17-33, wherein a molar ratio of the ligand or mixture thereof of formula (IV) that is admixed to the ligand of formula (III) or formula (IIIA) or mixture thereof is from 0.01 to 2.

36. The process of any one of statements 17-35 wherein the ligand or mixture thereof of formula (IV) is of formula (XIII)

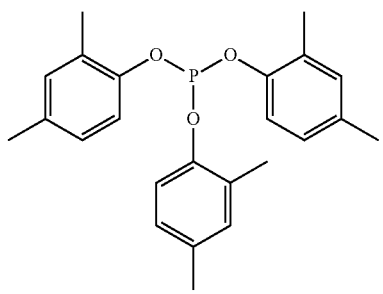

(XIII)

or is of formula (XIV)

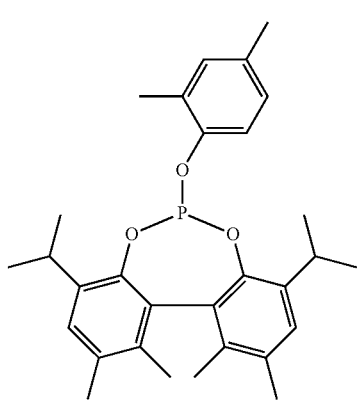

(XIV)

or is a mixture thereof.

37. The process of statement 36 wherein ligand or mixture thereof of formula (IV) is a mixture of the ligand of formula (XIII) and the ligand of formula (XIV).

38. The process of any one of statements 17-37 wherein the reaction mixture is a batch or a continuous process reaction mixture.
39. The process of any one of statements 16-38 wherein the admixing is done during the hydrocyanation reaction process.
40. A reaction mixture resulting from a catalytic hydrocyanation reaction process of butadiene in the preparation of adiponitrile, in a hydrocyanation reaction milieu comprising water, the reaction mixture comprising a phosphorus-based ligand of formula (III) or formula (IIIA) or a mixture thereof, the ligands having respective formulas:
a bidentate phosphorus-based ligand of formula (III)

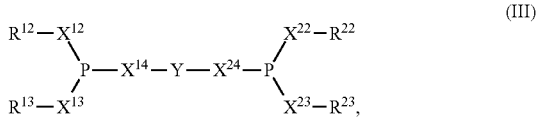

or,
a tridentate phosphorus-based ligand of formula (IIIA)

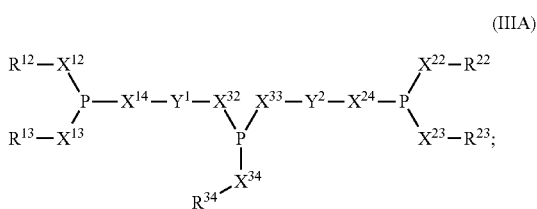

wherein for the ligand of formula (III), $X^{12}$, $X^{13}$, $X^{14}$, $X^{22}$, $X^{23}$, and $X^{24}$, each independently is oxygen or a bond, provided that at least one of $X^{12}$, $X^{13}$, $X^{14}$, $X^{22}$, $X^{23}$, or $X^{24}$ is oxygen, and for the ligand of formula (IIIA), $X^{12}$, $X^{13}$, $X^{14}$, $X^{22}$, $X^{23}$, $X^{24}$, $X^{32}$, $X^{33}$, and $X^{34}$, each independently is oxygen or a bond, provided that at least one of $X^{12}$, $X^{13}$, $X^{14}$, $X^{22}$, $X^{23}$, $X^{24}$, $X^{32}$, $X^{33}$, or $X^{34}$ is oxygen;

for the ligand of formula (III), $R^{12}$, $R^{13}$, $R^{22}$, and $R^{23}$, and for the ligand of formula (IIIA), $R^{12}$, $R^{13}$, $R^{22}$, $R^{23}$, and $R^{34}$, each independently is (C1-C10)alkyl, (C3-C10)cycloalkyl, (C3-C10)cycloalkyl(C1-C10)alkyl, (C6-C20)aryl, or (C6-C20)aryl(C1-C10)alkyl, wherein for any (C6-C20)aryl or (C6-C20)aryl(C1-C10)alkyl of $R^{12}$, $R^{13}$, $R^{22}$, $R^{23}$, or each ring thereof is unsubstituted or is substituted with 1-4 substituents independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, and (C6-C20)aryl(C1-C10)alkyl; or, optionally, one or more of pairs $R^{12}$ and $R^{13}$ or $R^{22}$ and $R^{23}$ are mutually directly bonded, such that the $R^{12}X^{12}$ and $R^{13}X^{13}$ groups, or the $R^{22}X^{22}$ and $R^{23}X^{23}$ groups, or both, together with the respective phosphorus atom to which each pair of groups is bonded, forms a respective ring;

for the ligand of formula (III) the group Y, and for the ligand of formula (IIIA), the groups $Y^1$ and $Y^2$ independently, is an (C6-C20)arylene group, wherein each ring thereof is independently unsubstituted or is substituted with 1-4 (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, (C6-C20)aryl(C1-C10)alkyl, fluorine, chlorine, bromine, or (C1-C10)haloalkyl;

and further comprising an amount of one of more monodentate phosphorus-based ligand of formula (IV)

$$P(X^1R^1)(X^2R^2)(X^3R^3) \quad \quad (IV)$$

wherein $X^1$, $X^2$ and $X^3$ are each independently oxygen or a single bond, provided that at least one of $X^1$, $X^2$, or $X^3$ is an oxygen; and $R^1$, $R^2$ and $R^3$ is each independently (C1-C10)alkyl, (C3-C10)cycloalkyl, (C3-C10)cycloalkyl(C1-C10)alkyl, (C6-C20)aryl, or (C6-C20)aryl(C1-C10)alkyl, wherein for any (C6-C20)aryl or (C6-C20)aryl(C1-C10) alkyl of $R^1$, $R^2$, or $R^3$ each ring thereof is independently unsubstituted or is substituted with 1-4 substituents independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, and (C6-C20)aryl(C1-C10)alkyl; or, optionally, any two of $R^1$, $R^2$, or $R^3$ are directly bonded to each other such that any pair of $R^1X^1$, $R^2X^2$, and $R^3X^3$ groups, together with the phosphorus atom to which they are bonded, forms a ring;

wherein a smaller proportion of the ligand of formula (IV) relative to the ligand of formula (III) or formula (IIIA) or mixture thereof, is present than the proportion of the ligand of formula (IV) relative to the ligand of formula (III) or formula (IIIA) or mixture thereof, that was present before the catalytic hydrocyanation reaction was commenced.
41. The mixture of statement 40 wherein the monodentate ligand of formula (IV) is a ligand of formula (XIII):

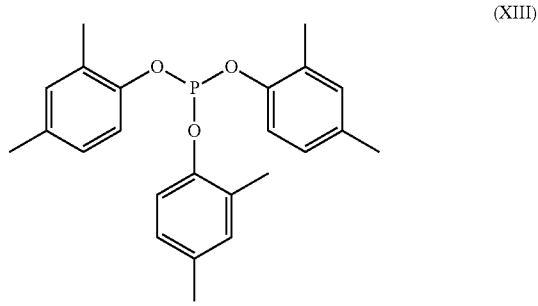

or a ligand of formula (XIV):

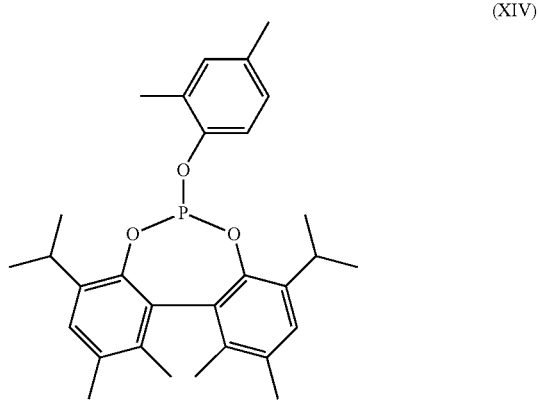

or a mixture thereof.

42. The mixture of any one of statements 40-41, wherein a molar ratio of the ligand of formula (IV) that is admixed to the ligand of formula (III) or formula (IIIA) or mixture thereof, is at least 0.01, and, optionally, is no greater than 2.

43. The mixture of any one of statements 40-42 wherein the one or more monodentate ligand of formula (IV) is independently of formula (IVA)

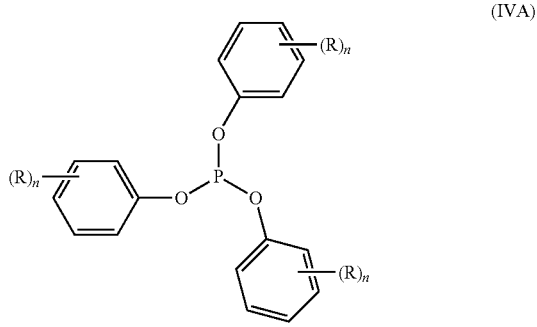

wherein each R is methyl, and each n is independently 0, 1, or 2.

44. The mixture of any one of statements 40-43, wherein the ligand of formula (IV) is of formula (XIII) or (XIV).

45. The mixture of any one of statements 40-44, wherein a mixture of the ligands of formula (XIII) and of formula (XIV) are admixed.

46. The mixture of any one of statements 40-45, wherein for the ligand of formula (III) or formula (IIIA) or formula (IV), each respective $R^1$, $R^2$, $R^3$, $R^{12}$, $R^{13}$, $R^{22}$, $R^{23}$ or $R^{34}$ is each an independently selected (C6-C20)aryl group, wherein each ring thereof is independently unsubstituted or is substituted with 1-4 substituents independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl and (C6-C20)aryl(C1-C10)alkyl, or wherein any one or more pair of $R^1$ and $R^2$, or $R^{12}$ and $R^{13}$, or $R^{22}$ and $R^{23}$, is directly mutually bonded such that any mutually bonded pair, together with the respective $X^1$, $X^2$, $X^{12}$, $X^{13}$, $X^{22}$ or $X^{23}$ groups and the phosphorus atom to which they are bonded, forms a ring.

47. The mixture of any one of statements 40-46, wherein each independently selected $R^1$, $R^2$, $R^3$, $R^{12}$, $R^{13}$, $R^{22}$, $R^{23}$ or $R^{34}$ is a group of formula (II)

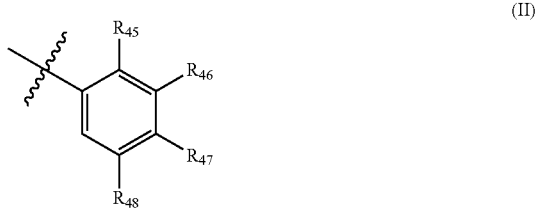

wherein a wavy line indicates a point of attachment; and wherein $R^{45}$ is independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, and (C3-C10)cycloalkoxy(C1-C10)alkoxy, and each of $R^{46}$, $R^{47}$ and $R^{48}$ is independently selected from the group consisting of H, (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, and (C3-C10)cycloalkoxy(C1-C10)alkoxy.

48. The mixture of any one of statements 40-47 wherein Y, or independently selected $Y^1$ or $Y^2$, is a (C6-C20)arylene group, wherein each ring thereof is independently unsubstituted or is substituted with 1-4 (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, (C6-C20)aryl(C1-C10)alkyl, fluorine, chlorine, bromine, or (C1-C10)halo alkyl.

49. The mixture of any one of statements 40-48, wherein the ligand of formula (III) is of formula (X):

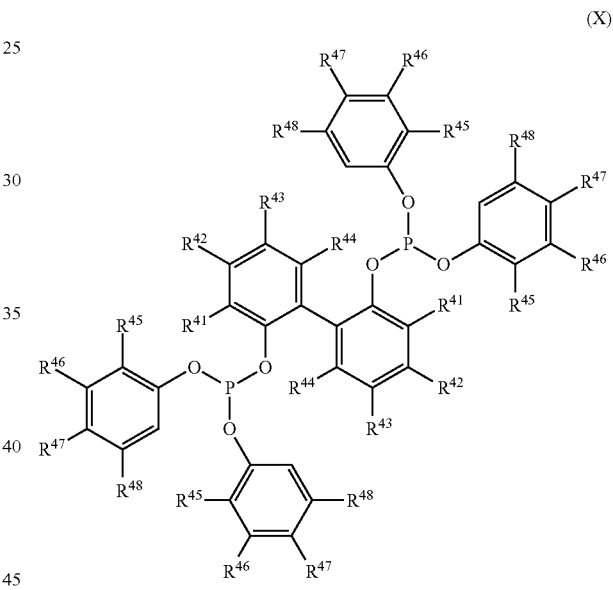

wherein each $R^{41}$ and $R^{45}$ is independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, and (C3-C10)cycloalkoxy(C1-C10)alkoxy, and each of $R^{42}$, $R^{43}$, $R^{44}$, $R^{46}$, $R^{47}$ and $R^{48}$ is independently selected from the group consisting of H, (C1-C10)alkyl, (C3-C10)cycloalkyl, (C1-C10)alkoxy, (C3-C10)cycloalkoxy, (C3-C10)cycloalkyl (C1-C10)alkyl, (C3-C10)cyclo alkoxy(C1-C10)alkyl, (C3-C10)cycloalkyl(C1-C10)alkoxy, and (C3-C10)cycloalkoxy(C1-C10)alkoxy.

50. The mixture of statement 49, wherein for the ligand of formula (X),
$R^{41}$ is methyl, ethyl, isopropyl, or cyclopentyl;
$R^{42}$ is H or methyl;
$R^{43}$ is H or (C1-C4)alkyl;
$R^{44}$ is H or methyl;
$R^{45}$ is methyl, ethyl, or isopropyl; and
$R^{46}$, $R^{47}$ and $R^{48}$ are independently H or (C1-C4)alkyl.

51. The mixture of any one of statements 40-48, wherein the ligand of formula (III) is of formula (VII):

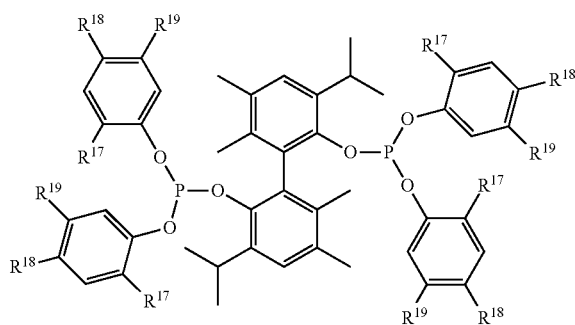

wherein $R^{17}$ is methyl, ethyl or iso-propyl, and $R^{18}$ and $R^{19}$ are independently H or methyl.

52. The mixture of any one of statements 40-48, wherein the ligand of formula (III) is of formula (V):

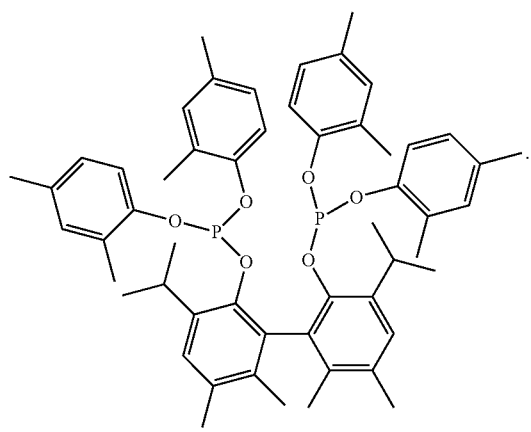

(V)

53. The mixture of any one of statements 40-48, wherein the ligand of formula (III) is of formula (XII)

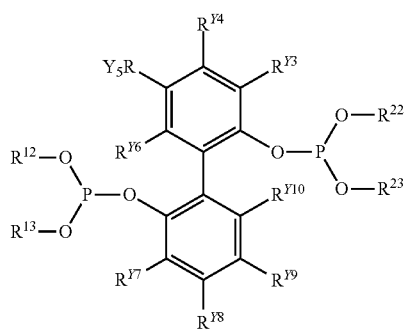

(XII)

wherein $R^{12}$, $R^{13}$, $R^{22}$ and $R^{23}$ are each independently an unsubstituted or a substituted monovalent aryl, and each of $R^{Y3}$-$R^{Y10}$ is independently selected from the group consisting of hydrogen, (C1-C10) alkyl, and (C1-C10)alkoxy, or wherein two adjacent $R^{Y3}$-$R^{Y10}$ groups together form an optionally substituted fused aryl ring.

54. The mixture of statement 53, wherein $R^{12}$, $R^{13}$, $R^{22}$, and $R^{23}$ are each independently phenyl substituted at a respective single ortho-position with a (C1-C10)alkyl or (C1-C10)alkoxy, wherein respective meta- and para-positions of the $R^{12}$, $R^{13}$, $R^{22}$, and $R^{23}$ phenyls can each independently be unsubstituted or be independently substituted with (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, or (C3-C10)cycloalkoxy(C1-C10)alkoxy;

$R^{Y6}$ and $R^{Y10}$ are independently (C1-C10)alkyl or (C1-C10)alkoxy, and $R^{Y3}$, $R^{Y4}$, $R^{Y5}$, $R^{Y7}$, $R^{Y8}$, and $R^{Y9}$, are independently H, (C1-C10)alkyl, or (C1-C10)alkoxy, provided that at least one of $R^{Y3}$, $R^{Y4}$, or $R^{Y5}$, and at least one of $R^{Y7}$, $R^{Y8}$, or $R^{Y5}$ is (C1-C10)alkyl or (C1-C10)alkoxy.

Accordingly, the foregoing aspects are set forth without any loss of generality to, and without imposing limitations upon any claimed invention. It is to be understood that this disclosure is not limited to particular aspects described, as such can vary. It is also to be understood that the terminology used herein is for the purpose of describing particular aspects only, and is not intended to be limiting, since the scope of the present disclosure will be limited only by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. As will be apparent to those of skill in the art upon reading this disclosure, each of the individual aspects described and illustrated herein has discrete components and features that can be readily separated from or combined with the features of any of the other several examples without departing from the scope or spirit of the present disclosure. Any recited method can be carried out in the order of events recited or in any other order that is logically possible.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. Applicants reserve the right to physically incorporate into this specification any and all materials and information from any such cited patents or publications. The citation of any publication is for its disclosure prior to the filing date and should not be construed as an admission that the present disclosure is not entitled to antedate such publication by virtue of prior disclosure. Further, the dates of publication provided could be different from the actual publication dates that can need to be independently confirmed. All patents and publications referenced or mentioned herein are also indicative of the levels of skill of those skilled in the art to which the invention pertains.

What is claimed is:

1. A process for stabilizing a phosphorus-based bidentate ligand of formula (III) or tridentate ligand of formula (IIIA) or a mixture thereof, in a hydrocyanation reaction milieu comprising at least 2500 ppm of water, the ligands having respective formulas:

a bidentate phosphorus-based ligand of formula (III)

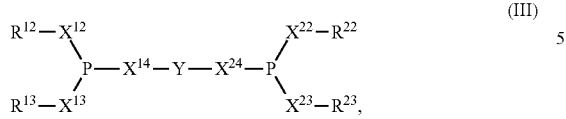

or,
a tridentate phosphorus-based ligand of formula (IIIA)

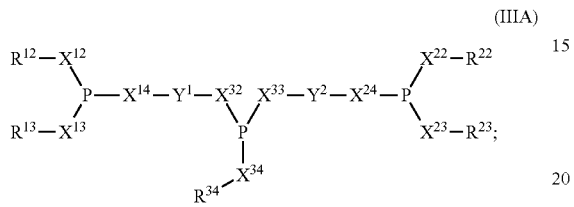

wherein for the ligand of formula (III), $X^{12}$, $X^{13}$, $X^{14}$, $X^{22}$, $X^{23}$, and $X^{24}$, each independently is oxygen or a bond, provided that at least one of $X^{12}$, $X^{13}$, $X^{14}$, $X^{22}$, $X^{23}$, or $X^{24}$ is oxygen, and for the ligand of formula (IIIA), $X^{12}$, $X^{13}$, $X^{14}$, $X^{22}$, $X^{23}$, $X^{24}$, $X^{32}$, $X^{33}$, and $X^{34}$, each independently is oxygen or a bond, provided that at least one of $X^{12}$, $X^{13}$, $X^{14}$, $X^{22}$, $X^{23}$, $X^{24}$, $X^{32}$, $X^{33}$, or $X^{34}$ is oxygen;
for the ligand of formula (III), $R^{12}$, $R^{13}$, $R^{22}$, and $R^{23}$, and for the ligand of formula (IIIA), $R^{12}$, $R^{13}$, $R^{22}$, $R^{23}$, and $R^{34}$, each independently is (C1-C10)alkyl, (C3-C10)cycloalkyl, (C3-C10)cycloalkyl(C1-C10)alkyl, (C6-C20)aryl, or (C6-C20)aryl(C1-C10)alkyl, wherein for any (C6-C20)aryl or (C6-C20)aryl(C1-C10)alkyl of $R^{12}$, $R^{13}$, $R^{22}$, $R^{23}$, or $R^{34}$, each ring thereof is unsubstituted or is substituted with 1-4 substituents independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, and (C6-C20)aryl(C1-C10)alkyl;
or, optionally, one or more of pairs $R^{12}$ and $R^{13}$ or $R^{22}$ and $R^{23}$ are mutually directly bonded, such that the $R^{12}X^{12}$ and $R^{13}X^{13}$ groups, or the $R^{22}X^{22}$ and $R^{23}X^{23}$ groups, or both together with the respective phosphorus atom to which each pair of groups is bonded, forms a respective ring;
for the ligand of formula (III) the group Y, and for the ligand of formula (IIIA), the groups $Y^1$ and $Y^2$ independently, is an (C6-C20)arylene group, wherein each ring thereof is independently unsubstituted or is independently substituted with 1-4 (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, (C6-C20)aryl(C1-C10)alkyl, fluorine, chlorine, bromine, or (C1-C10)haloalkyl;
the process comprising admixing with the bidentate and/or the tridentate ligand a stabilizing amount of one or more monodentate phosphorus-based ligand of formula (IV)

$$P(X^1R^1)(X^2R^2)(X^3R^3) \quad (IV)$$

wherein $X^1$, $X^2$ and $X^3$ are each independently oxygen or a single bond, provided that at least one of $X^1$, $X^2$, or $X^3$ is an oxygen; and $R^1$, $R^2$ and $R^3$ is each independently (C1-C10)alkyl, (C3-C10)cycloalkyl, (C3-C10)cycloalkyl(C1-C10)alkyl, (C6-C20)aryl, or (C6-C20)aryl(C1-C10)alkyl, wherein for any (C6-C20)aryl or (C6-C20)aryl(C1-C10)alkyl of $R^1$, $R^2$, or $R^3$ each ring thereof is independently unsubstituted or is substituted with 1-4 substituents independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, and (C6-C20)aryl(C1-C10)alkyl; or, optionally, any two of $R^1$, $R^2$, or $R^3$ are directly bonded to each other such that any pair of $R^1X^1$, $R^2X^2$, and $R^3X^3$ groups, together with the phosphorus atom to which they are bonded, forms a ring;

wherein a molar ratio of the ligand of formula (IV) that is admixed to the ligand of formula (III) or formula (IIIA) or mixture thereof, is at least 0.01:1;

wherein the monodentate ligand of formula (IV) has a rate of hydrolysis greater than a rate of hydrolysis of a bidentate ligand of formula (III) or a tridentate ligand of formula (IIIA) or a mixture thereof, in the presence of water in a hydrocyanation reaction milieu optionally further comprising an organic component, under conditions of concentration, temperature, and time sufficient to bring about hydrolysis of the monodentate ligand of formula (IV).

2. The process of claim 1, wherein the one or more monodentate ligand of formula (IV) is produced as a byproduct in a synthetic process for the production of the bidentate ligand of Formula (III) or the tridentate ligand of formula (IIIA) or both.

3. The process of claim 1 wherein the monodentate ligand of formula (IV) is a ligand of formula (XIII):

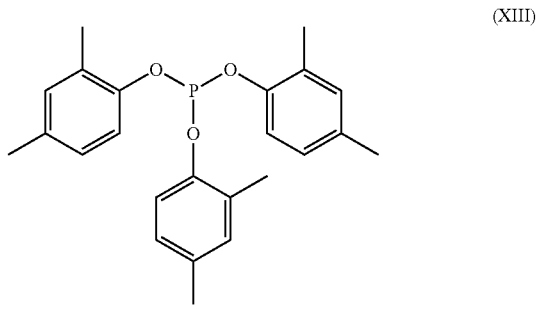

or a ligand of formula (XIV):

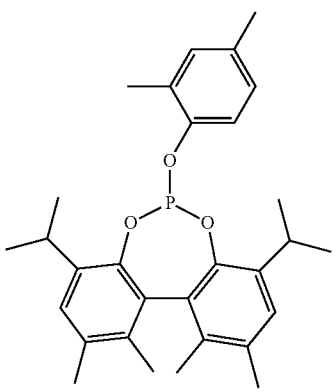

(XIV)

or a mixture thereof.

4. The process of claim 1, wherein a molar ratio of the ligand of formula (IV) that is admixed to the ligand of formula (III) or formula (IIIA) or mixture thereof, is at least 0.01, and, optionally, is no greater than 2.

5. The process of claim 1 wherein the one or more monodentate ligand of formula (IV) is each independently of formula (IVA)

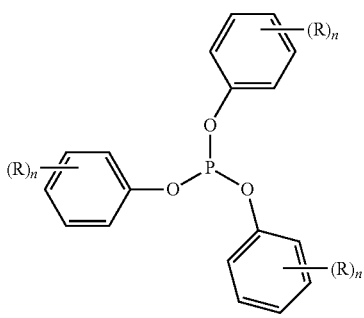

(IVA)

wherein each R is methyl and each n is independently 0, 1, or 2.

6. The process of claim 1, wherein the ligand of formula (IV) is of formula (XIII) or (XIV).

7. The process of claim 6, wherein a mixture of the ligands of formula (XIII) and of formula (XIV) are admixed.

8. The process of claim 1, wherein $R^1$, $R^2$, $R^3$, $R^{12}$, $R^{13}$, $R^{22}$, $R^{23}$ or $R^{34}$ is each an independently selected (C6-C20) aryl group, wherein each ring thereof is independently unsubstituted or is substituted with 1-4 substituents independently selected from the group consisting of (C1-C10) alkyl, (C3-C10)cycloalkyl, (C1-C10)alkoxy, (C3-C10)cycloalkoxy, (C3-C10)cycloalkyl(C1-C10)alkyl, (C3-C10) cycloalkoxy(C1-C10)alkyl, (C3-C10)cycloalkyl(C1-C10) alkoxy, (C3-C10)cycloalkoxy(C1-C10)alkoxy, (C6-C20) aryl and (C6-C20)aryl(C1-C10)alkyl, or wherein any one or more pair of $R^1$ and $R^2$, or $R^{12}$ and $R^{13}$, or $R^{22}$ and $R^{23}$, is directly mutually bonded such that any mutually bonded pair, together with the respective $X^1$, $X^2$, $X^{12}$, $X^{13}$, $X^{22}$ or $X^{23}$ groups and the phosphorus atom to which they are bonded, forms a ring.

9. The process of claim 1, wherein each independently selected $R^1$, $R^2$, $R^3$, $R^{12}$, $R^{13}$, $R^{22}$, $R^{23}$ or $R^{34}$ is a group of formula (II)

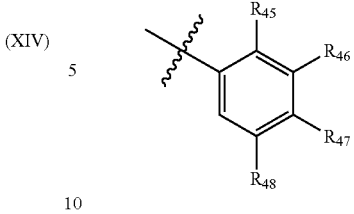

(II)

wherein a wavy line indicates a point of attachment; and wherein $R^{45}$ is independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, and (C6-C20)aryl, and each of $R^{48}$, $R^{47}$ and $R^{48}$ is independently selected from the group consisting of H, (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl (C1-C10)alkoxy, (C3-C10)cycloalkoxy(C1-C10) alkoxy, and (C6-C20)aryl.

10. The process of claim 1 wherein Y, or independently selected $Y^1$ or $Y^2$, is a (C6-C20)arylene group, wherein each ring thereof is independently unsubstituted or is substituted with 1-4 (C1-C10)alkyl, (C3-C10)cycloalkyl, (C1-C10) alkoxy, (C3-C10)cycloalkoxy, (C3-C10)cycloalkyl(C1-C10)alkyl, (C3-C10)cycloalkoxy(C1-C10)alkyl, (C3-C10) cycloalkyl(C1-C10)alkoxy, (C3-C10)cycloalkoxy(C1-C10) alkoxy, (C6-C20)aryl, (C6-C20)aryl(C1-C10)alkyl, fluorine, chlorine, bromine, or (C1-C10)haloalkyl.

11. The process of claim 1, wherein the ligand of formula (III) is of formula (X):

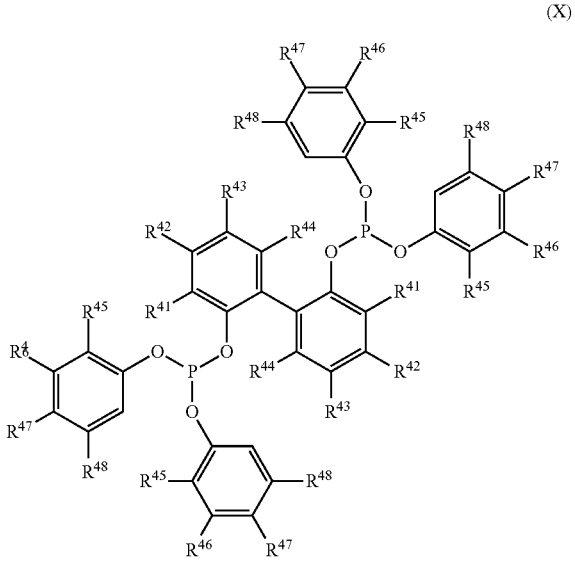

(X)

wherein each $R^{41}$ and $R^{45}$ is independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10) alkyl, (C3-C10)cycloalkyl(C1-C10)alkoxy, and (C3-C10) cycloalkoxy(C1-C10)alkoxy, and each of $R^{42}$, $R^{43}$, $R^{44}$, $R^{46}$, $R^{47}$ and $R^{48}$ is independently selected from the group consisting of H, (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, and (C3-C10)cycloalkoxy(C1-C10)alkoxy.

12. The process of claim 11, wherein for the ligand of formula (X),
$R^{41}$ is methyl, ethyl, isopropyl or cyclopentyl;
$R^{42}$ is H or methyl;
$R^{43}$ is H or (C1-C4)alkyl;
$R^{44}$ is H or methyl;
$R^{45}$ is methyl, ethyl, or isopropyl; and
$R^{46}$, $R^{47}$ and $R^{48}$ are independently H or (C1-C4)alkyl.

13. The process of claim 1, wherein the ligand of formula (III) is of formula (VII):

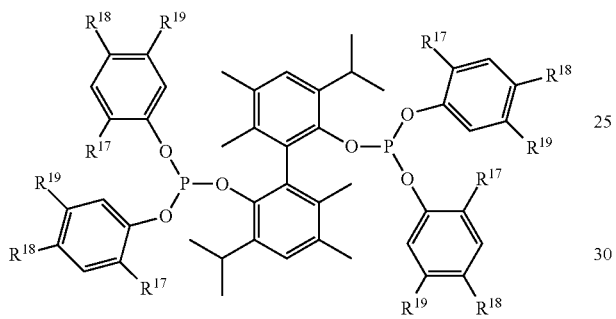

(VII)

wherein $R^{17}$ is methyl, ethyl, or iso-propyl, and $R^{18}$ and $R^{19}$ are independently H or methyl.

14. The process of claim 1, wherein the ligand of formula (III) is of formula (XII)

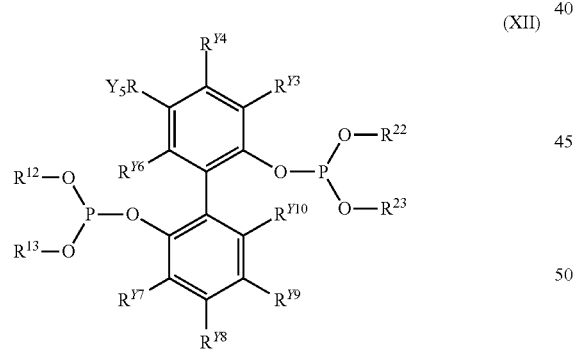

(XII)

wherein $R^{12}$, $R^{13}$, $R^{22}$ and $R^{23}$ are each independently an unsubstituted or a substituted monovalent aryl, and each of $R^{Y3}$-$R^{Y10}$ is independently selected from the group consisting of hydrogen, (C1-C10) alkyl, and (C1-C10)alkoxy, or wherein two adjacent $R^{Y3}$-$R^{Y10}$ groups together form an optionally substituted fused aryl ring.

15. The process of claim 14, wherein $R^{12}$, $R^{13}$, $R^{22}$, and $R^{23}$ are each independently phenyl substituted at a respective single ortho-position with a (C1-C10)alkyl or (C1-C10)alkoxy, wherein respective meta- and para-positions of the $R^{12}$, $R^{13}$, $R^{22}$, and $R^{23}$ phenyls can each independently be unsubstituted or be independently substituted with (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, or (C3-C10)cycloalkoxy(C1-C10)alkoxy;
$R^{Y6}$ and $R^{Y10}$ are independently (C1-C10)alkyl or (C1-C10)alkoxy, and $R^{Y3}$, $R^{Y4}$, $R^{Y5}$, $R^{Y7}$, $R^{Y8}$, and $R^{Y9}$, are independently H, (C1-C10)alkyl, or (C1-C10)alkoxy, provided that at least one of $R^{Y3}$, $R^{Y4}$, or $R^{Y5}$, and at least one of $R^{Y7}$, $R^{Y8}$, or $R^{Y9}$, is (C1-C10)alkyl or (C1-C10)alkoxy.

16. The process of claim 1, wherein the ligand of formula (III) is of formula (V):

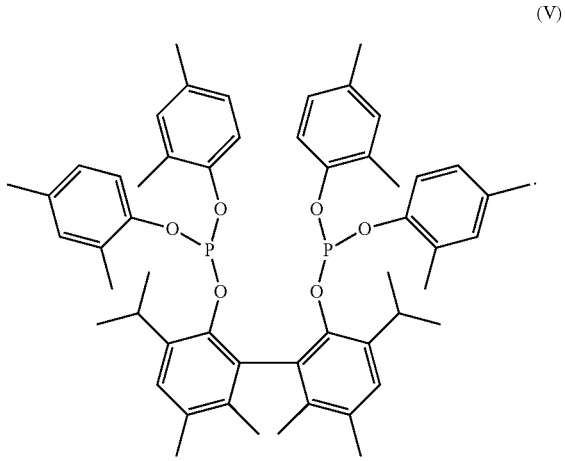

(V)

17. A process of stabilizing a reaction mixture resulting from the catalytic hydrocyanation process of butadiene in the preparation of adiponitrile in the presence of a phosphorus-based ligand of formula (III) or formula (IIIA) or a mixture thereof, in a hydrocyanation reaction milieu comprising water, the ligands having respective formulas:

a bidentate phosphorus-based ligand of formula (III)

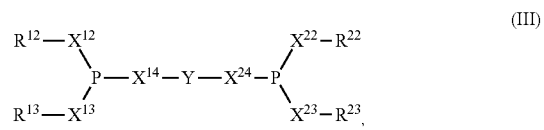

(III)

or,
a tridentate phosphorus-based ligand of formula (IIIA)

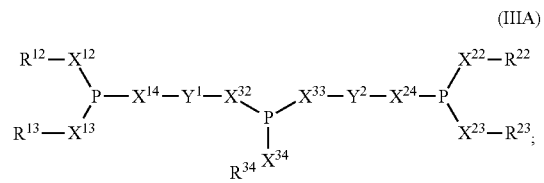

(IIIA)

wherein for the ligand of formula (III), $X^{12}$, $X^{13}$, $X^{14}$, $X^{22}$, $X^{23}$, and $X^{24}$, each independently is oxygen or a bond, provided that at least one of $X^{12}$, $X^{13}$, $X^{14}$, $X^{22}$, $X^{23}$, or $X^{24}$ is oxygen, and for the ligand of formula (IIIA), $X^{12}$, $X^{13}$, $X^{14}$, $X^{22}$, $X^{23}$, $X^{24}$, $X^{32}$, $X^{33}$, and $X^{34}$, each independently is oxygen or a bond, provided that at least one of $X^{12}$, $X^{13}$, $X^{14}$, $X^{22}$, $X^{23}$, $X^{24}$, $X^{32}$, $X^{33}$, or $X^{34}$ is oxygen;

for the ligand of formula (III), $R^{12}$, $R^{13}$, $R^{22}$, and $R^{23}$, and for the ligand of formula (IIIA), $R^{12}$, $R^{13}$, $R^{22}$, $R^{23}$, and $R^{34}$, each independently is (C1-C10)alkyl, (C3-C10)cycloalkyl, (C3-C10)cycloalkyl(C1-C10)alkyl, (C6-C20)aryl, or (C6-C20)aryl(C1-C10)alkyl, wherein for any (C6-C20)aryl or (C6-C20)aryl(C1-C10)alkyl of $R^{12}$, $R^{13}$, $R^{22}$, $R^{23}$, or $R^{34}$, each ring thereof is unsubstituted or is substituted with 1-4 substituents independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, and (C6-C20)aryl(C1-C10)alkyl; or, optionally, one or more of pairs $R^{12}$ and $R^{13}$ or $R^{22}$ and $R^{23}$ are mutually directly bonded, such that the $R^{12}X^{12}$ and $R^{13}X^{13}$ groups, or the $R^{22}X^{22}$ and $R^{23}X^{23}$ groups, or both, together with the respective phosphorus atom to which each pair of groups is bonded, forms a respective ring;

for the ligand of formula (III) the group Y, and for the ligand of formula (IIIA), the groups $Y^1$ and $Y^2$ independently, is an (C6-C20)arylene group, wherein each ring thereof is independently unsubstituted or is independently substituted with 1-4 (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, (C6-C20)aryl(C1-C10)alkyl, fluorine, chlorine, bromine, or (C1-C10)haloalkyl;

the process comprising adding to said reaction mixture before or during said hydrocyanation therewith a stabilizing amount of one or more monodentate phosphorus-based ligand of formula (IV)

$P(X^1R^1)(X^2R^2)(X^3R^3)$      (IV)

wherein $X^1$, $X^2$ and $X^3$ are each independently oxygen or a single bond, provided that at least one of $X^1$, $X^2$, or $X^3$ is an oxygen; and $R^1$, $R^2$ and $R^3$ is each independently (C1-C10)alkyl, (C3-C10)cycloalkyl, (C3-C10)cycloalkyl(C1-C10)alkyl, (C6-C20)aryl, or (C6-C20)aryl(C1-C10)alkyl, wherein for any (C6-C20)aryl or (C6-C20)aryl(C1-C10)alkyl of $R^1$, $R^2$, or $R^3$ each ring thereof is independently unsubstituted or is substituted with 1-4 substituents independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, and (C6-C20)aryl(C1-C10)alkyl; or, optionally, any two of $R^1$, $R^2$, or $R^3$ are directly bonded to each other such that any pair of $R^1X^1$, $R^2X^2$, and $R^3X^3$ groups, together with the phosphorus atom to which they are bonded, forms a ring;

wherein a molar ration of the ligan of formula (IV) that is added to the ligand of formula (III) or formula (IIIA) or mixture thereof, is at least 0.01:1;

wherein the monodentate ligand of formula (IV) has a rate of hydrolysis greater than a rate of hydrolysis of a bidentate ligand of formula (III) or a tridentate ligand of formula (IIIA) or a mixture thereof, in the presence of water in a hydrocyanation reaction milieu optionally further comprising an organic component, under conditions of concentration, temperature, and time sufficient to bring about hydrolysis of the monodentate ligand of formula (IV).

18. The process of claim 17, wherein the one or more monodentate ligand of formula (IV) is produced as a byproduct in a synthetic process for the production of the bidentate ligand of Formula (III) or the tridentate ligand of formula (IIIA) or both.

19. The process of claim 17 wherein the monodentate ligand of formula (IV) is a ligand of formula (XIII):

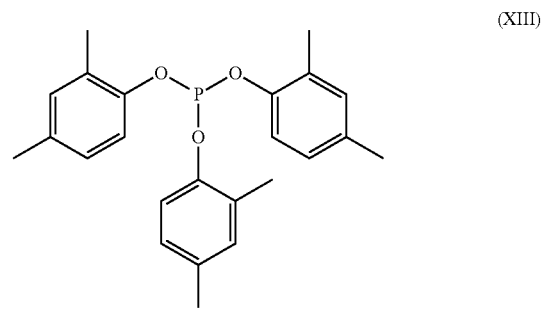

(XIII)

or the ligand of formula (XIV):

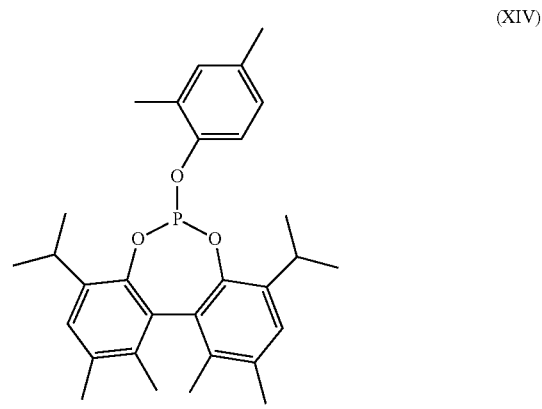 [SMILES: Cc1ccc(Op2oc3c(C(C)C)cc(C)c(C)c3c3c(C)c(C)cc(C(C)C)c3o2)c(C)c1]

(XIV)

or a mixture thereof.

20. The process of claim 17, wherein a molar ratio of the ligand of formula (IV) that is admixed to the ligand of formula (III) or formula (IIIA) or mixture thereof is from about 0.01 to 2.

21. The process of claim 17, wherein the ligand of formula (IV) is of formula (XIII) or (XIV).

22. The process of claim 21, wherein a mixture of the ligands of formula (XIII) and of formula (XIV) are admixed.

23. The process of claim 17, wherein for the ligand of formula (III) or formula (IIIA) or formula (IV), each respective $R^1$, $R^2$, $R^3$, $R^{12}$, $R^{13}$, $R^{22}$, $R^{23}$ or $R^{34}$ is each an independently selected (C6-C20)aryl group, wherein each ring thereof is independently unsubstituted or is substituted with 1-4 substituents independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl and (C6-C20)aryl(C1-C10)alkyl, or wherein any one or more pair of $R^1$ and $R^2$, or $R^{12}$ and $R^{13}$, or $R^{22}$ and $R^{23}$, is directly mutually bonded such that any mutually bonded pair, together with the respective $X^1$, $X^2$, $X^{12}$, $X^{13}$, $X^{22}$ or $X^{23}$ groups and the phosphorus atom to which they are bonded, forms a ring.

24. The process of claim 17, wherein each independently selected $R^1$, $R^2$, $R^3$, $R^{12}$, $R^{13}$, $R^{22}$, $R^{23}$ or $R^{34}$ is a group of formula (II)

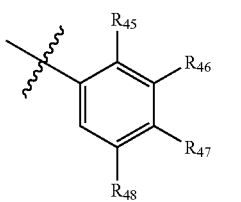

wherein a wavy line indicates a point of attachment; and wherein $R^{45}$ is independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, and (C6-C20)aryl, and each of $R^{46}$, $R^{47}$ and $R^{48}$ is independently selected from the group consisting of H, (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, and (C6-C20)aryl.

25. The process of claim 16 wherein Y, or independently selected $Y^1$ or $Y^2$, is a (C6-C20)arylene group, wherein each ring thereof is independently unsubstituted or is substituted with 1-4 (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, (C6-C20)aryl(C1-C10)alkyl, fluorine, chlorine, bromine, or (C1-C10)haloalkyl.

26. The process of claim 17, wherein the ligand of formula (III) is of formula (X):

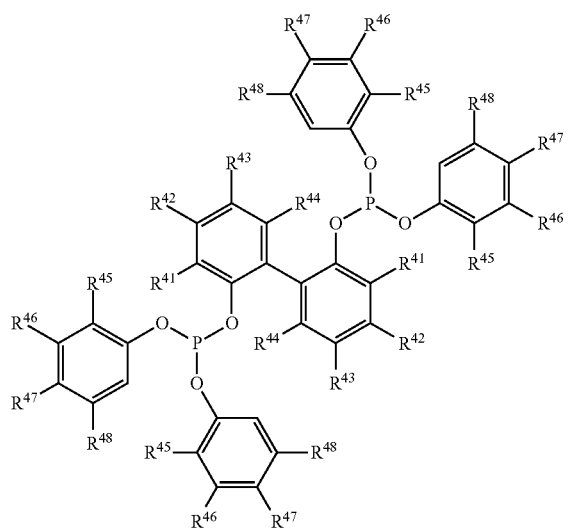

wherein each $R^{41}$ and $R^{45}$ is independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, and (C3-C10)cycloalkoxy(C1-C10)alkoxy, and each of $R^{42}$, $R^{43}$, $R^{44}$, $R^{46}$, $R^{47}$ and $R^{48}$ is independently selected from the group consisting of H, (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, and (C3-C10)cycloalkoxy(C1-C10)alkoxy.

27. The process of claim 26, wherein for the ligand of formula (X),
$R^{41}$ is methyl, ethyl, isopropyl, or cyclopentyl;
$R^{42}$ is H or methyl;
$R^{43}$ is H or (C1-C4)alkyl;
$R^{44}$ is H or methyl;
$R^{45}$ is methyl, ethyl, or isopropyl; and
$R^{46}$, $R^{47}$ and $R^{48}$ are independently H or (C1-C4)alkyl.

28. The process of claim 17, wherein the ligand of formula (III) is of formula (VII):

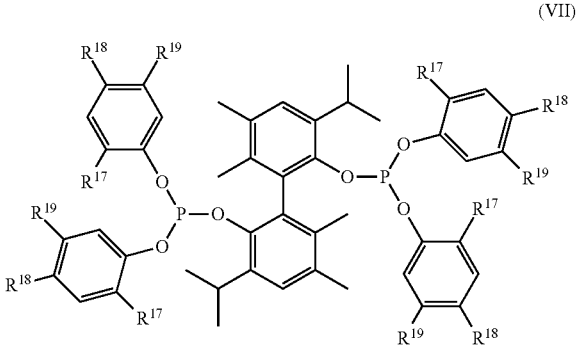

wherein $R^{17}$ is methyl, ethyl, or iso-propyl, and $R^{18}$ and $R^{19}$ are independently H or methyl.

29. The process of claim 17, wherein the ligand of formula (III) is of formula (XII)

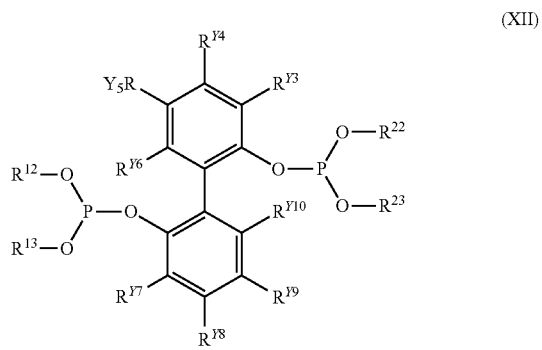

wherein $R^{12}$, $R^{13}$, $R^{22}$ and $R^{23}$ are each independently an unsubstituted or a substituted monovalent aryl, and each of $R^{Y3}$-$R^{Y10}$ is independently selected from the group consisting of hydrogen, (C1-C10) alkyl, and (C1-C10)alkoxy, or wherein two adjacent $R^{Y3}$-$R^{Y10}$ groups together form an optionally substituted fused aryl ring.

30. The process of claim 29, wherein $R^{12}$, $R^{13}$, $R^{22}$, and $R^{23}$ are each independently phenyl substituted at a respective single ortho-position with a (C1-C10)alkyl or (C1-C10)alkoxy, wherein respective meta- and para-positions of the $R^{12}$, $R^{13}$, $R^{22}$, and $R^{23}$ phenyls can each independently be unsubstituted or be independently substituted with (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, or (C3-C10)cycloalkoxy(C1-C10)alkoxy;

$R^{Y6}$ and $R^{Y10}$ are independently (C1-C10)alkyl or (C1-C10)alkoxy, and $R^{Y3}$, $R^{Y4}$, $R^{Y5}$, $R^{Y7}$, $R^{Y8}$, and $R^{Y9}$, are independently H, (C1-C10)alkyl, or (C1-C10)alkoxy, provided that at least one of $R^{Y3}$, $R^{Y4}$, or $R^{Y5}$, and at least one of $R^{Y7}$, $R^{Y8}$, or $R^{Y9}$, is (C1-C10)alkyl or (C1-C10)alkoxy.

31. The process of claim 17, wherein the ligand of formula (III) is of formula (V):

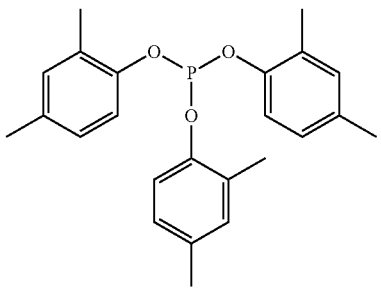

(V)

32. The process of claim 17 wherein the one or more monodentate ligand of formula (IV) is independently of formula (IVA)

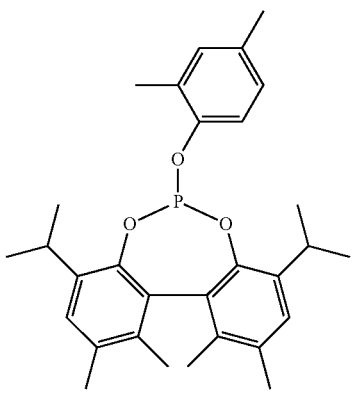

(IVA)

wherein each R is independently methyl or hydrogen, and each n is independently 0, 1, or 2.

33. The process of claim 17, wherein a molar ratio of the ligand or mixture thereof of formula (IV) that is admixed to the ligand of formula (III) or formula (IIIA) or mixture thereof is at least 0.01.

34. The process of claim 17, wherein a molar ratio of the ligand or mixture thereof of formula (IV) that is admixed to the ligand of formula (III) or formula (IIIA) or mixture thereof is from 0.01 to 2.

35. The process of claim 17 wherein the ligand or mixture thereof of formula (IV) is of formula (XIII)

(XIII)

or is of formula (XIV)

(XIV)

or is a mixture thereof.

36. The process of claim 35 wherein ligand or mixture thereof of formula (IV) is a mixture of the ligand of formula (XIII) and the ligand of formula (XIV).

37. The process of claim 17 wherein the reaction mixture is a batch or a continuous process reaction mixture.

38. The process of claim 17 wherein the admixing is done during the hydrocyanation reaction process.

39. A reaction mixture resulting from the process of claim 1, the reaction mixture comprising a phosphorus-based ligand of formula (III) or formula (IIIA) or a mixture thereof, the ligands having respective formulas:

a bidentate phosphorus-based ligand of formula (III)

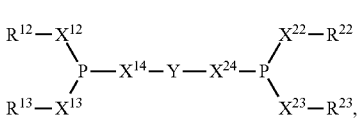

(III)

or, a tridentate phosphorus-based ligand of formula (IIIA)

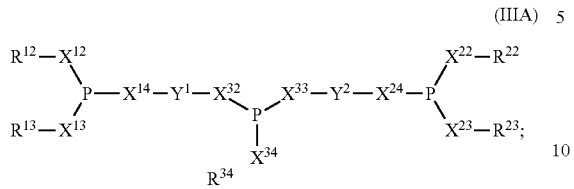

(IIIA)

wherein for the ligand of formula (III), $X^{12}$, $X^{13}$, $X^{14}$, $X^{22}$, $X^{23}$, and $X^{24}$, each independently is oxygen or a bond, provided that at least one of $X^{12}$, $X^{13}$, $X^{14}$, $X^{22}$, $X^{23}$, or $X^{24}$ is oxygen, and for the ligand of formula (IIIA), $X^{12}$, $X^{13}$, $X^{14}$, $X^{22}$, $X^{23}$, $X^{24}$, $X^{32}$, $X^{33}$, and $X^{34}$, each independently is oxygen or a bond, provided that at least one of $X^{12}$, $X^{13}$, $X^{14}$, $X^{22}$, $X^{23}$, $X^{24}$, $X^{32}$, $X^{33}$, or $X^{34}$ is oxygen;

for the ligand of formula (III), $R^{12}$, $R^{13}$, $R^{22}$, and $R^{23}$, and for the ligand of formula (IIIA), $R^{12}$, $R^{13}$, $R^{22}$, $R^{23}$, and $R^{34}$, each independently is (C1-C10)alkyl, (C3-C10)cycloalkyl, (C3-C10)cycloalkyl(C1-C10)alkyl, (C6-C20)aryl, or (C6-C20)aryl(C1-C10)alkyl, wherein for any (C6-C20)aryl or (C6-C20)aryl(C1-C10)alkyl of $R^{12}$, $R^{13}$, $R^{22}$, $R^{23}$, or $R^{34}$, each ring thereof is unsubstituted or is substituted with 1-4 substituents independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, and (C6-C20)aryl(C1-C10)alkyl;

or, optionally, one or more of pairs $R^{12}$ and $R^{13}$ or $R^{22}$ and $R^{23}$ are mutually directly bonded, such that the $R^{12}X^{12}$ and $R^{13}X^{13}$ groups, or the $R^{22}X^{22}$ and $R^{23}X^{23}$ groups, or both, together with the respective phosphorus atom to which each pair of groups is bonded, forms a respective ring;

for the ligand of formula (III) the group Y, and for the ligand of formula (IIIA), the groups $Y^1$ and $Y^2$ independently, is an (C6-C20)arylene group, wherein each ring thereof is independently unsubstituted or is substituted with 1-4 (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, (C6-C20)aryl(C1-C10)alkyl, fluorine, chlorine, bromine, or (C1-C10)haloalkyl;

and further comprising an amount of one of more monodentate phosphorus-based ligand of formula (IV)

$$P(X^1R^1)(X^2R^2)(X^3R^3) \quad (IV)$$

wherein $X^1$, $X^2$ and $X^3$ are each independently oxygen or a single bond, provided that at least one of $X^1$, $X^2$, or $X^3$ is an oxygen; and $R^1$, $R^2$ and $R^3$ is each independently (C1-C10)alkyl, (C3-C10)cycloalkyl, (C3-C10)cycloalkyl(C1-C10)alkyl, (C6-C20)aryl, or (C6-C20)aryl(C1-C10)alkyl, wherein for any (C6-C20)aryl or (C6-C20)aryl(C1-C10)alkyl of $R^1$, $R^2$, or $R^3$ each ring thereof is independently unsubstituted or is substituted with 1-4 substituents independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy (C1-C10)alkyl, (C3-C10)cycloalkyl(C1-C10)alkoxy, (C3-C10)cycloalkoxy(C1-C10)alkoxy, (C6-C20)aryl, and (C6-C20)aryl(C1-C10)alkyl; or, optionally, any two of $R^1$, $R^2$, or $R^3$ are directly bonded to each other such that any pair of $R^1X^1$, $R^2X^2$, and $R^3X^3$ groups, together with the phosphorus atom to which they are bonded, forms a ring;

wherein a smaller proportion of the ligand of formula (IV) relative to the ligand of formula (III) or formula (IIIA) or mixture thereof, is present than the proportion of the ligand of formula (IV) relative to the ligand of formula (III) or formula (IIIA) or mixture thereof, that was present before the catalytic hydrocyanation reaction was commenced.

40. The reaction mixture of claim 39 wherein the one or more monodentate ligand of formula (IV) is produced as a byproduct in a synthetic process for the production of the bidentate ligand of Formula (III) or the tridentate ligand of formula (IIIA) or both.

41. The mixture of claim 39 wherein the monodentate ligand of formula (IV) is a ligand of formula (XIII):

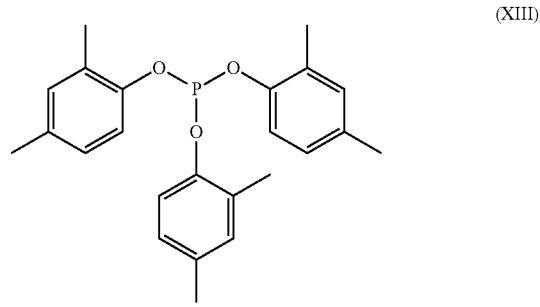

(XIII)

or a ligand of formula (XIV):

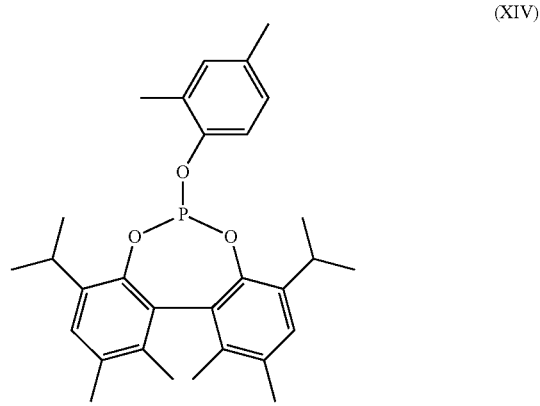 [SMILES: Cc1ccc(Op2oc3c(C(C)C)cc(C)c(C)c3c3c(C)c(C)cc(C(C)C)c3o2)c(C)c1]

(XIV)

or is a mixture thereof.

42. The mixture of claim 39, wherein a molar ratio of the ligand of formula (IV) that is admixed to the ligand of formula (III) or formula (IIIA) or mixture thereof, is at least 0.01, and, optionally, is no greater than 2.

43. The mixture of claim 39 wherein the one or more monodentate ligand of formula (IV) is independently of formula (IVA)

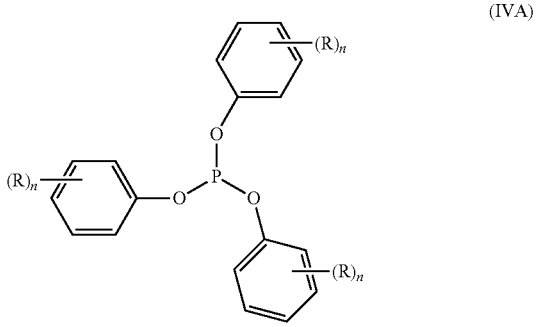

wherein each R is methyl and each n is independently 0, 1, or 2.

44. The mixture of claim 39, wherein the ligand of formula (IV) is of formula (XIII) or (XIV).

45. The mixture of claim 44, wherein a mixture of the ligands of formula (XIII) and of formula (XIV) are admixed.

46. The mixture of claim 39, wherein for the ligand of formula (III) or formula (IIIA) or formula (IV), each respective $R^1$, $R^2$, $R^3$, $R^{12}$, $R^{13}$, $R^{22}$, $R^{23}$ or $R^{34}$ is each an independently selected (C6-C20)aryl group, wherein each ring thereof is independently unsubstituted or is substituted with 1-4 substituents independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl and (C6-C20)aryl(C1-C10)alkyl, or wherein any one or more pair of $R^1$ and $R^2$, or $R^{12}$ and $R^{13}$, or $R^{22}$ and $R^{23}$, is directly mutually bonded such that any mutually bonded pair, together with the respective $X^1$, $X^2$, $X^{12}$, $X^{13}$, $X^{22}$ or $X^{23}$ groups and the phosphorus atom to which they are bonded, forms a ring.

47. The mixture of claim 39, wherein each independently selected $R^1$, $R^2$, $R^3$, $R^{12}$, $R^{13}$, $R^{22}$, $R^{23}$ or $R^{34}$ is a group of formula (II)

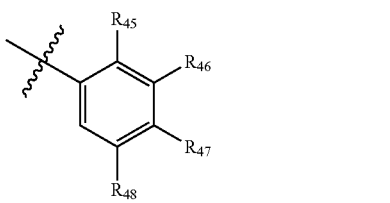

wherein a wavy line indicates a point of attachment; and wherein $R^{45}$ is independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, and (C6-C20)aryl, and each of $R^{46}$, $R^{47}$ and $R^{48}$ is independently selected from the group consisting of H, (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl (C1-C10)alkoxy, (C3-C10)cycloalkoxy(C1-C10)alkoxy, and (C6-C20)aryl.

48. The mixture of claim 39 wherein Y, or independently selected $Y^1$ or $Y^2$, is a (C6-C20)arylene group, wherein each ring thereof is independently unsubstituted or is substituted with 1-4 (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, (C6-C20)aryl(C1-C10)alkyl, fluorine, chlorine, bromine, or (C1-C10)haloalkyl.

49. The mixture of claim 39, wherein the ligand of formula (III) is of formula (X):

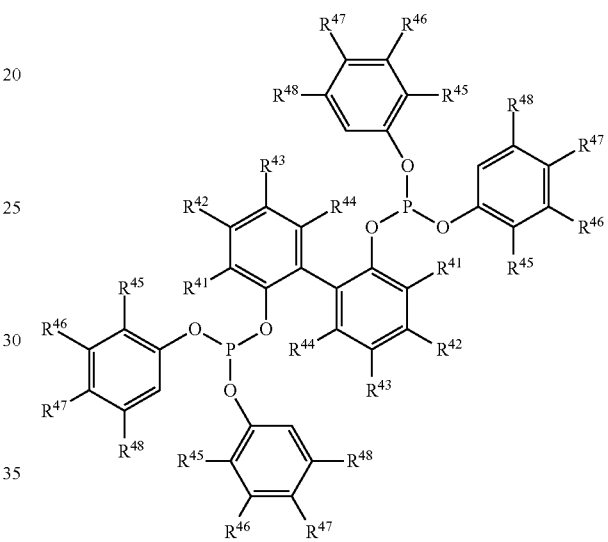

wherein each $R^{41}$ and $R^{45}$ is independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, and (C3-C10)cycloalkoxy(C1-C10)alkoxy, and each of $R^{42}$, $R^{43}$, $R^{94}$, $R^{46}$, $R^{47}$ and $R^{48}$ is independently selected from the group consisting of H, (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, and (C3-C10)cycloalkoxy(C1-C10)alkoxy.

50. The mixture of claim 49, wherein for the ligand of formula (X), $R^{41}$ is methyl, ethyl, isopropyl, or cyclopentyl;

$R^{42}$ is H or methyl;

$R^{43}$ is H or (C1-C4)alkyl;

$R^{44}$ is H or methyl;

$R^{45}$ is methyl, ethyl, or isopropyl; and $R^{46}$, $R^{47}$ and $R^{48}$ are independently H or (C1-C4)alkyl.

51. The mixture of claim 39, wherein the ligand of formula (III) is of formula (VII):

(VII)

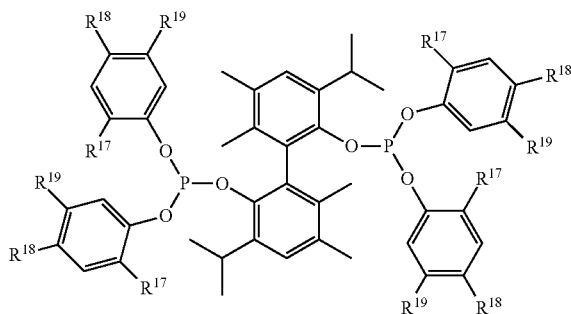

wherein $R^{17}$ is methyl, ethyl, or iso-propyl, and $R^{18}$ and $R^{19}$ are independently H or methyl.

52. The mixture of claim 39, wherein the ligand of formula (III) is of formula (XII)

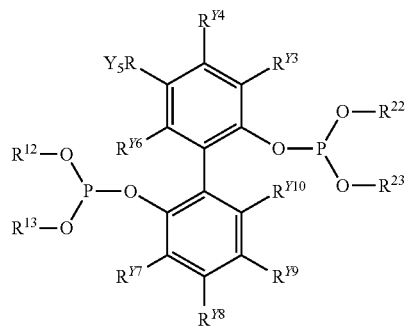

(XII)

wherein $R^{12}$, $R^{13}$, $R^{22}$ and $R^{23}$ are each independently an unsubstituted or a substituted monovalent aryl, and each of $R^{Y3}$-$R^{Y10}$ is independently selected from the group consisting of hydrogen, (C1-C10) alkyl, and (C1-C10)alkoxy, or wherein two adjacent $R^{Y3}$-$R^{Y10}$ groups together form an optionally substituted fused aryl ring.

53. The mixture of claim 52, wherein $R^{12}$, $R^{13}$, $R^{22}$, and $R^{23}$ are each independently phenyl substituted at a respective single ortho-position with a (C1-C10)alkyl or (C1-C10) alkoxy, wherein respective meta- and para-positions of the $R^{12}$, $R^{13}$, $R^{22}$, and $R^{23}$ phenyls can each independently be unsubstituted or be independently substituted with (C1-C10) alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, or (C3-C10)cycloalkoxy(C1-C10)alkoxy;

$R^{Y6}$ and $R^{Y10}$ are independently (C1-C10)alkyl or (C1-C10)alkoxy, and $R^{Y3}$, $R^{Y4}$, $R^{Y5}$, $R^{Y7}$, $R^{Y8}$, and $R^{Y9}$, are independently H, (C1-C10)alkyl, or (C1-C10)alkoxy, provided that at least one of $R^{Y3}$, $R^{Y4}$, or $R^{Y5}$, and at least one of $R^{Y7}$, $R^{Y8}$, or $R^{Y9}$, is (C1-C10)alkyl or (C1-C10)alkoxy.

54. The mixture of claim 39, wherein the ligand of formula (III) is of formula (V):

(V)

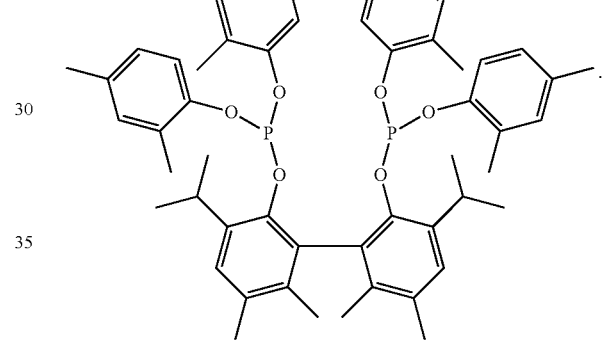

\* \* \* \* \*

UNITED STATES PATENT AND TRADEMARK OFFICE
CERTIFICATE OF CORRECTION

PATENT NO. : 9,834,505 B2
APPLICATION NO. : 14/404068
DATED : December 5, 2017
INVENTOR(S) : Aki et al.

It is certified that error appears in the above-identified patent and that said Letters Patent is hereby corrected as shown below:

On the Title Page

Item (57), in "Abstract", in Column 2, Line 11, delete "C6-C20" and insert --$C_6$-$C_{20}$-- therefor In the Claims In Column 47, Lines 33-36, in Claim 1, delete "(C1-C10)alkyl, (C3-C10)cycloalkyl, (C3-C10)cycloalkyl(C1-C10)alkyl, (C6-C20)aryl, or (C6-C20)aryl(C1-C10)alkyl, wherein for any (C6-C20)aryl or (C6-C20)aryl(C1-C10)alkyl of" and insert --$(C_1$-$C_{10})$alkyl, $(C_3$-$C_{10})$cycloalkyl, $(C_3$-$C_{10})$cycloalkyl$(C_1$-$C_{10})$alkyl, $(C_6$-$C_{20})$aryl, or $(C_6$-$C_{20})$aryl$(C_1$-$C_{10})$alkyl, wherein for any $(C_6$-$C_{20})$aryl or $(C_6$-$C_{20})$aryl$(C_1$-$C_{10})$alkyl of-- therefor In Column 47, Lines 39-45, in Claim 1, delete "(C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, and (C6-C20)aryl(C1-C10)alkyl;" and insert --$(C_1$-$C_{10})$alkyl, $(C_3$-$C_{10})$cycloalkyl, $(C_1$-$C_{10})$alkoxy, $(C_3$-$C_{10})$cycloalkoxy, $(C_3$-$C_{10})$cycloalkyl$(C_1$-$C_{10})$alkyl, $(C_3$-$C_{10})$cycloalkoxy$(C_1$-$C_{10})$alkyl, $(C_3$-$C_{10})$cycloalkyl$(C_1$-$C_{10})$alkoxy, $(C_3$-$C_{10})$cycloalkoxy$(C_1$-$C_{10})$alkoxy, $(C_6$-$C_{20})$aryl, and $(C_6$-$C_{20})$aryl$(C_1$-$C_{10})$alkyl;-- therefor In Column 47, Line 53, in Claim 1, delete "(C6-C20)arylene" and insert --$(C_6$-$C_{20})$arylene-- therefor In Column 47, Lines 55-61, in Claim 1, delete "(C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, (C6-C20)aryl(C1-C10)alkyl, fluorine, chlorine, bromine, or (C1-C10)haloalkyl;" and insert --$(C_1$-$C_{10})$alkyl, $(C_3$-$C_{10})$cycloalkyl, $(C_1$-$C_{10})$alkoxy, $(C_3$-$C_{10})$cycloalkoxy, $(C_3$-$C_{10})$cycloalkyl$(C_1$-$C_{10})$alkyl, $(C_3$-$C_{10})$cycloalkoxy$(C_1$-$C_{10})$alkyl, $(C_3$-

Signed and Sealed this
Thirteenth Day of August, 2019

Andrei Iancu
*Director of the United States Patent and Trademark Office*

$C_{10}$)cycloalkyl($C_1$-$C_{10}$)alkoxy, ($C_3$-$C_{10}$)cycloalkoxy($C_1$-$C_{10}$)alkoxy, ($C_6$-$C_{20}$)aryl, ($C_6$-$C_{20}$)aryl($C_1$-$C_{10}$)alkyl, fluorine, chlorine, bromine, or ($C_1$-$C_{10}$)haloalkyl;-- therefor In Column 48, Lines 4-7, in Claim 1, delete "(C1-C10)alkyl, (C3-C10)cycloalkyl, (C3-C10)cycloalkyl(C1-C10)alkyl, (C6-C20)aryl, or (C6-C20)aryl(C1-C10)alkyl, wherein for any (C6-C20)aryl or (C6-C20)aryl(C1-C10)alkyl" and insert --($C_1$-$C_{10}$)alkyl, ($C_3$-$C_{10}$)cycloalkyl, ($C_3$-$C10$)cycloalkyl($C_1$-$C_{10}$)alkyl, ($C_6$-$C_{20}$)aryl, or ($C_6$-$C_{20}$)aryl($C_1$-$C_{10}$)alkyl, wherein for any ($C_6$-$C_{20}$)aryl or ($C_6$-$C_{20}$)aryl($C_1$-$C_{10}$)alkyl-- therefor In Column 48, Lines 10-15, in Claim 1, delete "(C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, and (C6-C20)aryl(C1-C10)alkyl;" and insert --($C_1$-$C_{10}$)alkyl, ($C_3$-$C_{10}$)cycloalkyl, ($C_1$-$C_{10}$)alkoxy, ($C_3$-$C_{10}$)cycloalkoxy, ($C_3$-$C_{10}$)cycloalkyl($C_1$-$C_{10}$)alkyl, ($C_3$-$C_{10}$)cycloalkoxy($C_1$-$C_{10}$)alkyl, ($C_3$-$C_{10}$)cycloalkyl($C_1$-$C_{10}$)alkoxy, ($C_3$-$C_{10}$)cycloalkoxy($C_1$-$C_{10}$)alkoxy, ($C_6$-$C_{20}$)aryl, and ($C_6$-$C_{20}$)aryl($C_1$-$C_{10}$)alkyl;-- therefor In Column 48, Line 47, in Claim 2, delete "Formula" and insert --formula-- therefor In Column 49, Line 23, in Claim 4, delete "formula (iII)" and insert --formula (III)-- therefor In Column 49, Line 24, in Claim 4, delete "and, optionally," and insert --and-- therefor In Column 49, Line 27, in Claim 5, after "formula (IVA)", insert --:--

In Column 49, Line 51, in Claim 8, delete "(C6-C20)" and insert --($C_6$-$C_{20}$)-- therefor In Column 49, Lines 54-59, in Claim 8, delete "(C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl and (C6-C20)aryl(C1-C10)alkyl," and insert --($C_1$-$C_{10}$)alkyl, ($C_3$-$C_{10}$)cycloalkyl, ($C_1$-$C_{10}$)alkoxy, ($C_3$-$C_{10}$)cycloalkoxy, ($C_3$-$C_{10}$)cycloalkyl($C_1$-$C_{10}$)alkyl, ($C_3$-$C_{10}$)cycloalkoxy($C_1$-$C_{10}$)alkyl, ($C_3$-$C_{10}$)cycloalkyl($C_1$-$C_{10}$)alkoxy, ($C_3$-$C_{10}$)cycloalkoxy($C_1$-$C_{10}$)alkoxy, ($C_6$-$C_{20}$)aryl and ($C_6$-$C_{20}$)aryl($C_1$-$C_{10}$)alkyl,-- therefor In Column 49, Line 67, in Claim 9, after "formula (II)", insert --:--

In Column 50, Formula (II), Lines 1-10, in Claim 9, delete " 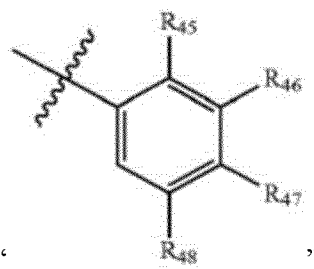 " and insert -- 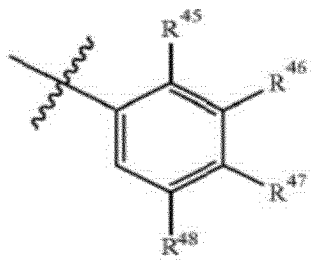 -- therefor In Column 50, Lines 14-18, in Claim 9, delete "(C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, and (C6-C20)aryl," and insert --$(C_1-C_{10})$alkyl, $(C_3-C_{10})$cycloalkyl, $(C_1-C_{10})$alkoxy, $(C_3-C_{10})$cycloalkoxy, $(C_3-C_{10})$cycloalkyl$(C_1-C_{10})$alkyl, $(C_3-C_{10})$cycloalkoxy$(C_1-C_{10})$alkyl, $(C_3-C_{10})$cycloalkyl$(C_1-C_{10})$alkoxy, $(C_3-C_{10})$cycloalkoxy$(C_1-C_{10})$alkoxy, and $(C_6-C_{20})$aryl,-- therefor In Column 50, Line 19, in Claim 9, delete "$R^{48}$," and insert --$R^{46}$,-- therefor In Column 50, Lines 20-25, in Claim 9, delete "(C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, and (C6-C20)aryl." and insert --$(C_1-C_{10})$alkyl, $(C_3-C_{10})$cycloalkyl, $(C_1-C_{10})$alkoxy, $(C_3-C_{10})$cycloalkoxy, $(C_3-C_{10})$cycloalkyl$(C_1-C_{10})$alkyl, $(C_3-C_{10})$cycloalkoxy$(C_1-C_{10})$alkyl, $(C_3-C_{10})$cycloalkyl$(C_1-C_{10})$alkoxy, $(C_3-C_{10})$cycloalkoxy$(C_1-C_{10})$alkoxy, and $(C_6-C_{20})$aryl.-- therefor In Column 50, Line 27, in Claim 10, delete "(C6-C20)arylene" and insert --$(C_6-C_{20})$arylene-- therefor In Column 50, Lines 29-34, in Claim 10, delete "(C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, (C6-C20)aryl(C1-C10)alkyl, fluorine, chlorine, bromine, or (C1-C10)haloalkyl." and insert --$(C_1-C_{10})$alkyl, $(C_3-C_{10})$cycloalkyl, $(C_1-C_{10})$alkoxy, $(C_3-C_{10})$cycloalkoxy, $(C_3-C_{10})$cycloalkyl$(C_1-C_{10})$alkyl, $(C_3-C_{10})$cycloalkoxy$(C_1-C_{10})$alkyl, $(C_3-C_{10})$cycloalkyl$(C_1-C_{10})$alkoxy, $(C_3-C_{10})$cycloalkoxy$(C_1-C_{10})$alkoxy, $(C_6-C_{20})$aryl, $(C_6-C_{20})$aryl$(C_1-C_{10})$alkyl, fluorine, chlorine, bromine, or $(C_1-C_{10})$haloalkyl.-- therefor

CERTIFICATE OF CORRECTION (continued)
U.S. Pat. No. 9,834,505 B2

In Column 50, Formula (X), Lines 40-60, in Claim 11, delete

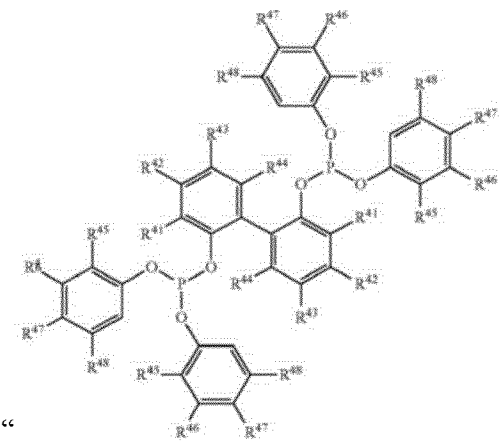

" and insert --

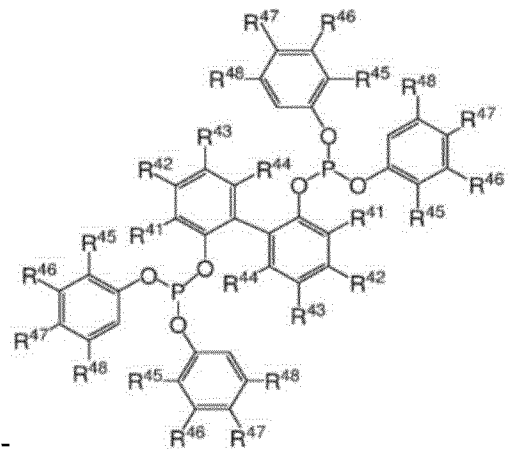

-- therefor

In Column 50, Lines 63-67, in Claim 11, delete "(C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, and (C3-C10)cycloalkoxy(C1-C10)alkoxy," and insert --$(C_1-C_{10})$alkyl, $(C_3-C_{10})$cycloalkyl, $(C_1-C_{10})$alkoxy, $(C_3-C_{10})$cycloalkoxy, $(C_3-C_{10})$cycloalkyl$(C_1-C_{10})$alkyl, $(C_3-C_{10})$cycloalkoxy$(C_1-C_{10})$alkyl, $(C_3-C_{10})$cycloalkyl$(C_1-C_{10})$alkoxy, and $(C_3-C_{10})$cycloalkoxy$(C_1-C_{10})$alkoxy,-- therefor In Column 51, Lines 2-6, in Claim 11, delete "(C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, and (C3-C10)cycloalkoxy(C1-C10)alkoxy." and insert --$(C_1-C_{10})$alkyl, $(C_3-C_{10})$cycloalkyl, $(C_1-C_{10})$alkoxy, $(C_3-C_{10})$cycloalkoxy, $(C_3-C_{10})$cycloalkyl$(C_1-C_{10})$alkyl, $(C_3-C_{10})$cycloalkoxy$(C_1-C_{10})$alkyl, $(C_3-C_{10})$cycloalkyl$(C_1-C_{10})$alkoxy, and $(C_3-C_{10})$cycloalkoxy$(C_1-C_{10})$alkoxy.-- therefor In Column 51, Line 11, in Claim 12, delete "(C1-C4)alkyl;" and insert --$(C_1-C_4)$alkyl;-- therefor In Column 51, Line 14, in Claim 12, delete "(C1-C4)alkyl." and insert --$(C_1-C_4)$alkyl.-- therefor In Column 51, Line 37, in Claim 14, after "formula (XII)", insert --:--

In Column 51, Formula (XII), Lines 40-54, in Claim 14, delete

" 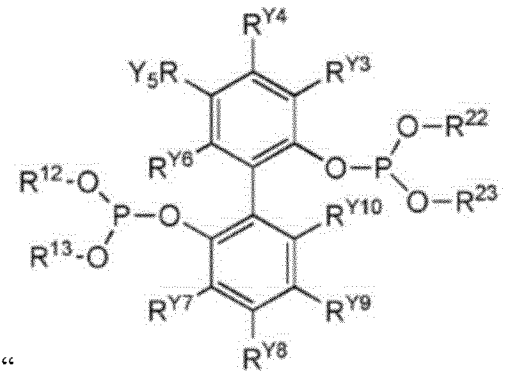 " and insert -- 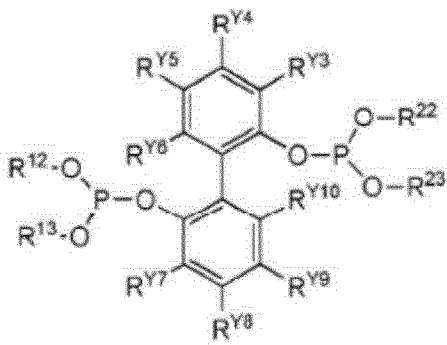 --
therefor

In Column 51, Line 58, in Claim 14, delete "(C1-C10) alkyl, and (C1-C10)alkoxy," and insert
--$(C_1-C_{10})$alkyl, and $(C_1-C_{10})$alkoxy,-- therefor In Column 51, Lines 63-64, in Claim 15, delete "(C1-C10)alkyl or (C1-C10)alkoxy," and insert
--$(C_1-C_{10})$alkyl or $(C_1-C_{10})$alkoxy,-- therefor In Columns 51-52, Lines 66-67 and 1-3, in Claim 15, delete "(C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, or (C3-C10)cycloalkoxy(C1-C10)alkoxy;" and insert --$(C_1-C_{10})$alkyl, $(C_3-C_{10})$cycloalkyl, $(C_1-C_{10})$alkoxy, $(C_3-C_{10})$cycloalkoxy, $(C_3-C_{10})$cycloalkyl$(C_1-C_{10})$alkyl, $(C_3-C_{10})$cycloalkoxy$(C_1-C_{10})$alkyl, $(C_3-C_{10})$cycloalkyl$(C_1-C_{10})$alkoxy, or $(C_3-C_{10})$cycloalkoxy$(C_1-C_{10})$alkoxy;-- therefor In Column 52, Lines 4-5, in Claim 15, delete "(C1-C10)alkyl or (C1-C10)alkoxy," and insert
--$(C_1-C_{10})$alkyl or $(C_1-C_{10})$alkoxy,-- therefor In Column 52, Line 6, in Claim 15, delete "(C1-C10)alkyl, or (C1-C10)alkoxy," and insert
--$(C_1-C_{10})$alkyl or $(C_1-C_{10})$alkoxy,-- therefor In Column 52, Lines 8-9, in Claim 15, delete "(C1-C10)alkyl or (C1-C10)alkoxy." and insert
--$(C_1-C_{10})$alkyl or $(C_1-C_{10})$alkoxy.-- therefor In Column 53, Lines 3-6, in Claim 17, delete "(C1-C10)alkyl, (C3-C10)cycloalkyl, (C3-C10)cycloalkyl(C1-C10)alkyl, (C6-C20)aryl, or (C6-C20)aryl(C1-C10)alkyl, wherein for any (C6-C20)aryl or (C6-C20)aryl(C1-C10)alkyl of" and insert --$(C_1-C_{10})$alkyl, $(C_3-C_{10})$cycloalkyl, $(C_3-C_{10})$cycloalkyl$(C_1-C_{10})$alkyl, $(C_6-C_{20})$aryl, or $(C_6-C_{20})$aryl$(C_1-C_{10})$alkyl, wherein for any $(C_6-C_{20})$aryl or $(C_6-C_{20})$aryl$(C_1-C_{10})$alkyl of-- therefor In Column 53, Lines 9-15, in Claim 17, delete "(C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, and (C6-C20)aryl(C1-C10)alkyl;" and insert --$(C_1-C_{10})$alkyl, $(C_3-C_{10})$cycloalkyl, $(C_1-C_{10})$alkoxy, $(C_3-C_{10})$cycloalkoxy, $(C_3-C_{10})$cycloalkyl$(C_1-C_{10})$alkyl, $(C_3-

$C_{10}$)cycloalkoxy($C_1$-$C_{10}$)alkyl, ($C_3$-$C_{10}$)cycloalkyl($C_1$-$C_{10}$)alkoxy, ($C_3$-$C_{10}$)cycloalkoxy($C_1$-$C_{10}$)alkoxy, ($C_6$-$C_{20}$)aryl, and ($C_6$-$C_{20}$)aryl($C_1$-$C_{10}$)alkyl;-- therefor In Column 53, Line 24, in Claim 17, delete "(C6-C20)arylene" and insert --($C_6$-$C_{20}$)arylene-- therefor In Column 53, Lines 26-32, in Claim 17, delete "(C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, (C6-C20)aryl(C1-C10)alkyl, fluorine, chlorine, bromine, or (C1-C10)haloalkyl;" and insert --($C_1$-$C_{10}$)alkyl, ($C_3$-$C_{10}$)cycloalkyl, ($C_1$-$C_{10}$)alkoxy, ($C_3$-$C_{10}$)cycloalkoxy, ($C_3$-$C_{10}$)cycloalkyl($C_1$-$C_{10}$)alkyl, ($C_3$-$C_{10}$)cycloalkoxy($C_1$-$C_{10}$)alkyl, ($C_3$-$C_{10}$)cycloalkyl($C_1$-$C_{10}$)alkoxy, ($C_3$-$C_{10}$)cycloalkoxy($C_1$-$C_{10}$)alkoxy, ($C_6$-$C_{20}$)aryl, ($C_6$-$C_{20}$)aryl($C_1$-$C_{10}$)alkyl, fluorine, chlorine, bromine, or ($C_1$-$C_{10}$)haloalkyl;-- therefor In Column 53, Lines 43-46, in Claim 17, delete "(C1-C10)alkyl, (C3-C10)cycloalkyl, (C3-C10)cycloalkyl(C1-C10)alkyl, (C6-C20)aryl, or (C6-C20)aryl(C1-C10)alkyl, wherein for any (C6-C20)aryl or (C6-C20)aryl(C1-C10)alkyl" and insert --($C_1$-$C_{10}$)alkyl, ($C_3$-$C_{10}$)cycloalkyl, ($C_3$-$C_{10}$)cycloalkyl($C_1$-$C_{10}$)alkyl, ($C_6$-$C_{20}$)aryl, or ($C_6$-$C_{20}$)aryl($C_1$-$C_{10}$)alkyl, wherein for any ($C_6$-$C_{20}$)aryl or ($C_6$-$C_{20}$)aryl($C_1$-$C_{10}$)alkyl-- therefor In Column 53, Lines 49-54, in Claim 17, delete "(C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, and (C6-C20)aryl(C1-C10)alkyl;" and insert --($C_1$-$C_{10}$)alkyl, ($C_3$-$C_{10}$)cycloalkyl, ($C_1$-$C_{10}$)alkoxy, ($C_3$-$C_{10}$)cycloalkoxy, ($C_3$-$C_{10}$)cycloalkyl($C_1$-$C_{10}$)alkyl, ($C_3$-$C_{10}$)cycloalkoxy($C_1$-$C_{10}$)alkyl, ($C_3$-$C_{10}$)cycloalkyl($C_1$-$C_{10}$)alkoxy, ($C_3$-$C_{10}$)cycloalkoxy($C_1$-$C_{10}$)alkoxy, ($C_6$-$C_{20}$)aryl, and ($C_6$-$C_{20}$)aryl($C_1$-$C_{10}$)alkyl;-- therefor In Column 53, Line 59, in Claim 17, delete "ration of the ligan" and insert --ratio of the ligand-- therefor In Column 54, Line 7, in Claim 18, delete "Formula" and insert --formula-- therefor In Column 54, Line 58, in Claim 23, delete "(C6-C20)aryl" and insert --($C_6$-$C_{20}$)aryl-- therefor In Column 54, Lines 61-65, in Claim 23, delete "(C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl and (C6-C20)aryl(C1-C10)alkyl, or" and insert --($C_1$-$C_{10}$)alkyl, ($C_3$-$C_{10}$)cycloalkyl, ($C_1$-$C_{10}$)alkoxy, ($C_3$-$C_{10}$)cycloalkoxy, ($C_3$-$C_{10}$)cycloalkyl($C_1$-$C_{10}$)alkyl, ($C_3$-$C_{10}$)cycloalkoxy($C_1$-$C_{10}$)alkyl, ($C_3$-$C_{10}$)cycloalkyl($C_1$-$C_{10}$)alkoxy, ($C_3$-$C_{10}$)cycloalkoxy($C_1$-$C_{10}$)alkoxy, ($C_6$-$C_{20}$)aryl and ($C_6$-$C_{20}$)aryl($C_1$-$C_{10}$)alkyl, or-- therefor In Column 55, Line 6, in Claim 24, after "formula (II)", insert --:--

In Column 55, Formula (II), Lines 7-17, in Claim 24, delete " 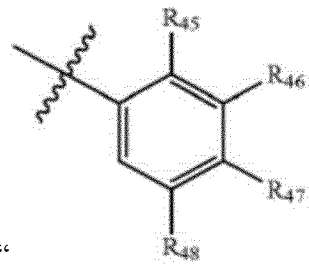 " and insert -- 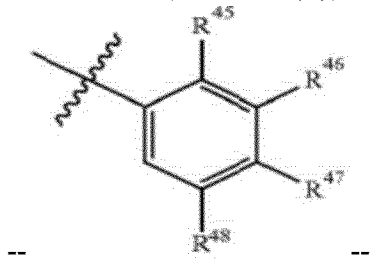 -- therefor In Column 55, Lines 20-24, in Claim 24, delete "(C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, and (C6-C20)aryl," and insert --$(C_1-C_{10})$alkyl, $(C_3-C_{10})$cycloalkyl, $(C_1-C_{10})$alkoxy, $(C_3-C_{10})$cycloalkoxy, $(C_3-C_{10})$cycloalkyl$(C_1-C_{10})$alkyl, $(C_3-C_{10})$cycloalkoxy$(C_1-C_{10})$alkyl, $(C_3-C_{10})$cycloalkyl$(C_1-C_{10})$alkoxy, $(C_3-C_{10})$cycloalkoxy$(C_1-C_{10})$alkoxy, and $(C_6-C_{20})$aryl,-- therefor In Column 55, Lines 26-31, in Claim 24, delete "(C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, and (C6-C20)aryl." and insert --$(C_1-C_{10})$alkyl, $(C_3-C_{10})$cycloalkyl, $(C_1-C_{10})$alkoxy, $(C_3-C_{10})$cycloalkoxy, $(C_3-C_{10})$cycloalkyl$(C_1-C_{10})$alkyl, $(C_3-C_{10})$cycloalkoxy$(C_1-C_{10})$alkyl, $(C_3-C_{10})$cycloalkyl$(C_1-C_{10})$alkoxy, $(C_3-C_{10})$cycloalkoxy$(C_1-C_{10})$alkoxy, and $(C_6-C_{20})$aryl.-- therefor In Column 55, Line 33, in Claim 25, delete "(C6-C20)arylene" and insert --$(C_6-C_{20})$arylene-- therefor In Column 55, Lines 35-40, in Claim 25, delete "(C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, (C6-C20)aryl(C1-C10)alkyl, fluorine, chlorine, bromine, or (C1-C10)haloalkyl." and insert --$(C_1-C_{10})$alkyl, $(C_3-C_{10})$cycloalkyl, $(C_1-C_{10})$alkoxy, $(C_3-C_{10})$cycloalkoxy, $(C_3-C_{10})$cycloalkyl$(C_1-C_{10})$alkyl, $(C_3-C_{10})$cycloalkoxy$(C_1-C_{10})$alkyl, $(C_3-C_{10})$cycloalkyl$(C_1-C_{10})$alkoxy, $(C_3-C_{10})$cycloalkoxy$(C_1-C_{10})$alkoxy, $(C_6-C_{20})$aryl, $(C_6-C_{20})$aryl$(C_1-C_{10})$alkyl, fluorine, chlorine, bromine, or $(C_1-C_{10})$haloalkyl.-- therefor In Column 56, Lines 2-6, in Claim 26, delete "(C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, and (C3-

C10)cycloalkoxy(C1-C10)alkoxy," and insert --$(C_1-C_{10})$alkyl, $(C_3-C_{10})$cycloalkyl, $(C_1-C_{10})$alkoxy, $(C_3-C_{10})$cycloalkoxy, $(C_3-C_{10})$cycloalkyl$(C_1-C_{10})$alkyl, $(C_3-C_{10})$cycloalkoxy$(C_1-C_{10})$alkyl, $(C_3-C_{10})$cycloalkyl$(C_1-C_{10})$alkoxy, and $(C_3-C_{10})$cycloalkoxy$(C_1-C_{10})$alkoxy,-- therefor In Column 56, Lines 8-13, in Claim 26, delete "(C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl (C1-C10)alkoxy, and (C3-C10)cycloalkoxy(C1-C10)alkoxy." and insert --$(C_1-C_{10})$alkyl, $(C_3-C_{10})$cycloalkyl, $(C_1-C_{10})$alkoxy, $(C_3-C_{10})$cycloalkoxy, $(C_3-C_{10})$cycloalkyl$(C_1-C_{10})$alkyl, $(C_3-C_{10})$cycloalkoxy$(C_1-C_{10})$alkyl, $(C_3-C_{10})$cycloalkyl$(C_1-C_{10})$alkoxy, and $(C_3-C_{10})$cycloalkoxy$(C_1-C_{10})$alkoxy.-- therefor In Column 56, Line 18, in Claim 27, delete "(C1-C4)alkyl;" and insert --$(C_1-C_4)$alkyl;-- therefor In Column 56, Line 21, in Claim 27, delete "(C1-C4)alkyl." and insert --$(C_1-C_4)$alkyl.-- therefor In Column 56, Line 44, in Claim 29, after "formula (XII)", insert --:--

In Column 56, Formula (XII), Lines 45-60, in Claim 29, delete

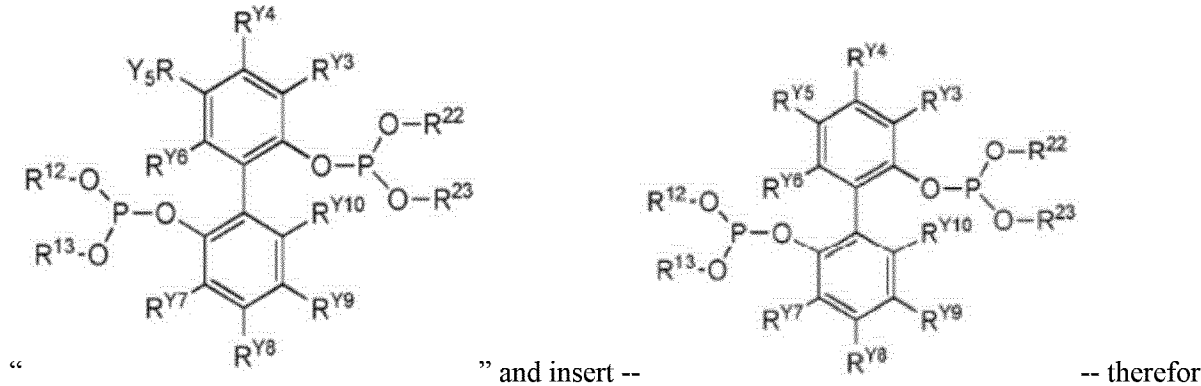

" and insert --                        -- therefor

In Column 56, Lines 64-65, in Claim 29, delete "(C1-C10) alkyl, and (C1-C10)alkoxy," and insert --$(C_1-C_{10})$alkyl, and $(C_1-C_{10})$alkoxy,-- therefor In Column 57, Lines 3-4, in Claim 30, delete "(C1-C10)alkyl or (C1-C10)alkoxy," and insert --$(C_1-C_{10})$alkyl or $(C_1-C_{10})$alkoxy,-- therefor In Column 57, Lines 6-10, in Claim 30, delete "(C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, or (C3-C10)cycloalkoxy(C1-C10)alkoxy;" and insert --$(C_1-C_{10})$alkyl, $(C_3-C_{10})$cycloalkyl, $(C_1-C_{10})$alkoxy, $(C_3-C_{10})$cycloalkoxy, $(C_3-C_{10})$cycloalkyl$(C_1-C_{10})$alkyl, $(C_3-C_{10})$cycloalkoxy$(C_1-C_{10})$alkyl, $(C_3-C_{10})$cycloalkyl$(C_1-C_{10})$alkoxy, or $(C_3-C_{10})$cycloalkoxy$(C_1-C_{10})$alkoxy;-- therefor In Column 57, Lines 11-12, in Claim 30, delete "(C1-C10)alkyl or (C1-C10)alkoxy," and insert --$(C_1-C_{10})$alkyl or $(C_1-C_{10})$alkoxy,-- therefor In Column 57, Line 13, in Claim 30, delete "(C1-C10)alkyl, or (C1-C10)alkoxy," and insert --($C_1$-$C_{10}$)alkyl or ($C_1$-$C_{10}$)alkoxy,-- therefor In Column 57, Lines 15-16, in Claim 30, delete "(C1-C10)alkyl or (C1-C10)alkoxy." and insert --($C_1$-$C_{10}$)alkyl or ($C_1$-$C_{10}$)alkoxy.-- therefor In Column 57, Line 41, in Claim 32, after "formula (IVA)", insert --:--

In Column 57, Line 59, in Claim 32, delete "1,or" and insert --1, or-- therefor

In Column 58, Line 2, in Claim 35, after "formula (XIII)", insert --:--

In Column 58, Line 24, in Claim 35, after "formula (XIV)", insert --:--

In Column 59, Lines 23-26, in Claim 39, delete "(C1-C10)alkyl, (C3-C10)cycloalkyl, (C3-C10)cycloalkyl(C1-C10)alkyl, (C6-C20)aryl, or (C6-C20)aryl(C1-C10)alkyl, wherein for any (C6-C20)aryl or (C6-C20)aryl(C1-C10)alkyl" and insert --($C_1$-$C_{10}$)alkyl, ($C_3$-$C_{10}$)cycloalkyl, ($C_3$-$C_{10}$)cycloalkyl($C_1$-$C_{10}$)alkyl, ($C_6$-$C_{20}$)aryl, or ($C_6$-$C_{20}$)aryl($C_1$-$C_{10}$)alkyl, wherein for any ($C_6$-$C_{20}$)aryl or ($C_6$-$C_{20}$)aryl($C_1$-$C_{10}$)alkyl-- therefor In Column 59, Lines 29-35, in Claim 39, delete "(C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, and (C6-C20)aryl(C1-C10)alkyl;" and insert --($C_1$-$C_{10}$)alkyl, ($C_3$-$C_{10}$)cycloalkyl, ($C_1$-$C_{10}$)alkoxy, ($C_3$-$C_{10}$)cycloalkoxy, ($C_3$-$C_{10}$)cycloalkyl($C_1$-$C_{10}$)alkyl, ($C_3$-$C_{10}$)cycloalkoxy($C_1$-$C_{10}$)alkyl, ($C_3$-$C_{10}$)cycloalkyl($C_1$-$C_{10}$)alkoxy, ($C_3$-$C_{10}$)cycloalkoxy($C_1$-$C_{10}$)alkoxy, ($C_6$-$C_{20}$)aryl, and ($C_6$-$C_{20}$)aryl($C_1$-$C_{10}$)alkyl;-- therefor In Column 59, Line 43, in Claim 39, delete "(C6-C20)arylene" and insert --($C_6$-$C_{20}$)arylene-- therefor In Column 59, Lines 45-51, in Claim 39, delete "(C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, (C6-C20)aryl(C1-C10)alkyl, fluorine, chlorine, bromine, or (C1-C10)haloalkyl;" and insert --($C_1$-$C_{10}$)alkyl, ($C_3$-$C_{10}$)cycloalkyl, ($C_1$-$C_{10}$)alkoxy, ($C_3$-$C_{10}$)cycloalkoxy, ($C_3$-$C_{10}$)cycloalkyl($C_1$-$C_{10}$)alkyl, ($C_3$-$C_{10}$)cycloalkoxy($C_1$-$C_{10}$)alkyl, ($C_3$-$C_{10}$)cycloalkyl($C_1$-$C_{10}$)alkoxy, ($C_3$-$C_{10}$)cycloalkoxy($C_1$-$C_{10}$)alkoxy, ($C_6$-$C_{20}$)aryl, ($C_6$-$C_{20}$)aryl($C_1$-$C_{10}$)alkyl, fluorine, chlorine, bromine, or ($C_1$-$C_{10}$)haloalkyl;-- therefor In Column 59, Lines 59-62, in Claim 39, delete "(C1-C10)alkyl, (C3-C10)cycloalkyl, (C3-C10)cycloalkyl(C1-C10)alkyl, (C6-C20)aryl, or (C6-C20)aryl(C1-C10)alkyl, wherein for any (C6-C20)aryl or (C6-C20)aryl(C1-C10)alkyl" and insert --($C_1$-$C_{10}$)alkyl, ($C_3$-$C_{10}$)cycloalkyl, ($C_3$-$C_{10}$)cycloalkyl($C_1$-$C_{10}$)alkyl, ($C_6$-$C_{20}$)aryl, or ($C_6$-$C_{20}$)aryl($C_1$-$C_{10}$)alkyl, wherein for any ($C_6$-$C_{20}$)aryl or ($C_6$-$C_{20}$)aryl($C_1$-$C_{10}$)alkyl-- therefor In Columns 59-60, Lines 65-67 and 1-3, in Claim 39, delete "(C1-C10)alkyl, (C3-C10)cycloalkyl, (C1-C10)alkoxy, (C3-C10)cycloalkoxy, (C3-C10)cycloalkyl(C1-C10)alkyl, (C3-

C10)cycloalkoxy(C1-C10)alkyl, (C3-C10)cycloalkyl(C1-C10)alkoxy, (C3-C10)cycloalkoxy(C1-C10)alkoxy, (C6-C20)aryl, and (C6-C20)aryl(C1-C10)alkyl;" and insert --$(C_1$-$C_{10})$alkyl, $(C_3$-$C_{10})$cycloalkyl, $(C_1$-$C_{10})$alkoxy, $(C_3$-$C_{10})$cycloalkoxy, $(C_3$-$C_{10})$cycloalkyl$(C_1$-$C_{10})$alkyl, $(C_3$-$C_{10})$cycloalkoxy$(C_1$-$C_{10})$alkyl, $(C_3$-$C_{10})$cycloalkyl$(C_1$-$C_{10})$alkoxy, $(C_3$-$C_{10})$cycloalkoxy$(C_1$-$C_{10})$alkoxy, $(C_6$-$C_{20})$aryl, and $(C_6$-$C_{20})$aryl$(C_1$-$C_{10})$alkyl;-- therefor In Column 60, Line 19, in Claim 40, delete "Formula" and insert --formula-- therefor In Column 60, Line 67, in Claim 43, after "formula (IVA)", insert --:--

In Column 61, Line 25, in Claim 46, delete "(C6-C20)aryl" and insert --$(C_6$-$C_{20})$aryl-- therefor In Column 61, Lines 28-32, in Claim 46, delete "(C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl and (C6-C20)aryl(C1-C10)alkyl, or" and insert --$(C_1$-$C_{10})$alkyl, $(C_3$-$C_{10})$cycloalkyl, $(C_1$-$C_{10})$alkoxy, $(C_3$-$C_{10})$cycloalkoxy, $(C_3$-$C_{10})$cycloalkyl$(C_1$-$C_{10})$alkyl, $(C_3$-$C_{10})$cycloalkoxy$(C_1$-$C_{10})$alkyl, $(C_3$-$C_{10})$cycloalkyl$(C_1$-$C_{10})$alkoxy, $(C_3$-$C_{10})$cycloalkoxy$(C_1$-$C_{10})$alkoxy, $(C_6$-$C_{20})$aryl and $(C_6$-$C_{20})$aryl$(C_1$-$C_{10})$alkyl, or-- therefor In Column 61, Line 41, in Claim 47, after "formula (II)", insert --:--

In Column 61, Formula (II), Lines 42-53, in Claim 47, delete " 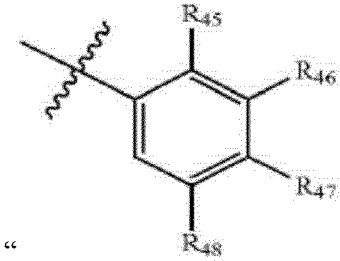 " and insert -- 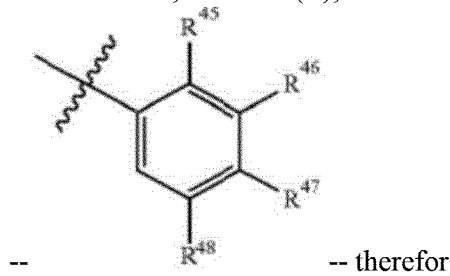 -- therefor In Column 61, Lines 56-60, in Claim 47, delete "(C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, and (C6-C20)aryl, or" and insert --$(C_1$-$C_{10})$alkyl, $(C_3$-$C_{10})$cycloalkyl, $(C_1$-$C_{10})$alkoxy, $(C_3$-$C_{10})$cycloalkoxy, $(C_3$-$C_{10})$cycloalkyl$(C_1$-$C_{10})$alkyl, $(C_3$-$C_{10})$cycloalkoxy$(C_1$-$C_{10})$alkyl, $(C_3$-$C_{10})$cycloalkyl$(C_1$-$C_{10})$alkoxy, $(C_3$-$C_{10})$cycloalkoxy$(C_1$-$C_{10})$alkoxy, and $(C_6$-$C_{20})$aryl, or-- therefor

CERTIFICATE OF CORRECTION (continued)
U.S. Pat. No. 9,834,505 B2

In Column 61, Lines 62-67, in Claim 47, delete "(C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, and (C6-C20)aryl." and insert --$(C_1$-$C_{10})$alkyl, $(C_3$-$C_{10})$cycloalkyl, $(C_1$-$C_{10})$alkoxy, $(C_3$-$C_{10})$cycloalkoxy, $(C_3$-$C_{10})$cycloalkyl$(C_1$-$C_{10})$alkyl, $(C_3$-$C_{10})$cycloalkoxy$(C_1$-$C_{10})$alkyl, $(C_3$-$C_{10})$cycloalkyl$(C_1$-$C_{10})$alkoxy, $(C_3$-$C_{10})$cycloalkoxy$(C_1$-$C_{10})$alkoxy, and $(C_6$-$C_{20})$aryl.-- therefor In Column 62, Line 2, in Claim 48, delete "(C6-C20)arylene" and insert --$(C_6$-$C_{20})$arylene-- therefor In Column 62, Lines 4-9, in Claim 48, delete "(C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, (C6-C20)aryl(C1-C10)alkyl, fluorine, chlorine, bromine, or (C1-C10)haloalkyl." and insert --$(C_1$-$C_{10})$alkyl, $(C_3$-$C_{10})$cycloalkyl, $(C_1$-$C_{10})$alkoxy, $(C_3$-$C_{10})$cycloalkoxy, $(C_3$-$C_{10})$cycloalkyl$(C_1$-$C_{10})$alkyl, $(C_3$-$C_{10})$cycloalkoxy$(C_1$-$C_{10})$alkyl, $(C_3$-$C_{10})$cycloalkyl$(C_1$-$C_{10})$alkoxy, $(C_3$-$C_{10})$cycloalkoxy$(C_1$-$C_{10})$alkoxy, $(C_6$-$C_{20})$aryl, $(C_6$-$C_{20})$aryl$(C_1$-$C_{10})$alkyl, fluorine, chlorine, bromine, or $(C_1$-$C_{10})$haloalkyl.-- therefor In Column 62, Lines 41-45, in Claim 49, delete "(C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, and (C3-C10)cycloalkoxy(C1-C10)alkoxy," and insert --$(C_1$-$C_{10})$alkyl, $(C_3$-$C_{10})$cycloalkyl, $(C_1$-$C_{10})$alkoxy, $(C_3$-$C_{10})$cycloalkoxy, $(C_3$-$C_{10})$cycloalkyl$(C_1$-$C_{10})$alkyl, $(C_3$-$C_{10})$cycloalkoxy$(C_1$-$C_{10})$alkyl, $(C_3$-$C_{10})$cycloalkyl$(C_1$-$C_{10})$alkoxy, and $(C_3$-$C_{10})$cycloalkoxy$(C_1$-$C_{10})$alkoxy,-- therefor In Column 62, Line 45, in Claim 49, delete "$R^{94}$," and insert --$R^{44}$,-- therefor In Column 62, Lines 47-51, in Claim 49, delete "(C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, and (C3-C10)cycloalkoxy(C1-C10)alkoxy." and insert --$(C_1$-$C_{10})$alkyl, $(C_3$-$C_{10})$cycloalkyl, $(C_1$-$C_{10})$alkoxy, $(C_3$-$C_{10})$cycloalkoxy, $(C_3$-$C_{10})$cycloalkyl$(C_1$-$C_{10})$alkyl, $(C_3$-$C_{10})$cycloalkoxy$(C_1$-$C_{10})$alkyl, $(C_3$-$C_{10})$cycloalkyl$(C_1$-$C_{10})$alkoxy, and $(C_3$-$C_{10})$cycloalkoxy$(C_1$-$C_{10})$alkoxy.-- therefor In Column 62, Line 60, in Claim 50, delete "(C1-C4)alkyl;" and insert --$(C_1$-$C_4)$alkyl;-- therefor In Column 62, Line 65, in Claim 50, delete "(C1-C4)alkyl." and insert --$(C_1$-$C_4)$alkyl.-- therefor In Column 63, Line 20, in Claim 52, after "formula (XII)", insert --:--

In Column 63, Formula (XII), Lines 21-37, in Claim 52, delete

" 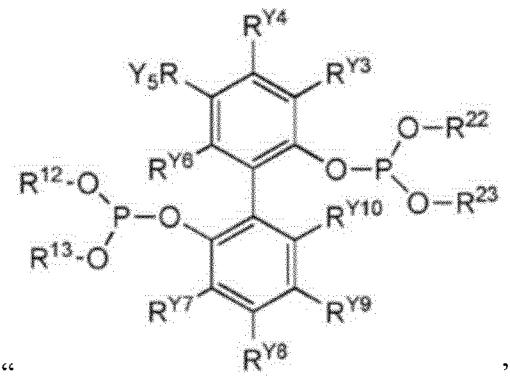 " and insert -- 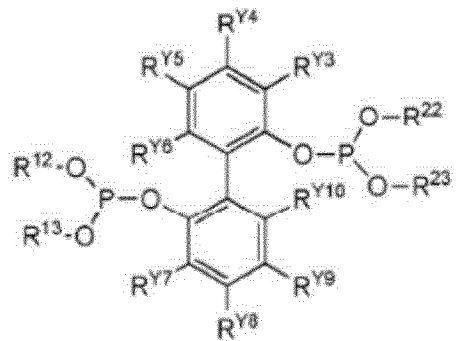 -- therefor

In Column 63, Line 41, in Claim 52, delete "(C1-C10) alkyl, and (C1-C10)alkoxy," and insert --$(C_1-C_{10})$alkyl, and $(C_1-C_{10})$alkoxy,-- therefor In Column 64, Lines 5-6, in Claim 53, delete "(C1-C10)alkyl or (C1-C10)alkoxy," and insert --$(C_1-C_{10})$alkyl or $(C_1-C_{10})$alkoxy,-- therefor In Column 64, Lines 8-12, in Claim 53, delete "(C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, or (C3-C10)cycloalkoxy(C1-C10)alkoxy;" and insert --$(C_1-C_{10})$alkyl, $(C_3-C_{10})$cycloalkyl, $(C_1-C_{10})$alkoxy, $(C_3-C_{10})$cycloalkoxy, $(C_3-C_{10})$cycloalkyl$(C_1-C_{10})$alkyl, $(C_3-C_{10})$cycloalkoxy$(C_1-C_{10})$alkyl, $(C_3-C_{10})$cycloalkyl$(C_1-C_{10})$alkoxy, or $(C_3-C_{10})$cycloalkoxy$(C_1-C_{10})$alkoxy;-- therefor In Column 64, Lines 13-14, in Claim 53, delete "(C1-C10)alkyl or (C1-C10)alkoxy," and insert --$(C_1-C_{10})$alkyl or $(C_1-C_{10})$alkoxy,-- therefor In Column 64, Line 15, in Claim 53, delete "(C1-C10)alkyl, or (C1-C10)alkoxy," and insert --$(C_1-C_{10})$alkyl, or $(C_1-C_{10})$alkoxy,-- therefor In Column 64, Lines 17-18, in Claim 53, delete "(C1-C10)alkyl or (C1-C10)alkoxy." and insert --$(C_1-C_{10})$alkyl or $(C_1-C_{10})$alkoxy.-- therefor